(12) United States Patent
Fliri et al.

(10) Patent No.: US 9,382,295 B2
(45) Date of Patent: Jul. 5, 2016

(54) CYCLIC DEPSIPEPTIDE COMPOUNDS AND THEIR USES

(71) Applicant: Cypralis Limited, Ongar (GB)

(72) Inventors: Hans Georg Fliri, Ongar (GB); Rhonan Lee Ford, Ongar (GB); Antonio Kuok Keong Vong, Ongar (GB)

(73) Assignee: Cypralis Limited, Ongar, Essex (GB)

( * ) Notice: Subject to any disclaimer, the term of this patent is extended or adjusted under 35 U.S.C. 154(b) by 0 days.

(21) Appl. No.: 14/433,327

(22) PCT Filed: Oct. 2, 2013

(86) PCT No.: PCT/GB2013/052570
§ 371 (c)(1),
(2) Date: Apr. 2, 2015

(87) PCT Pub. No.: WO2014/053834
PCT Pub. Date: Apr. 10, 2014

(65) Prior Publication Data
US 2015/0259386 A1    Sep. 17, 2015

(30) Foreign Application Priority Data

Oct. 2, 2012   (GB) .................................. 1217560.0

(51) Int. Cl.
*A61K 38/12*     (2006.01)
*C07K 11/02*     (2006.01)
*C07K 7/56*      (2006.01)
*A61K 38/00*     (2006.01)

(52) U.S. Cl.
CPC . *C07K 11/02* (2013.01); *C07K 7/56* (2013.01); *A61K 38/00* (2013.01)

(58) Field of Classification Search
CPC .......... A61K 38/13; A61K 38/12; A61K 8/64
See application file for complete search history.

(56) References Cited

U.S. PATENT DOCUMENTS

| 2009/0023640 A1 | 1/2009 | Scalfaro et al. |
| 2011/0206637 A1 | 8/2011 | Or et al. |

FOREIGN PATENT DOCUMENTS

| WO | 2010052559 | | 5/2010 |
| WO | 2011141891 | A1 | 11/2011 |

*Primary Examiner* — James H Alstrum Acevedo
*Assistant Examiner* — Kaipeen Yang
(74) *Attorney, Agent, or Firm* — McCarter & English, LLP; Steven G. Davis; Mei Bai

(57) ABSTRACT

The present invention relates to novel cycloundecadepsipeptide compounds and their analoges which bind and inhibit cyclophilins, have reduced immunosuppressive activity and improved physicochemical properties including water solubility. The present invention further relates to pharmaceutical compositions containing said depsipeptide compounds and their analoges for use in the treatment or prevention of diseases and pathologies which may be ameliorated by the inhibition of cyclophilin activity.

20 Claims, No Drawings

CYCLIC DEPSIPEPTIDE COMPOUNDS AND THEIR USES

This application is a 35 U.S.C. §371 national stage filing of International Application No. PCT/GB2013/052570, filed on Oct. 2, 2013, which claims the benefit of United Kingdom Patent Application No. 1217560.0, filed on Oct. 2, 2012. Each of the foregoing applications is incorporated herein by reference in its entirety.

FIELD OF THE INVENTION

The present invention relates to novel cycloundecadepsipeptide compounds and their analogues which bind and inhibit cyclophilins, have reduced immunosuppressive activity and improved physicochemical properties including water solubility, and inhibit extracellularly secreted cyclophilins or their ability to bind their cognate cell surface receptors, and inhibit intracellular cyclophilins. The present invention further relates to pharmaceutical compositions containing said depsipeptide compounds and their analogues for use in the treatment or prevention of diseases and pathologies.

BACKGROUND OF THE INVENTION

It is now well established that cyclophilins represent one family of a large group of proteins which all possess peptidyl-prolyl cis/trans isomerase (PPIase) activity, the other families being FK-506-binding proteins and parvulins. Cyclophilins are ubiquitous enzymes, being found in all living organisms with high structural conservation across species. In humans there are seven major cyclophilins: cyclophilin-A, cyclophilin-B, cyclophilin-C, cyclophilin-D, cyclophilin-E, cyclophilin-40, and NK-cyclophilin. The most abundant protein is cyclophilin-A, which accounts for 0.6% of total cytosolic protein, whilst cyclophilin-D is found predominantly in cell mitochondria. Cyclophilin-B and cyclophilin-C are located largely in the endoplasmic reticulum whilst cyclophilin-E is located in the cell nucleus. Cyclophilin-40 is found in the cytosol, as is NK-cyclophilin (named as such because it was first discovered in human natural killer cells). The cyclophilins have also been observed to translocate between cellular compartments and, under certain circumstances, to be secreted, properties which contribute to their physiological functions. Cyclophilins have the specific enzymatic capability of accelerating the rate of cis/trans isomerisation of peptidyl-prolyl bonds and speed up the rate of folding of newly synthesised or denatured proteins. PPIases also play a role in the repair of proteins which have been damaged through exposure of cells to oxidation, ultraviolet radiation, thermal stress and pH changes. Cyclophilins A and B can be secreted from cells and the secreted proteins act as pro-inflammatory cytokines. Additionally, cyclophilins play a role in intracellular protein trafficking and cyclophilin-D has a modulatory role in the opening of the mitochondrial permeability transition pore.

The best known ligand and inhibitor for cyclophilins is cyclosporin A (CsA), binding to cyclophilins A, B, and D with nanomolar affinity. The well-known immunosuppressive activity of CsA is manifested not through cyclophilin inhibitory activity, but is a property of the complex formed with cyclophilin A: The whole complex binds to the protein calcineurin, a phosphatase whose activity is essential to initiate lymphokine gene transcription and the immune response. Thus, immunosuppression is the result of the formation of a ternary complex cyclosporin/cyclophilin A/calcineurin and displayed only by cyclosporin A and a few selected analogues or derivatives.

Cyclophilin-Mediated Diseases

Of particular importance for the present invention is that cyclophilins have been found to be involved in many diseases, including chronic and acute inflammatory disorders, malignancies, viral, fungal and parasitic infections, central nervous system disorders, tissue degenerative disorders, and ischemia/reperfusion injury, cardiovascular disease, respiratory disease, metabolic syndrome, obesity, diabetes and diseases associated with mitochondrial dysfunction.

Cyclophilins have an important role in viral life-cycles and the anti-viral activity of the non-immunosuppresive analogue NIM-811, and by implication that of cyclosporin A, has been linked to the inhibition of cyclophilin A. Cyclosporin A and analogues have been shown to have activity against HIV, HCV and HBV and several drugs are undergoing clinical trials for treatment of HCV [Fischer G., Gallay P., Hopkins S. (2010) Cyclophilin inhibitors for the treatment of HCV infection. Curr. Opin. Investig. Drugs 11:911-918]. Studies suggesting an involvement of cyclophilins in the life-cycles of other viruses, for example severe acute respiratory coronavirus, vaccinia virus, papilloma virus, and herpes simplex virus, suggest that cyclophilin inhibitors may also have utility for the treatment of infection by other viruses. The activity of cyclophilin inhibitors against HCV suggests that they might also be efficacious against other viruses [Zhou D., Mei Q., Li J., He H., (2012) Cyclophilin A and viral infections. Biochem. Biophys. Res. Comm. 424:647-650], such as the Flaviviridae viruses, for example Dengue virus, yellow fever virus and West Nile virus.

The immune-suppressive functions of cyclosporin A have long been recognised and important to its clinical use in transplantation, however it and the nonimmune-suppressive analogues mediate anti-inflammatory actions through their activity at cyclophilins also. Furthermore, although cyclophilin A, B, C, D are the most studied, to date seventeen cyclophilins have been identified in the human genome and knowledge of their physiological functions is incomplete. Furthermore, there is evidence that cyclophilins may be secreted and act as mediators signalling via cell surface receptors. CD147 has been identified as one such receptor and is implicated in the functions of cyclophilins in inflammation [Yurchenko V., Constant S., Eisenmesser E., Bukrinsky M. (2010) Cyclophilin-CD147 interactions: a new target for anti-inflammatory therapeutics. Clin. Exp. Immunol. 160:305-317]. A significant body of research has implicated cyclophilins in the control of inflammatory processes involved in the aetiology of inflammatory disease [Kovarik J. (2013) From immunosuppression to immunomodulation current principles and future strategies. Pathobiology 80:275-281] including but not limited to: arthritis, such as rheumatoid arthritis; respiratory diseases, such as allergic asthma, allergic rhinitis, chronic asthma, COPD, pulmonary hypertension; dermatological diseases, such as psoriasis, atopic dermatitis, urticaria, mastocytosis; opthalmalogical diseases, such as uveitis, conjunctivitis, dry eye, age-related macular degeneration; inflammatory bowel disease; periodontitis; lupus. Also an increasing body of evidence now suggests that chronic inflammatory processes may underlie chronic diseases leading to tissue degeneration or fibrosis or metabolic instability, suggesting that ligands of cyclophilins may have utility in chronic diseases including: degenerative disorders of the nervous system, such as Alzheimer's disease, multiple sclerosis, amyotrophic lateral sclerosis, Parkinson's disease, Huntington's chorea, glaucoma; cardiovascular diseases, such as myocarditis, cardiomyopathy, atherosclerosis, restenosis; bowel diseases such as ulcerative colitis, Crohn's disease; liver disease, such as cirrhosis or alcohol or non-alcohol fatty liver disease; metabolic syndrome and diabetes.

Cyclophilins are regulated during disease and changes in expression have been associated with cancer [Lee J. and Kim S S. (2010) Current implications of cyclophilins in human cancers. J. Exp. Clin. Cancer Res. 29:97]. The receptor for secreted cyclophilin, CD147 has also been associated with cancer and linked to proliferation, tumour invasiveness and chemo-resistance. Conversely cyclophilin D activity has been associated with the mitochondrial transition pore and the cell death induced by several anti-cancer regimens. Cyclophilin inhibitors, optimised for selectivity between cyclophilins or tissue or subcellular distribution, may have utility in a wide range of cancer types including but not limited to, melanoma, lymphoma, epithelial ovarian, breast, prostate, oral, endometrial, hepatic, pancreatic, or skin cancers.

It should be noted that the relative roles of secreted cyclophilins, or of a particular cyclophilin, gives rise to the opportunity to design pan-cyclophilin inhibitors or inhibitors with selective inhibitory profiles, or with selective distribution patterns across tissues or physiological compartments, in order to optimise the therapeutic index for a given disease.

Of particular importance for the present invention is cyclophilin D (PPIF), which is located in the mitochondrial matrix where it serves as a modulatory component of the mitochondrial permeability transition pore (MPTP). Mitochondrial permeability transition is a phenomenon induced by high levels of matrix calcium and is characterized by the opening of the MPTP. Activation of the MPTP results in loss of the mitochondrial membrane potential, expansion of the matrix, rupture of the mitochondrial outer membrane and release of mitochondrial proteins into the cytosol where they activate cellular death programs. The induction of the MPTP also causes mitochondria to become depolarized, which negatively affects the production of ATP, the cell's main source of energy, creating an energy deficit in the cell. Much research has found that the fate of the cell after an insult depends on the extent of permeability transition; if it occurs to only a slight extent and the energy deficit is transient, the cell may recover, whereas occurrence to increasingly larger extents activates the death programs leading first to apoptosis and in the extreme to necrosis.

The central role of cyclophilin D in this chain of events has been further substantiated by gene deletion or silencing experiments.

The induction of mitochondrial permeability transition is implicated in many diseases and conditions including: traumatic or acute events such as ischaemia/reperfusion injury to organs, traumatic brain injury, spinal cord injury, stroke, myocardial infarction; and chronic diseases involving the progressive loss or dysfunction of tissues leading to associated symptoms, such as congestive heart failure, cardiac diseases, CNS disorders [Martin L J. (2012) Biology of mitochondria in neurodegenerative diseases. Prog. Mol. Biol. Transl. Sci. 107:355-415] leading to dementia or psychiatric impairments, Alzheimer's disease, Parkinson's disease, Huntingdon's chorea; epilepsy; amyotrophic lateral sclerosis; multiple sclerosis; muscular dystrophies; glaucoma; macular degeneration; diabetic retinopathy; retinal dystrophies, such as retinitis pigmentosa; liver disease; diseases caused by mitochondrial dysfunction, such as Leber's hereditary optic neuropathy (LHON), Friedreich's ataxia, MELAS syndrome, myoclonic epilepsy with ragged red fibres (MERRF); cell death due to infection, toxins or metabolic abnormality.

Accordingly, the MPTP is accepted as a therapeutic target for pharmacological intervention to block tissue and nerve damage originating from mitochondrial energy deficiencies and abnormalities. Inhibiting the opening of the MPTP by inhibition of cyclophilin D can treat and/or prevent disorders and diseases associated with mitochondrial dysfunction.

Agents that are known to block cyclophilin functions include the immune suppressant cyclosporin A (CsA) and some of its non-immunosuppressive derivatives such as N-methyl-Val-4-cyclosporin or NIM-811 (N-methyl-Ile-4-cyclosporin), 2-aminoethoxydiphenyl borate (2-APB), sanglifehrin, and bongkrekic acid. Cyclosporin A has been in clinical use as immunosuppressant to prevent rejection of organ transplants since 1983. While life-saving for organ transplant recipients, the drug has a narrow therapeutic index that limits its wider use. Toxicities and adverse effects include renal and hepatotoxicity, hypertension, gingival hyperplasia, hirsutism, nausea, headache, tremors and paresthesia. Some of these effects are associated to the mechanism of immunosuppression, which is generally considered an undesired property except in transplantation. In fact, this activity predisposes subjects to an increased risk of viral infections and malignancies. Cyclosporin is very insoluble in aqueous systems and as a consequence it is usually administered by mouth in form of suspensions or emulsions. Non-aqueous formulations have been developed for intravenous administration, but the additives used in these preparations are often associated with adverse effects themselves, notably anaphylactic reactions. There is thus a pronounced therapeutic need to develop novel cyclophilin inhibitors that have reduced or no immunosuppressive activity, and that are permeable and soluble, such that they can easily be formulated as therapeutic agents. The present invention provides compounds that fulfil these requirements.

Cycloundecadepsipeptides—Cyclophilin Inhibitors with reduced Immunosuppression

The first cycloundecadepsipeptide to be identified to be a potent inhibitor of cyclophilins has the structure shown in formula A.

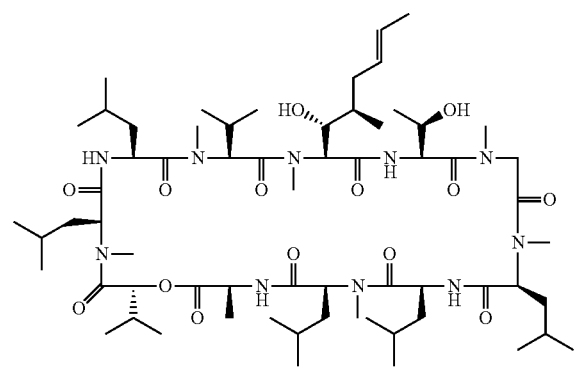

formula A (Compound 1)

In accordance with WO 2011/141891, this compound can also be described as Cyclo-(MeBmt-Thr-Sar-MeLeu-Leu-MeLeu-Ala-D-Hiv-MeLeu-Leu-MeVal). Compounds of this family can generally be designated as Cyclo (AXX$_1$ AXX$_2$ AXX$_3$ AXX$_4$ AXX$_5$ AXX$_6$ AXX$_7$ D-Hiv AXX$_9$
       1    2    3    4    5    6    7    8    9

AXX$_{10}$ AXX$_{11}$)
   10    11

In which AXX$_1$ is N-methyl-(4R)-4-but-2E-en-1-yl-4-methyl-(L)-threonine, and D-Hiv is (D)-2-hydroxyisovalerianic acid.

The main drawback to using the compound of formula A per se for the treatment of the above mentioned indications is its high level of immunosuppressive activity and its poor aqueous solubility.

More recently, new cycloundecadepsipeptides which retain their ability to bind cyclophilins but with significantly reduced immunosuppressive properties have been disclosed (WO2010/052559 A1). This application claims the use of certain cycloundecadepsipeptides as compounds for treating viral infections, notably by Hepatitis C.

In a further disclosure, (WO2011/141891 A1) report the use of certain cycloundecadepsipeptides as compounds for treating cell death associated disorders or diseases.

The structural modifications described in these patents serve to eliminate the immunosuppressive properties from the parent molecule. However, they do not achieve improvement of the low solubility of the molecules in aqueous systems.

It was now found that certain modifications of the residue 1 of the cycloundecadepsipeptide have not only good solubility in aqueous solvents but at the same time also strongly reduced immunosuppressive activity.

SUMMARY OF THE INVENTION

According to one aspect, compounds of the present invention comprise novel cycloundecadepsipeptides which have reduced immunosuppressive activity. According to another aspect, the compounds have improved water solubility. According to another aspect, the compounds have high affinity for cyclophilins, including cyclophilin-A and cyclophilin-D. According to other aspects, compounds of the present invention comprise cycloundecadepsipeptide analogues that are useful in respect of treating cyclophilin-mediated diseases or conditions and for developing therapies with respect to such diseases and conditions.

Disclosed herein are cycloundecadepsipeptides compounds which can be designated as Cyclo (AXX$_1$ AXX$_2$ AXX$_3$ AXX$_4$ AXX$_5$ AXX$_6$ AXX$_7$ D-Hiv AXX$_9$
       1    2    3    4    5    6    7    8    9

AXX$_{10}$ AXX$_{11}$)
   10    11

In which AXX$_1$ contains a nitrogen atom in the side chain, as further described below, and, AXX$_2$ is Abu, Val, Thr, Thr (OMe), Thr(OAc), Thr(OCOCH$_2$CH$_2$CH$_2$OH), or an alternative threonine ester or threonine-O-alkyl or substituted O-alkyl moiety, Nva, 5-hydroxy-Nva (Hnv) or a moiety of type C(=O)CH$_3$ or C(=N—Y)CH$_3$ where Y is OH, NH$_2$ or O- or N-alkyl substituted alkyl versions thereof;

AXX$_3$ is optionally substituted alkylene, D-MeAla, D-3-fluoro-MeAla, D-MeSer, D-MeSer(OAc), D-Me Ser(OCH$_2$CH$_2$OH), D-Me Ser(OCH$_2$CH$_2$NEt$_2$), D-MeAsp (OMe) or a D-amino acid with a side chain selected from hydrogen, alkyl, substituted alkyl, alkoxy, substituted alkoxy, alkylthio or substituted alkylthio;

AXX$_4$ is MeLeu, MeIle, MeMet, MeVal, MeThr, MeThr (OAc), MeAla, EtVal, EtIle, EtPhe, EtTyr, EtThr(OAc), MeThr(OAc), MeTyr, MeTyr(OAc), MeTyr(OMe), MePhe, MeMet(Ox) wherein the sulphur atom of methionine is sulphoxide or sulphone;

AXX$_5$ is Leu, Val, Ile, Gly, Abu;
AXX$_6$ is MeAla, Sar, MeLeu;
AXX$_7$ is Gly, Ala;
D-Hiv is (D)-2-hydroxyisovalerianic acid;
AXX$_9$ is MeLeu;
AXX$_{10}$ is Leu; and
AXX$_{11}$ is MeVal.

In accordance with the aspects of the invention there is provided a compound having the formula (1):

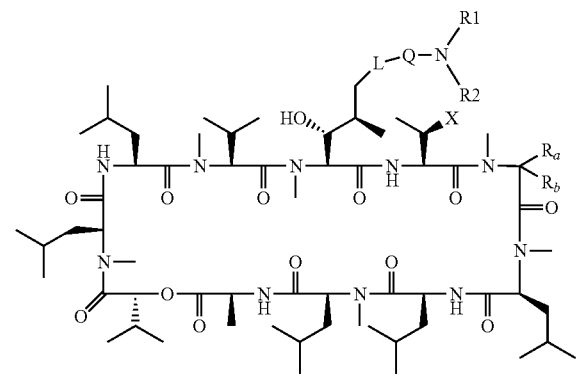

or a pharmaceutically acceptable salt, tautomer or N-oxide thereof, wherein:

L represents a bond or an optionally substituted, optionally partially unsaturated chain of 1-6 carbon atoms with optional additional heteroatoms atoms in the chain, and may be optionally branched and optionally linked to R$_1$ to form a ring structure containing one or more nitrogen atoms, Q represents a primary, secondary or tertiary covalent bond, a carbonyl group and optionally a linking group to R1, R1 and R2 may be absent or independently represent H, alkyl, substituted alkyl, optionally substituted cycloalkyl, optionally substituted aryl, optionally substituted heteroaryl, —COR$_3$, —CO$_2$R$_3$, —OR$_4$, —NR$_4$R$_5$, CONR$_4$R$_5$, —C(=NR$_6$)NR$_4$R$_5$, —C(=NR$_6$)OR$_3$ and optionally R1 and R2 may together with the nitrogen atom to which they are attached form a 4-7 membered aryl, cycloalkyl or heterocyclic ring which may be further fused or optionally substituted, R3 represents alkyl, substituted alkyl, cycloalkyl, optionally substituted aryl, or optionally substituted heteroaryl, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, R6 represents H, alkyl, substituted alkyl, cycloalkyl, optionally substituted aryl, or optionally substituted heteroaryl, X represents H, OH, OC(=O)-alkyl, OC(=O)-substituted alkyl, O-alkyl, O-substituted alkyl, carbonyl (=O) or imine (=N—Y) where Y is —OR$_4$ or —NR$_4$R$_5$, $R_a$ represents hydrogen, alkyl, substituted alkyl, alkoxy, substituted alkoxy, alkylthio, substituted alkylthio or optionally substituted alkylene, and $R_b$ represents hydrogen or is absent.

The group L-Q-NR1R2 may comprise a primary, secondary or tertiary amino group attached via an optionally substituted alkyl linker. The group L-Q-NR1R2 may comprise —C(═O)—NR1R2.

The group L-Q-NR1R2 may comprise a primary or secondary amide, urea, amidine, guanidine or carbamate group attached via an optionally substituted alkyl linker. Q may be a carbonyl group such that amide may be of orientation —C(═O)N as well as —NC(═O). Where Q is a carbonyl group, L may be absent.

The group L-Q-NR1R2 may comprise a C═N double bond moiety, for example C═N—OH, C═N—OR, C═N—NH2, C═N—NHR or C═N—NRR. The group at AXX2 may also comprise a carbonyl or a C═N double bond moiety, for example C═N—OH, C═N—OR, C═N—NH2, C═N—NHR or C═N—NRR.

The group L-Q-NR1R2 may comprise a nitrogen containing heterocyclic ring. The heterocyclic ring may be a 4-7 membered aryl, cycloalkyl or heterocyclic ring which may be further fused or optionally substituted.

Disclosed herein are pharmaceutical compositions containing a compound disclosed herein.

Compounds disclosed herein may be used in the manufacture of medicaments. The medicaments or pharmaceutical compositions may be used in the treatment or prevention of diseases, pathologies or symptomatology which may be ameliorated by inhibition of cyclophilin activity.

DETAILED DESCRIPTION OF THE INVENTION

Compounds of the present invention comprise novel cycloundecadepsipeptides which have reduced immunosuppressive activity. According to another aspect, the compounds have improved water solubility. According to another aspect, the compounds have high affinity for cyclophilins, including cyclophilin-A and cyclophilin-D. According to other aspects, compounds of the present invention comprise cycloundecadepsipeptide analogues that are useful in respect of treating cyclophilin-mediated diseases or conditions and for developing therapies with respect to such diseases and conditions.

In accordance with the aspects of the invention there is provided a compound having the formula (1):

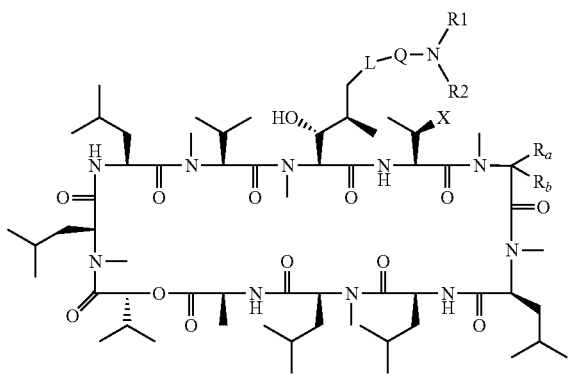

or a pharmaceutically acceptable salt, tautomer or N-oxide thereof, wherein:

L represents an optionally substituted, optionally partially unsaturated chain of 1-6 carbon atoms with optional additional heteroatoms atoms in the chain, and may be optionally branched and optionally linked to $R_1$ to form a ring structure containing one or more nitrogen atoms, Q represents a primary, secondary or tertiary covalent bond, a carbonyl group and optionally a linking group to R1, R1 and R2 may be absent or independently represent H, alkyl, substituted alkyl, optionally substituted cycloalkyl, optionally substituted aryl, optionally substituted heteroaryl, —COR₃, —CO₂R₃, —OR₄, —NR₄R₅, —CONR₄R₅, —C(═NR₆)NR₄R₅, —C(═NR₆)OR₃ and optionally R1 and R2 may together with the nitrogen atom to which they are attached form a 4-7 membered aryl, cycloalkyl or heterocyclic ring which may be further fused or optionally substituted, R3 represents alkyl, substituted alkyl, cycloalkyl, optionally substituted aryl, or optionally substituted heteroaryl, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, R6 represents H, alkyl, substituted alkyl, cycloalkyl, optionally substituted aryl, or optionally substituted heteroaryl, X represents H, OH, OC(═O)-alkyl, OC(═O)-substituted alkyl, O-alkyl, O-substituted alkyl, carbonyl (═O) or imine (═N—Y) where Y is —OR₄ or —NR₄R₅, $R_a$ represents hydrogen, alkyl, substituted alkyl, alkoxy, substituted alkoxy, alkylthio, substituted alkylthio or optionally substituted alkylene, and $R_b$ represents hydrogen or is absent.

The group L-Q-NR1R2 may comprise a primary, secondary or tertiary amino group attached via an optionally substituted alkyl linker. The group L-Q-NR1R2 may comprise —C(═O)—NR1R2.

The group L-Q-NR1R2 may comprise a primary or secondary amide, urea, amidine, guanidine or carbamate group attached via an optionally substituted alkyl linker. Q may be a carbonyl group such that amide may be of orientation —C(═O)N as well as —NC(═O). Where Q is a carbonyl group, L may be absent.

The group L-Q-NR1R2 may comprise a C═N double bond moiety, for example C═N—OH, C═N—OR, C═N—NH2, C═N—NHR or C═N—NRR.

The group L-Q-NR1R2 may comprise a nitrogen containing heterocyclic ring. The heterocyclic ring may be a 4-7 membered aryl, cycloalkyl or heterocyclic ring which may be further fused or optionally substituted.

Linking moiety L may be a bond, or 1-6 carbon atoms. L may contain one or more heteroatoms in the chain. L may contain O, N or S atoms interspersed between the carbon atoms. L may contain a branch point. L may contain one or more double or triple bonds such that L may be partially unsaturated. L may link with R1 or R2 to form a ring containing one or more nitrogen atoms. L may be (CH₂)n where n is 1-4. L may contain a single double bond. L may be CH═CH— or CH═CH—CH₂—. L may be absent where Q is a carbonyl group.

Moiety Q may be a covalent bond. Q may be a primary (single) covalent bond, where both R1 and R2 are present. Q may be a secondary covalent (double) bond, where only a single R1 group is present. Q may be a tertiary covalent (triple) bond to make a cyano (CN) group where R1 and R2 are absent. Q may be a carbonyl group such that Q-N is a C(=O)—N amide group. Q may link with R1 or R2 to form a ring containing one or more nitrogen atoms.

Exemplary compounds may be where R1 and R2 are together with the nitrogen atom to which they are attached form a 4-7 membered aryl, cycloalkyl or heterocyclic ring which may be further fused or optionally substituted or optionally partially unsaturated. Exemplary rings include optionally substituted morpholinyl, optionally substituted piperazinyl, optionally substituted oxazepinyl, optionally substituted pyrrolidinyl, optionally substituted piperidinyl, optionally substituted fused pyrrolidinyl, optionally substituted thiomorpholinyl, or the S oxides thereof. The ring may be fused to form a bicyclic system.

R1 and R2 may be absent or independently represent H, alkyl, substituted alkyl, —COR$_3$, —CO$_2$R$_3$, —OR$_4$, —NR$_4$R$_5$, CONR$_4$R$_5$, —C(=NR$_6$)NR$_4$R$_5$, —C(=NR$_6$)OR$_3$ and optionally R1 and R2 may together with the nitrogen atom to which they are attached form a 4-7 membered aryl, cycloalkyl or heterocyclic ring which may be further fused or optionally substituted.

R1 and/or R2 may be H. R1 and/or R2 may be alkyl or substituted alkyl. R1 and/or R2 may be methyl or ethyl. R1 and/or R2 may be isopropyl. R1 and/or R2 may be aryl or substituted aryl. R1 and/or R2 may be heteroaryl or substituted heteroaryl. R1 and/or R2 may be an alkyl group substituted with a further ring. The ring may be aliphatic or aromatic, and may contain one or more heteroatoms. R1 and/or R2 may be of type CH$_2$-ring or CH$_2$—CH$_2$-ring. The ring may be a 2, 3 or 4-pyridyl. The ring may be a 5 membered heteroaryl ring. The 5 membered ring may contain 2, 3 or 4 nitrogen atoms. The ring may be a 6 membered ring. The 6 membered ring may contain one or two oxygen or nitrogen atoms. In each case the specified ring may be optionally further substituted. R1 and/or R2 may be an alkyl group substituted with a heteroatom in the alkyl chain. R1 and/or R2 may be a group of type CH$_2$—CH$_2$—O-alkyl. R1 and/or R2 may be a cycloalkyl or heterocycloalkyl group. The cycloalkyl or heterocycloalkyl group may be further substituted.

Exemplary groups for R1 and/or R2 include methyl, ethyl, isopropyl, (CH$_2$)n-pyridyl, (CH$_2$)n-pyrazoyl, (CH$_2$)n-tetrazoyl, —(CH$_2$)n-1,4-dioxanyl, (CH$_2$)n-OMe, (CH$_2$)n-tetrahydropyranyl, (CH$_2$)n-CN where n is 1, 2 or 3.

R1 or R2 may represent an amide COR$_3$ where R3 represents alkyl, substituted alkyl, cycloalkyl, optionally substituted aryl, or optionally substituted heteroaryl. R1 or R2 may represent an amide COCH$_3$. R1 or R2 may represent a carbamate CO$_2$R$_3$ where R3 represents alkyl, substituted alkyl, cycloalkyl, optionally substituted aryl, or optionally substituted heteroaryl. R1 or R2 may represent an oxime or hydroxylamine OR$_4$ where R4 represents H, alkyl, substituted alkyl, cycloalkyl, optionally substituted aryl, or optionally substituted heteroaryl. R1 or R2 may represent an hydrazone NR$_4$R$_5$ where R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted. R1 or R2 may represent —C(=NR$_6$)NR$_4$R$_5$ or —C(=NR$_6$)OR$_3$ where R3 represents alkyl, substituted alkyl, cycloalkyl, optionally substituted aryl, or optionally substituted heteroaryl and R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted and R6 represents H, alkyl, substituted alkyl, cycloalkyl, optionally substituted aryl, or optionally substituted heteroaryl.

Exemplary compounds include those based around formula

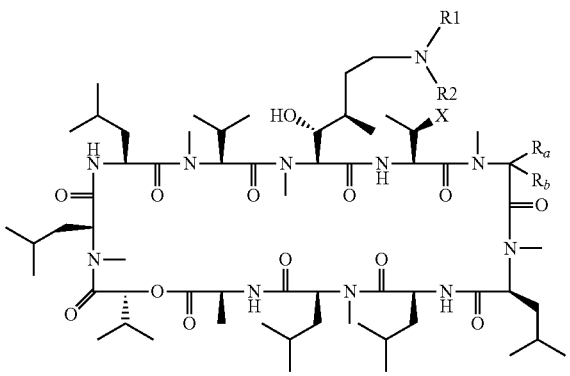

or a pharmaceutically acceptable salt, tautomer or N-oxide thereof, wherein:

R1 and R2 may independently represent H, alkyl, substituted alkyl, optionally substituted cycloalkyl, optionally substituted aryl, optionally substituted heteroaryl, —COR$_3$, —CO$_2$R$_3$, —OR$_4$, —NR$_4$R$_5$, —CONR$_4$R$_5$, —C(=NR$_6$)NR$_4$R$_5$, —C(=NR$_6$)OR$_3$ and optionally R1 and R2 may together with the nitrogen atom to which they are attached form a 4-7 membered aryl, cycloalkyl or heterocyclic ring which may be further fused or optionally substituted, R3 represents alkyl, substituted alkyl, cycloalkyl, optionally substituted aryl, or optionally substituted heteroaryl, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, R6 represents H, alkyl, substituted alkyl, cycloalkyl, optionally substituted aryl, or optionally substituted heteroaryl, X represents H, OH, OC(=O)-alkyl, OC(=O)-substituted alkyl, O-alkyl, O-substituted alkyl, carbonyl (=O) or imine (=N—Y) where Y is —OR$_4$ or —NR$_4$R$_5$, R$_a$ represents hydrogen, alkyl, substituted alkyl, alkoxy, substituted alkoxy, alkylthio, substituted alkylthio or optionally substituted alkylene, and R$_b$ represents hydrogen or is absent.

X represents H, OH, OC(=O)-alkyl, OC(=O)-substituted alkyl, O-alkyl, O-substituted alkyl, carbonyl (=O) or imine (=N—Y) where Y is —OR$_4$ or —NR$_4$R$_5$. Where X is OH, the amino acid is threonine. The hydroxyl moiety of the threonine can be in the form of an ester or O-alkyl group where the ester or alkyl group is optionally substituted. For example, the amino acid may be Thr(OMe), Thr(OAc), Thr (OCOCH$_2$CH$_2$CH$_2$OH), or an alternative threonine ester or threonine-O-alkyl or substituted O-alkyl moiety. The ester can be in the form OC(=O)-alkyl or OC(=O)-substituted alkyl. X can represent a group of type —OCOR$_3$ or —OCO$_2$R$_3$, where R3 represents alkyl, substituted alkyl, cycloalkyl, optionally substituted aryl, or optionally substituted heteroaryl. X can represent a group of type —OR$_4$ where R4 represents H, alkyl, substituted alkyl, cycloalkyl, optionally substituted aryl, or optionally substituted heteroaryl. X can be present as a carbonyl group (═O). X can be present as an imine (═N—Y) where Y is —OR$_4$ or —NR$_4$R$_5$ where R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted.

R$_a$ represents hydrogen, alkyl, substituted alkyl, alkoxy, substituted alkoxy, alkylthio, substituted alkylthio or optionally substituted alkylene. Ra includes substituted alkyl groups of type —S—R7, —CH2-S—R7 and the sulfoxide and sulfone analogues thereof where R7 represents H, alkyl or substituted alkyl.

Exemplary groups for Ra include: ═CH$_2$; —CH$_2$SH; —CH$_2$—S—(CH$_2$)$_n$N—R$_4$R$_5$, where R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted and n is 1-4; —CH$_2$—S—(CH$_2$)$_n$-aryl where n is 1-4; —CH$_2$—S—(CH$_2$)$_n$-heroaryl where n is 1-4; —CH$_2$—S—CH$_3$; —CH$_2$—S-cycloalkyl; CH$_2$—S-heterocycloalkyl; —CH$_2$—S—(CH$_2$)$_n$COOR4 where R4 represents H, alkyl, substituted alkyl, cycloalkyl, optionally substituted aryl, or optionally substituted heteroaryl and n is 1-4; —CH$_2$—S—(CH$_2$)$_n$—CH═CH$_2$ where n is 1-4; —CH$_2$—S—(CH$_2$)$_n$N—C(═NH)—NH$_2$ where n is 1-4. In each example given above, the sulphur may be oxidised to the sulfoxide or sulfone, and formulas can be represented as —CH$_2$—S(═O)$_m$—(CH$_2$)— where m is 0-2.

Further exemplary groups for Ra can be found in publication US2012/0088734, the contents of which are incorporated herein.

R$_b$ represents hydrogen or is absent where Ra is alkylene.

Exemplary compounds may include a compound of formula 1 wherein L is a chain of 1-6 carbon atoms, Q is a primary covalent bond or a carbonyl group and R1 and R2 are together with the nitrogen atom to which they are attached form a 4-7 membered aryl, cycloalkyl or heterocyclic ring which may be further fused or optionally substituted.

Exemplary compounds may include a compound of formula 1 wherein L is a chain of 1-6 carbon atoms, Q is a primary covalent bond or a carbonyl group and R1 and R2 are together with the nitrogen atom to which they are attached form a 5-7 membered cycloalkyl or heterocyclic ring which may be further fused or optionally substituted.

Exemplary compounds may include a compound of formula 1 wherein the group L-Q-NR1-R2 is selected from —(CH$_2$)$_n$—NR1R2 where n is 1-4 and R1 and R2 may independently represent H, alkyl, substituted alkyl or may together with the nitrogen atom to which they are attached form a 4-7 membered aryl, cycloalkyl or heterocyclic ring which may be further fused or optionally substituted.

Exemplary compounds may include a compound of formula 1 wherein the group L-Q-NR1-R2 is selected from —(CH$_2$)$_n$—S—(CH$_2$)$_m$—NR1R2 where n is 1-4, m is 1-4 and R1 and R2 may independently represent H, alkyl, substituted alkyl or may together with the nitrogen atom to which they are attached form a 4-7 membered aryl, cycloalkyl or heterocyclic ring which may be further fused or optionally substituted.

Exemplary compounds may include a compound of formula 1 wherein the group L-Q-NR1-R2 is selected from —(CH$_2$)$_n$—CO—NR1R2 where n is 1-4 and R1 and R2 may independently represent H, alkyl, substituted alkyl or may together with the nitrogen atom to which they are attached form a 4-7 membered aryl, cycloalkyl or heterocyclic ring which may be further fused or optionally substituted.

Exemplary compounds may include a compound of formula 1 wherein the group L-Q-NR1-R2 is selected from —(CH$_2$)$_n$—S—(CH$_2$)$_m$—CO—NR1R2 where n is 1-4, m is 1-4 and R1 and R2 may independently represent H, alkyl, substituted alkyl or may together with the nitrogen atom to which they are attached form a 4-7 membered aryl, cycloalkyl or heterocyclic ring which may be further fused or optionally substituted.

Exemplary structures for —NR1R2 include

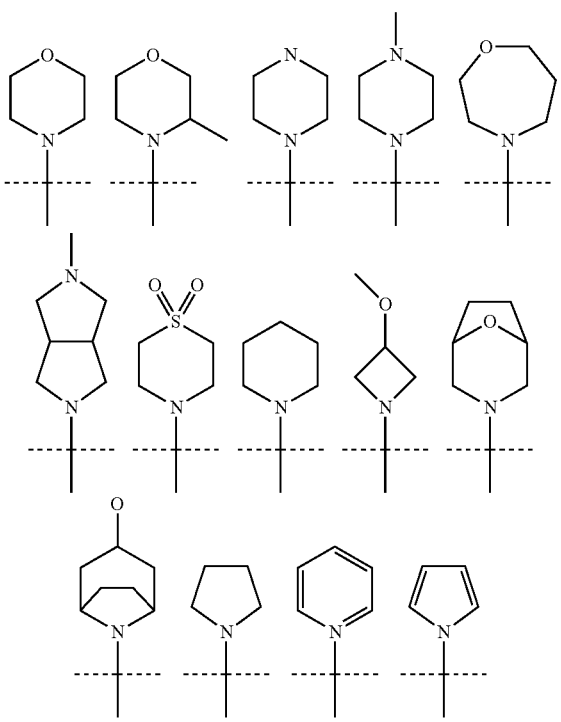

Exemplary compounds include a compound of formula 1 wherein L is a C1-6 alkyl group with 0-1 heteroatom substituents, and 0-1 double bonds, Q is a primary covalent bond and R1 and R2 are independently H, alkyl or substituted alkyl groups.

Exemplary compounds include a compound of formula 1 wherein L or Q is linked to R$_1$ to form a ring structure containing one or more nitrogen atoms.

Exemplary compounds may include a compound of formula 1 wherein the group L-Q-NR1-R2 is selected from —(CH$_2$)$_n$—NR1R2 where n is 1-4, R1 is H or alkyl, and R2 represents —COR$_3$, —CO$_2$R$_3$, —CONR$_4$R$_5$, —C(═NR$_6$)NR$_4$R$_5$, or —C(═NR$_6$)OR$_3$ where R3 represents alkyl, substituted alkyl, cycloalkyl, optionally substituted aryl, or optionally substituted heteroaryl, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, and R6 represents H, alkyl, substituted alkyl, cycloalkyl, optionally substituted aryl, or optionally substituted heteroaryl, Exemplary compounds may include a compound of formula 1 wherein the group L-Q-NR1-R2 is selected from —(CH$_2$)$_n$—S—(CH$_2$)$_m$—NR1R2 where n is 1-4, m is 1-4, R1 is H or alkyl, and R2 represents —COR$_3$, —CO$_2$R$_3$, —CONR$_4$R$_5$, —C(=NR$_6$)NR$_4$R$_5$, or —C(=NR$_6$)OR$_3$ where R3 represents alkyl, substituted alkyl, cycloalkyl, optionally substituted aryl, or optionally substituted heteroaryl, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, and R6 represents H, alkyl, substituted alkyl, cycloalkyl, optionally substituted aryl, or optionally substituted heteroaryl, Exemplary structures for N—COR$_3$, —CO$_2$R$_3$, —CONR$_4$R$_5$, —C(=NR$_6$)NR$_4$R$_5$, or —C(=NR$_6$)OR$_3$ include:

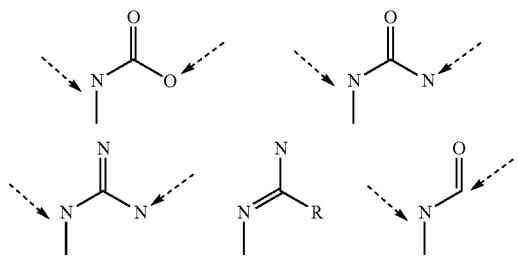

where the arrows indicated positions which can be further substituted. Groups may include

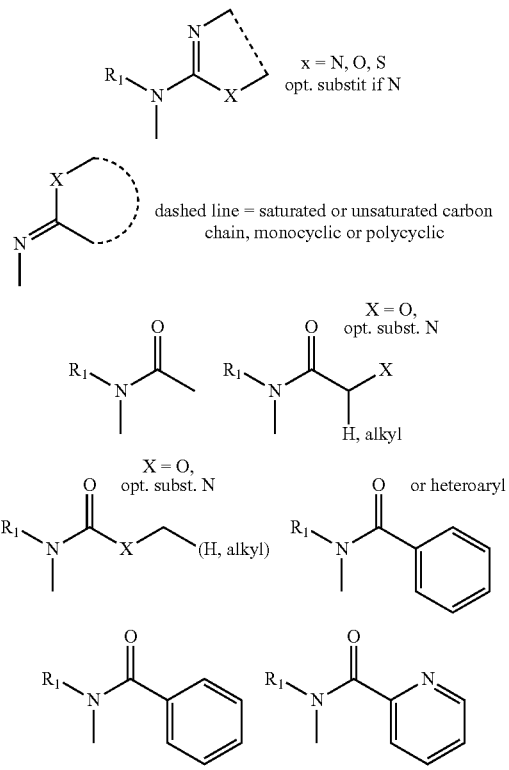

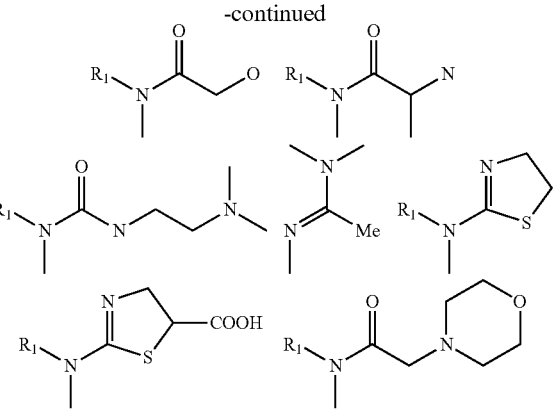

Exemplary compounds include a compound of formula 1 wherein Q is a secondary covalent bond, R1 is absent and R2 is —OR$_4$ or —NR$_4$R$_5$, where R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted.

Exemplary compounds include those shown below. In the diagram below, the L-Q-NR1-R2 group is depicted from the cyclic peptide ring.

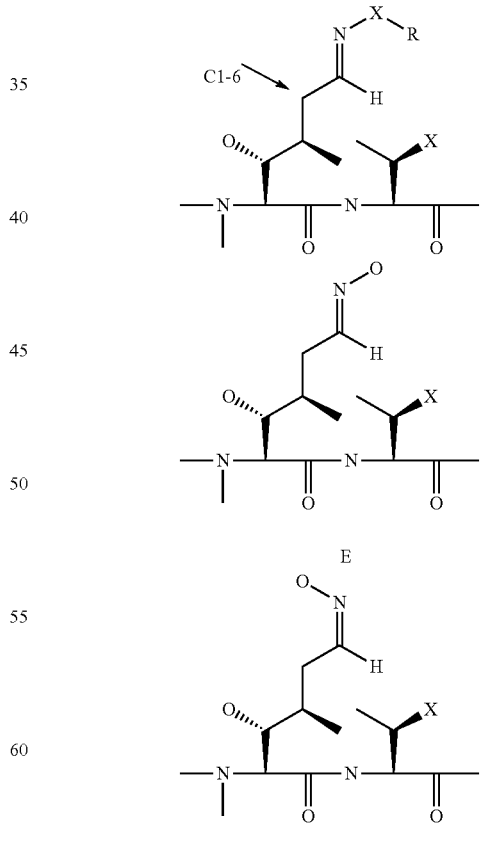

all derivatives of this series can have Z and E configuration;

15
only one (E) is shown below
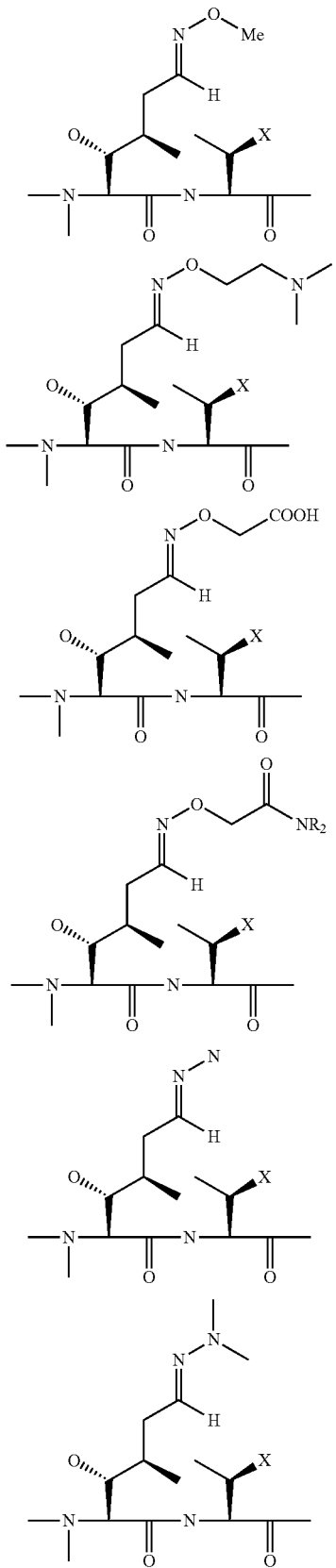
16
-continued
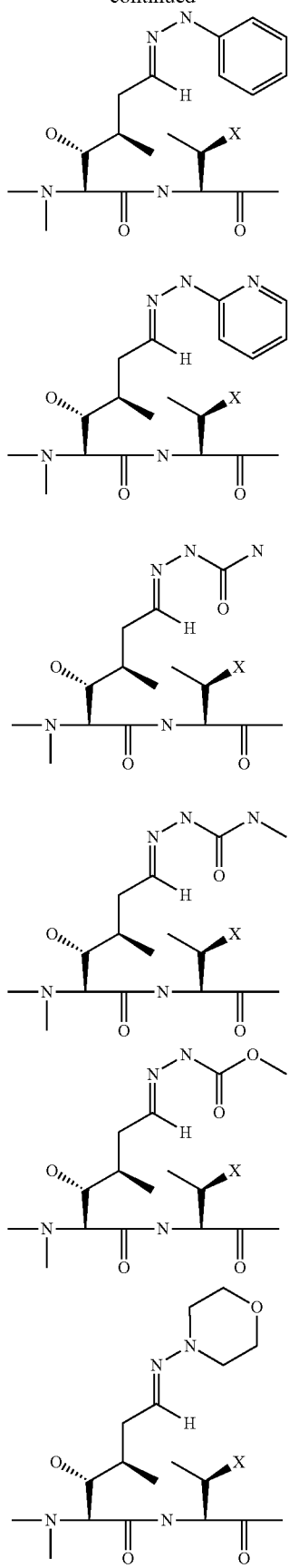

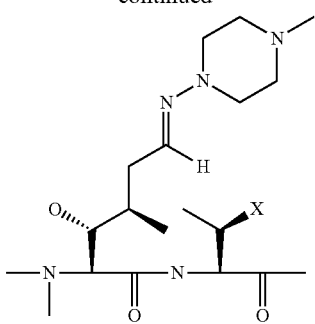
Exemplary amide structures of type CONR1R2 include
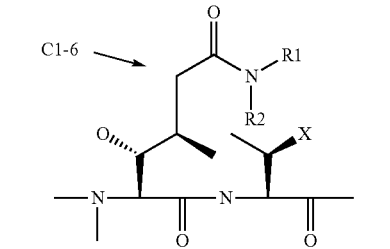
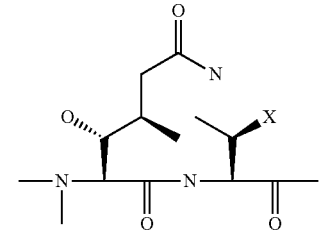
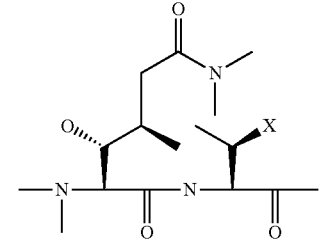
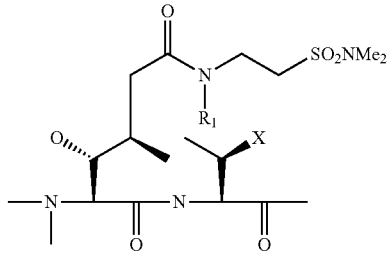
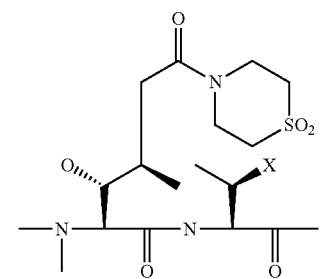
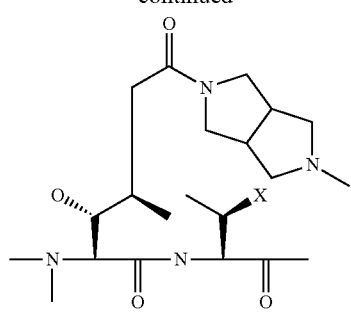
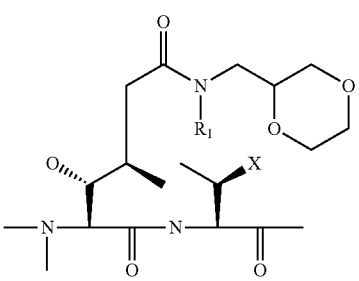
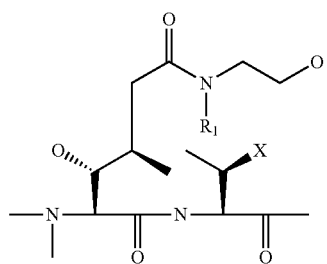
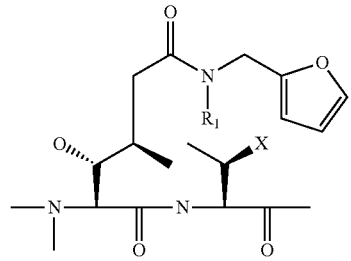
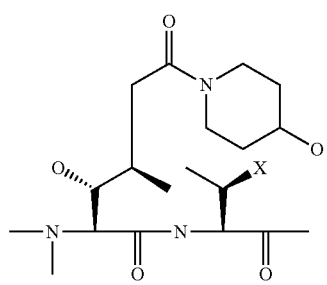
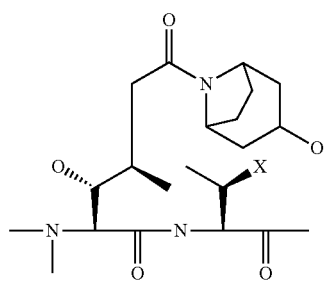

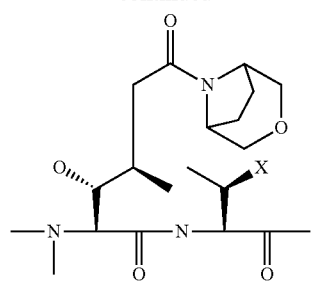
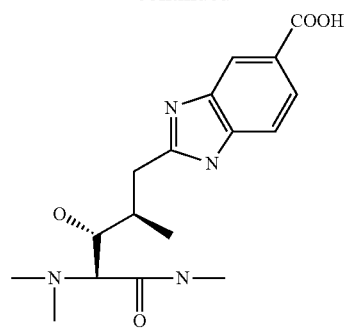
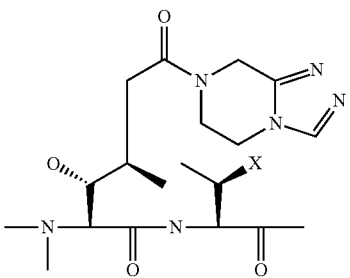
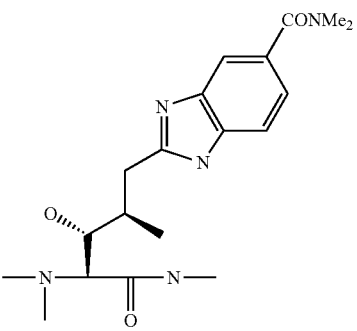
Examples of structures where L or Q are linked to R1 include:
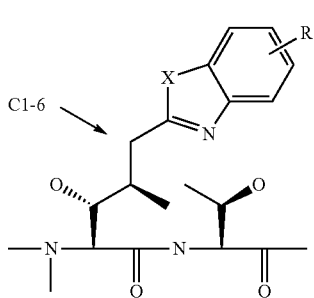
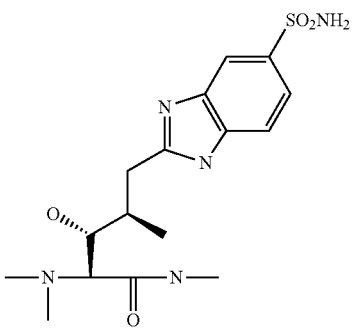
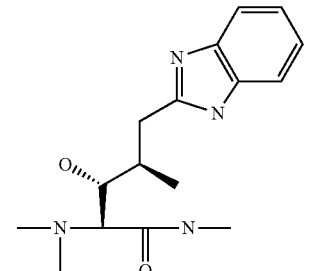
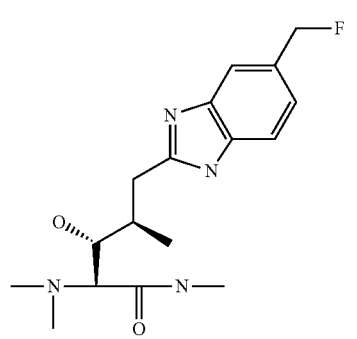
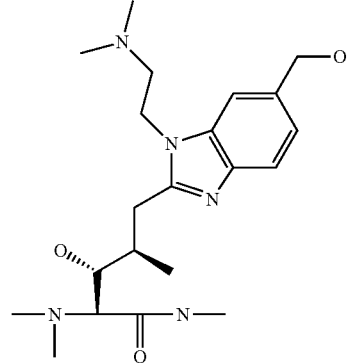
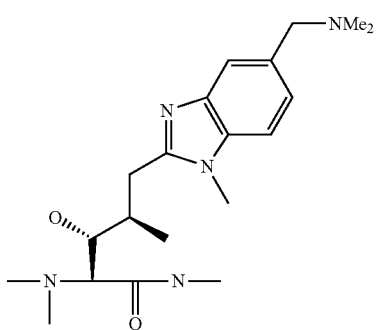

21

-continued

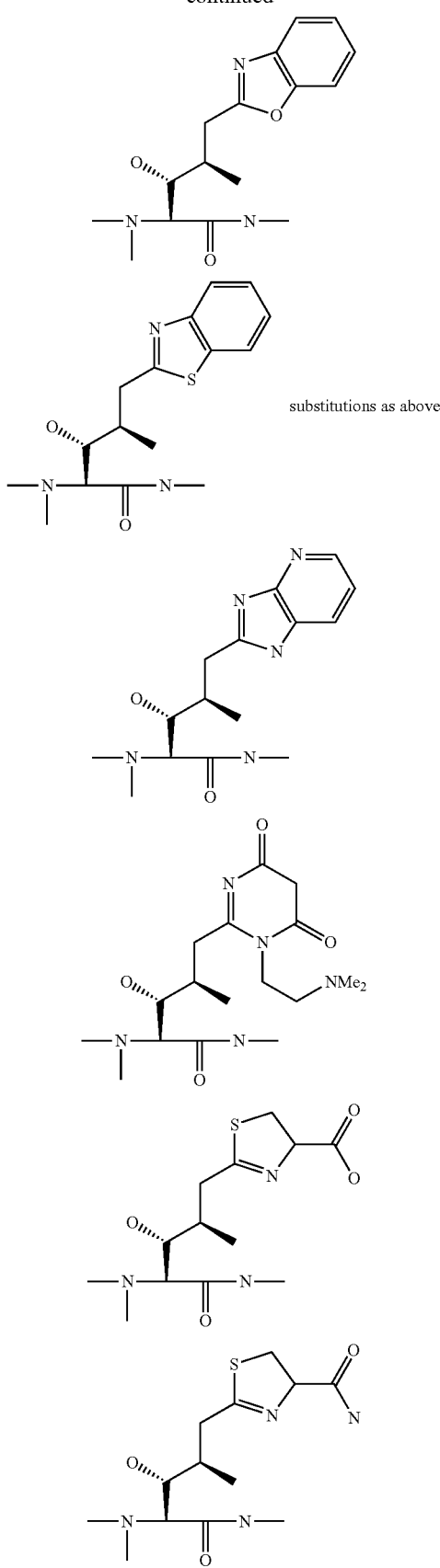

substitutions as above

22

-continued

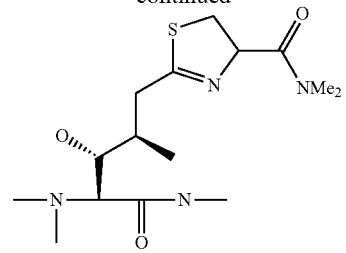

where R is one or more optional substituents on the aromatic ring.

Alternative structures are

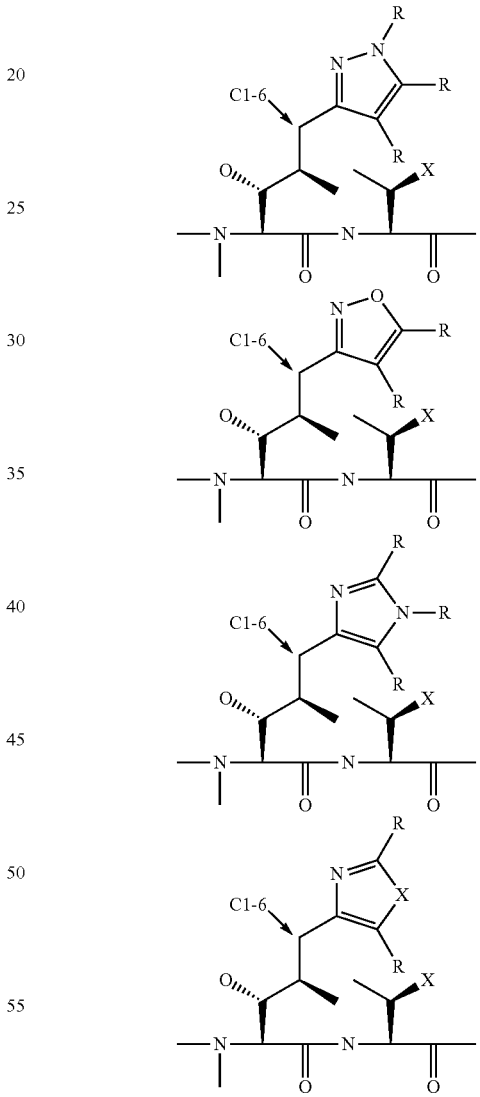

X = O or S where R is independently H, alkyl or substituted alkyl.

Alternative structures contain a ring containing one or more nitrogen atoms. The ring may be aromatic, as shown above. The ring may be an optionally substituted 6 membered aromatic ring. The ring may be a pyridyl or pyrazinyl ring. The ring may be of formula

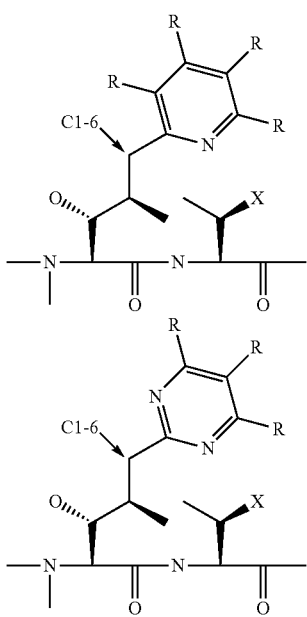

where R is independently H, alkyl or substituted alkyl.

In each of the C1-6 chains shown above, the chains can contain one or more double bonds. The chains can be $(CH_2)_n$ where n is 1-6 or can contain a CH=CH group as well as further $CH_2$ groups up to a total of 6 carbon atoms.

The compound may be according to the formula

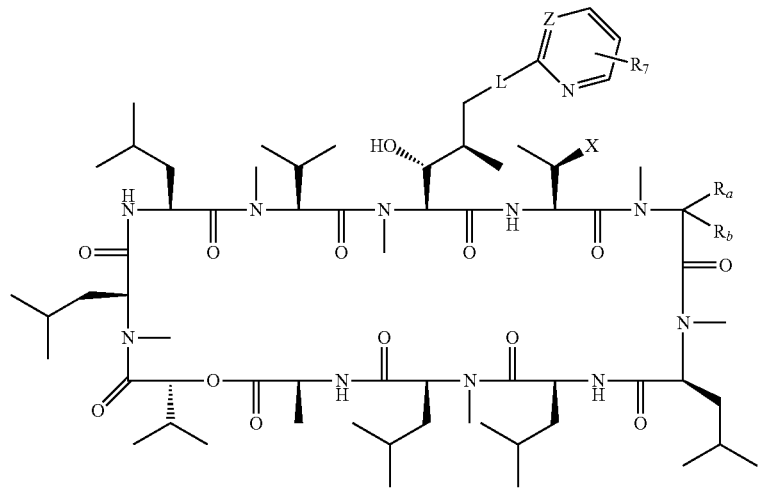

or a pharmaceutically acceptable salt, tautomer or N-oxide thereof, wherein

L represents a bond or an optionally substituted, optionally partially unsaturated chain of 1-6 carbon atoms with optional additional heteroatoms atoms in the chain, and may be optionally branched, Z represents N or CH, R7 represents H, optionally substituted alkyl, NH2, heterocycloalkyl, $—NR_4R_5$, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted X represents H, OH, OC(=O)-alkyl, OC(=O)-substituted alkyl, O-alkyl, O-substituted alkyl, carbonyl (=O) or imine (=N—Y) where Y is $—OR_4$ or $—NR_4R_5$, $R_a$ represents hydrogen, alkyl, substituted alkyl, alkoxy, substituted alkoxy, alkylthio, substituted alkylthio or optionally substituted alkylene, and $R_b$ represents hydrogen or is absent, R7 may be at any position of the pyridyl or pyrazyl group. R7 may be H, methyl, or morpholinyl.

The disclosures herein include any pharmaceutically acceptable salts. Where compounds are isomers, all chiral forms and racemates are included. The disclosures include all solvates, hydrates and crystal forms.

To the extent that any of the compounds described have chiral centres, the present invention extends to all isomers of such compounds, whether in the form of diastereomeric mixtures or or separated diastereomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium or organic bases such as ethanolamine, N,N-dialkylethanolamines, morpholine, etc.

Examples of acid addition salts include acid addition salts formed with acetic, 2,2-dichloroacetic, citric, lactic, mandelic, glycolic, adipic, alginic, aryl sulfonic acids (e.g., benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic acids; and from metals such as sodium, magnesium, or preferably, potassium and calcium.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Definitions

Amino

Amino means $NH_2$. Amino includes substituted amino. Substituted amino means $NHR$ or $NR^2R^3$ where $R^2$ and $R^3$ are independent substituents or where $NR^2R^3$ forms an optionally substituted 4 to 7 membered non-aromatic heterocyclic ring optionally containing a second heteroatom ring member selected from O, N and S and oxidised forms thereof. Exemplary substituted amino groups include $NMe_2$, $NEt_2$, piperidinyl, piperazinyl, morpholino, N-cyclohexyl, where the rings may be further substituted.

Alkyl

Alkyl means an aliphatic hydrocarbon group. The alkyl group may be straight or branched or cyclic. "Branched" means that at least one carbon branch point is present in the group. Thus, for example, tert-butyl and isopropyl are both branched groups. The alkyl group may be a lower alkyl group. "Lower alkyl" means an alkyl group, straight or branched, having 1 to about 6 carbon atoms, e.g. 2, 3, 4, 5 or 6 carbon atoms.

Exemplary alkyl groups include methyl, ethyl, n-propyl, i-propyl, n-butyl, t-butyl, s-butyl, n-pentyl, 2-pentyl, 3-pentyl, n-hexyl, 2-hexyl, 3-hexyl, n-heptyl, 2-heptyl, 3-heptyl, 4-heptyl, 2-methyl-but-1-yl, 2-methyl-but-3-yl, 2-methyl-pent-1-yl, 2-methyl-pent-3-yl.

The alkyl group may be optionally substituted, e.g. as exemplified below. The term alkyl also includes aliphatic hydrocarbon groups such as alkenyl, and alkylidene and cycloalkyl, cycloalkylidene, heterocycloalkyl and heterocycloalkylidene groups, which may be further substituted.

Alkenyl

Alkenyl means an unsaturated aliphatic hydrocarbon group. The unsaturation may include one or more double bond, one or more triple bond or any combination thereof. The alkenyl group may be straight or branched. "Branched" means that at least one carbon branch point is present in the group. Any double bond may, independently of any other double bond in the group, be in either the (E) or the (Z) configuration.

The alkenyl group may be a lower alkenyl group. "Lower alkenyl" means an alkenyl group, straight or branched, having 2 to 6 carbon atoms, e.g. 2, 3, 4, 5 or 6 carbon atoms. Exemplary alkenyl groups include ethenyl, n-propenyl, i-propenyl, but-1-en-1-yl, but-2-en-1-yl, but-3-en-1-yl, pent-1-en-1-yl, pent-2-en-1-yl, pent-3-en-1-yl, pent-4-en-1-yl, pent-1-en-2-yl, pent-2-en-2-yl, pent-3-en-2-yl, pent-4-en-2-yl, pent-1-en-3-yl, pent-2-en-3-yl, pentadien-1-yl, pentadien-2-yl, pentadien-3-yl. Where alternative (E) and (Z) forms are possible, each is to be considered as individually identified. The alkenyl group may be optionally substituted, e.g. as exemplified below. Alkenyl includes cyano.

Alkylidene

Alkylidene means any alkyl or alkenyl group linked to the remainder of the molecule via a double bond. The definitions and illustrations provided herein for alkyl and alkenyl groups apply with appropriate modification also to alkylidene groups.

Alkylthio

Alkylthio means any alkyl group containing a sulfur atom in the carbon chain. The sulphur atom may be in the form of a thioether (C—S—C), a sulfoxide (C—S(=O)—C) or sulfone (C—S(=O)$_2$—C). Alkylthio groups may be further substituted. Alkylthio groups include $CH_2$—S—R where R is a further alkyl, cycloalkyl or substituted alkyl group.

Cycloalkyl

Cycloalkyl means a cyclic non-aromatic hydrocarbon group. The cycloalkyl group may include non-aromatic unsaturation. The cycloalkyl group may have 3 to 6 carbon atoms, e.g. 3, 4, 5 or 6 carbon atoms. Exemplary cycloalkyl groups include cyclopropyl, cyclobutyl, cyclopentyl, cyclohexyl, cyclopentenyl, cyclohexenyl.

The cycloalkyl group may be optionally substituted, as defined below, e.g. as exemplified below. Exemplary substituted cycloalkyl groups include mono- or poly-alkyl-substituted cycloalkyl groups such as 1-methylcyclopropyl, 1-methylcyclobutyl, 1-methylcyclopentyl, 1-methylcyclohexyl, 2-methylcyclopropyl, 2-methylcyclobutyl, 2-methylcyclopentyl, 2-methylcyclohexyl, 1,2-dimethylcyclohexyl or 1,3-dimethylcyclohexyl.

Cycloalkylidene Group

Cycloalkylidene means any cycloalkyl group linked to the remainder of the molecule via a double bond. The definitions and illustrations provided herein for cycloalkyl groups apply with appropriate modification also to cycloalkylidene groups.

Heterocycloalkyl

Heterocycloalkyl group means a non-aromatic cyclic group which contains one or more heteroatoms in the ring. The heterocycloalkyl group may contain O, N or S atoms. The heterocycloalkyl group may be fully saturated or partially unsaturated. The heterocycloalkyl group is typically monocyclic or bicyclic, and more usually is monocyclic.

Exemplary heterocycloalkyl groups include azetidinyl, pyrrolidinyl, piperidinyl, azepinyl, diazepinyl, dihydrofuranyl (e.g. 2,3-dihydrofuranyl, 2,5-dihydrofuranyl), 4,5-dihydro-1H-maleimido, dioxolanyl, 2-imidazolinyl, imidazolidinyl, isoxazolidinyl, morpholinyl, oxazolidinyl, piperazinyl, pyrrolidinonyl, 2-pyrrolinyl, 3-pyrrolinyl, sulfolanyl, 3-sulfolenyl, tetrahydrofuranyl, thiomorpholinyl, dihydropyranyl (e.g. 3,4-dihydropyranyl, 3,6-dihydropyranyl), dioxanyl, hexahydropyrimidinyl, 2-pyrazolinyl, pyrazolidinyl, pyridazinyl, 4H-quinolizinyl, quinuclinyl, tetrahydropyranyl, 3,4,5,6-tetrahydropyridinyl, 1,2,3,4-tetrahydropyrimidinyl, 3,4,5,6-tetrahydropyrimidinyl, tetrahydrothiophenyl, tetramethylenesulfoxide, thiazolidinyl, 1,3,5-triazinanyl, 1,2,4-triazinanyl, hydantoinyl, and the like. The point of attachment may be via any atom of the ring system.

Heterocycloalkylidene Group

Heterocycloalkylidene means any heterocycloalkyl group linked to the remainder of the molecule via a double bond. The definitions and illustrations provided herein for heterocycloalkyl groups apply with appropriate modification also to heterocycloalkylidene groups.

Optionally Substituted

"Optionally substituted" as applied to any group means that the said group may if desired be substituted with one or more substituents, which may be the same or different. 'Optionally substituted alkyl' includes both 'alkyl' and 'substituted alkyl'.

Examples of suitable substituents for "substituted" and "optionally substituted" moieties include halo (fluoro, chloro, bromo or iodo), $C_{1-6}$ alkyl, $C_{3-6}$ cycloalkyl, hydroxy, $C_{1-6}$ alkoxy, cyano, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{1-6}$ aryl, $C_{1-6}$ arylamino, $C_{1-6}$ aroylamino, benzylamino, $C_{1-6}$ arylamido, carboxy, $C_{1-6}$ alkoxycarbonyl or ($C_{1-6}$ aryl)($C_{1-10}$ alkoxy)carbonyl, carbamoyl, mono-$C_{1-6}$ carbamoyl, di-$C_{1-6}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl. In groups containing an oxygen atom such as hydroxy and alkoxy, the oxygen atom can be replaced with sulphur to make groups such as thio (SH) and thio-alkyl (S-alkyl). Optional substituents therefore includes groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Substitution may take the form of double bonds, and may include heteroatoms. Thus an alkyl group with a carbonyl (C=O) instead of a $CH_2$ can be considered a substituted alkyl group.

Substituted groups thus include for example $CFH_2$, $CF_2H$, $CF_3$, $CH_2NH_2$, $CH_2OH$, $CH_2CN$, $CH_2SCH_3$, $CH_2OCH_3$, OMe, OEt, Me, Et, —$OCH_2O$—, $CO_2Me$, C(O)Me, i-Pr, $SCF_3$, $SO_2Me$, $NMe_2$, $CONH_2$, $CONMe_2$ etc. In the case of aryl groups, the substitutions may be in the form of rings from adjacent carbon atoms in the aryl ring, for example cyclic acetals such as O—$CH_2$—O.

The term optionally substituted includes groups containing both alkyl are aryl moieties such as benzyl, CH2-pyridyl or any other group having a ring attached to an alkyl group. Thus optionally substituted includes $CH_2$-ring or $CH_2$—$CH_2$-ring.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The term "pharmaceutical formulation" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents including liposomes or nanoparticulates, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The formulations include but are not limited to those suitable for the administration routes described herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

Tablets may optionally be coated or scored and optionally are formulated so as to provide slow or controlled release of the active ingredient. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more colouring agents, one or more flavouring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavouring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above.

Additional excipients, for example sweetening, flavouring and colouring agents, may also be present.

The pharmaceutical compositions of the invention may also be in the form of oil-in-water emulsions. The oily phase may be a vegetable oil, such as olive oil, castor oil or arachis oil, a long or medium chain triglyceride, a mineral oil, such as liquid paraffin, or a mixture of these. Suitable emulsifying agents include naturally-occurring gums, such as gum acacia and gum tragacanth, naturally occurring phosphatides, such as soybean, phosphatidyl choline, glycerol, lecithin, esters or partial esters or salts derived from fatty acids and hexitol anhydrides, such as sorbitan monooleate, and condensation products of these partial esters with ethylene oxide, polyoxyethylene sorbitan monooleate, or a polyethoxylated castor oil such as Kolliphor EL, formerly known as Cremophor EL®. The emulsion may also contain sweetening and flavouring agents. Syrups and elixirs may be formulated with sweetening agents, such as glycerol, sorbitol or sucrose. Such formulations may also contain a demulcent, a preservative, flavouring or a colouring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof of the active ingredient.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 0.1 mg to about 100 mg per kg body weight of a human and non-human animal, preferably from about 1 mg to about 50 mg per kg of body weight of a human and non-human animal, and most preferably from about 3 mg to about 30 mg per kg of body weight of a human and non-human animal.

One or more compounds of the present invention may be administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient.

In another embodiment, the compounds of the present invention may be combined with one or more active agents, e.g. each at a therapeutic concentration as reported in the art. Non-limiting examples of suitable combinations include combinations of one or more compounds of the present invention with at least one or two or more compounds or a pharmaceutically acceptable salt thereof selected from one or more of the following groups.

(i) Cyclooxygenase inhibitors e.g. Aspirin;
(ii) Calcium channel antagonists e.g. Nifedipine (Adalat), Nicardipine (Cardene), Diltiazem (Tildiem);
(iii) Potassium channel activators (K+ATP) e.g. Nicorandil;
(iv) Compounds that acts by generating nitric oxide (NO), NO donors or compounds that enhance NO release e.g. Nitrates;
(v) Angiotensin II receptor agonists e.g. Losartan (Cozaar);
(vi) Angiotensin converting enzyme (ACE) inhibitors e.g. Enalapril (Vasotec/Renitec);
(vii) Dual angiotensin converting enzyme/neutral peptidase inhibitors (ACE/NEP);
(viii) Neutral peptidase inhibitors (NEP);
(ix) Endothelin antagonists of the ET-A and/or ET-B receptors e.g. Bostentan (Tracleer);
(x) Renin inhibitors e.g. Aliskiren (Tekturna);
(xi) Adenosine diphosphate (ADP) inhibitors and/or P2Y12 receptor inhibitors e.g. Clopidogrel (Plavix);
(xii) Tissue plasminogen activators (e.g. Reteplase);
(xiii) Phosphodiesterase inhibitors e.g. Cilostazol (Pletal);
(xiv) Glycoprotein IIB/IIIA (integrin αIIbβ3) inhibitora e.g. murine-human chimeric antibodies e.g. Abciximab (ReoPro), Eptifibatide (Integrilin) and/or synthetic peptides (e.g., Eptifibatide) and/or synthetic non-peptides e.g., Tirofiban (Aggrastat);
(xv) Adenosine reuptake inhibitor e.g. Dipyridamole (Persantine);

(xvi) Thromboxane inhibitors and/or thromboxane synthase inhibitors and/or thromboxane receptor antagonists e.g. Terutroban;
(xvii) Prostacyclins e.g. Epoprostenol (Flolan);
(xviii) Aldosterone receptor antagonists e.g Eplerinone (Inspra);
(xix) Plasminogen activators (PA), e.g. Alteplase and Tenecteplase;
(xx) Cholesterylester transfer protein inhibitors;
(xxi) Mevalonate decarboxylase antagonists (e.g., Hymeglusin), and/or a squalene synthesis inhibitors (e.g., Zaragozic acid) and/or an HMG-CoA reductase inhibitor/statin e.g. Atorvastatin (Lipitor);
(xxii) Calcium Channel blockers (CCB) e.g. Nifedipine (Procardia);
(xxiii) Beta adrenergic blocker e.g. Propranolol (Inderal LA);
(xxiv) An alpha adrenergic blockers e.g. Doxazosin (Cardura);
(xxv) ApoA-I mimics;
(xxvi) Na+/K+-ATPase membrane pump inhibitors;
(xxvii) Inotropic agents;
(xxviii) Anti-fibrotic agents, e.g., Amiloride;
(xxix) Anticoagulant agent agents e.g. Warfarin (Coumadin);
(xxx) Compounds that protect against cellular and/or mitochondrial oxidative damage by e.g. reactive oxygen species (ROS) e.g. Mito-Q, Vitamin E;
(xxxi) A compound that enhances or facilitates or up-regulates mitochondrial respiration e.g. Coenzyme Q10 mimics, Resveratrol;
(xxxii) An anti-diabetic agent e.g. Metformin and/or a PPAR modulator e.g. Rosiglitazone;
(xxxiii) Interferons, e.g., pegylated rIFN-alpha 2b (PEG-Intron);
(xxxiv) Ribavirin and its analogs, e.g. Ribavirin (Rebetol, Copegus), and Taribavirin (Viramidine);
(xxxv) HCV NS3 protease inhibitors, e.g. Boceprevir, Telaprevir;
(xxxvi) Alpha-glucosidase 1 inhibitors, e.g. Celgosivir, Miglitol;
(xxxvii) Hepatoprotectants, e.g. Emericasan,
(xxxviii) Nucleoside or nucleotide inhibitors of HCV NS5B polymerase e.g. Valopicitabine;
(xxxix) Non-nucleoside inhibitors of HCV NS5B polymerase, e.g., Filibuvir;
(xl) HCV NS5A inhibitors, e.g. BMS-790052;
(xli) TLR-7 agonists, e.g., Imiquimod;
(xlii) Cyclophillin inhibitors, e.g, DEBIO-025, SCY-635, and NIM811;
(xliii) HCV IRES inhibitors, e.g, MCI-067;
(xliv) Entry or fusion inhibitors e.g. CCR5 receptor antagonists e.g. Marovirac; e.g. HIV fusion inhibitors e.g. Enfuvirtide (Fusion);
(xlv) Nucleoside analoge reverse-transcriptase inhibitors (NARTIs or NRTIs) e.g. Zidovudine (AZT), Emtricitabine;
(xlvi) Nucleotide analogue reverse-transcriptase inhibitors (NtARTIs or NtRTIs) e.g. Tenofovir (Viriad);
(xlvii) Non-nucleoside reverse-transcriptase inhibitors (NNRTIs) e.g. Efavirenz (Sustiva);
(xlviii) Integrase strand transfer inhibitors (Integrase inhibitors) e.g. Elvitegravir;
(xlix) Protease inhibitors e.g. Saquinavir, Ritonavir;
(l) Other drugs for treating HIV and HCV viral infections infections, e.g. Thymosin alpha 1 (Zadaxin), Nitazoxanide;
(li) Pharmacokinetic enhancers;
(lii) Beta-adrenergic agonists e.g. Salmeterol, Salbutamol;
(liii) Anti-cholinergic agents (muscarinic) e.g. Tiotropium;
(liv) Methyxanthines e.g. Theophyllin);
(lv) Corticosteroids e.g. Dexamethasone, Budesonide, Prednsione;
(lvi) Vitamin D analogues e.g. Calcipotriol, Calcitriol;
(lvii) Retinoids e.g. Acitretin;
(lviii) Immunosuppressants e.g. Adalimumab, Etanercept, Methotrexate;
(lix) Reversible Acetylcholinesterase inhibitors e.g. Donepezile (Aracept), Rivastigmine (Exelon) and Galantamine (Reminyl);
(lx) Other anticholinergics e.g. Orphenadrine (Biorphen), Procyclidine (Arpicolin) Trihexyphenidyl (Broflex);
(lxi) N-methyl-D-aspartate receptor (NMDA receptor) antagonists (glutamate site) e.g. Memantine (Abixa);
(lxii) NMDA receptor antagonists (glycine site) e.g. Gavestinel;
(lxiii) Indirect NMDA receptor antagonists e.g. Lubeluzole (Prosynap);
(lxiv) L-DOPA (Levodopa);
(lxv) Dopamine Agonists e.g. bromocriptine (Parlodel), Cabergoline (Cabaser) pergolide, Pramipexole (Mirapexin), Apomorphine (Apo-GO);
(lxvi) Glutamate antagonists e.g. Amantadine (Symmetrel); Selfotel
(lxvii) Inhibitors of Catachol-O-Methyl-Transferase (COMT) e.g. Entacapone (Comtess) Tolcapone (Tasmar);
(lxviii) Monoamine oxidase inhibitors e.g Rasagiline (Azilect), Selegiline (Eldepryl, Zelapar);
(lxix) Sodium channel blockers e.g. Riluzole (Rilutek);
(lxx) Gamma-aminobutyric acid (GABA) agonists e.g. Piracetam (Nootropil), Clomethiazole;
(lxxi) Lipid peroxidation inhibitors e.g. Tirilazad;
(lxxii) Nootropic agents e.g. Citicholine
(lxxiii) Estrogen receptor antagonists e.g. Tamoxifen;
(lxxiv) Aromatase inhibitors e.g Anastrozole;
(lxxv) DNA alkylating agents e.g. Cyclophosphamide;
(lxxvi) DNA intercalating agents e.g. Anthracyclines e.g Doxorubicin, Epirubicin;
(lxxvii) Anti-mitotic agents e.g. Docetaxel, Paclitaxel;
(lxxviii) Thymidylate Synthase inhibitors e.g. 5-Flurouracil (5FU);
(lxxix) Antifolates e.g Methotrexate;
(lxxx) Topoisomerase inhibitors e.g. Topotecan (Hycamtin), Irinotecan;
(lxxxi) Platinum containing anti-neoplastic agents e.g. Cisplatin (Platin), Carboplatin (Paraplatin), Oxaliplatin;
(lxxxii) Inhibitors of microtubule formation e.g. Vincristine (Oncovin), Vinblastine;
(lxxxiii) BCR-Abl Inhibitors e.g. Imatibib (Gleevec);
(lxxxiv) Inhibitors of HER2 expression e.g. Trastuzumab (Herceptin);

A combination therapy described herein may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Specific (non-limiting) examples of compounds include

| Structure | Patent Example No. | Name |
|---|---|---|
| 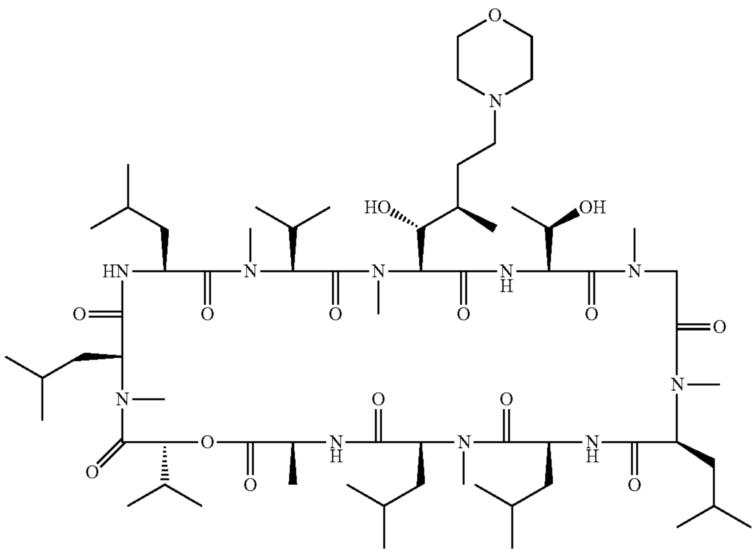 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCOCC2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 2 | cyclo-[(3R,4R,5S)-4-(hydroxy)-3-methyl-5-(methylamino)-1-N-morpholino-hexanoic acid-Thr-Sar-MeLeu-Leu-MeLeu-Ala-D-Hiv-MeLeu-Leu-MeVal] |
| 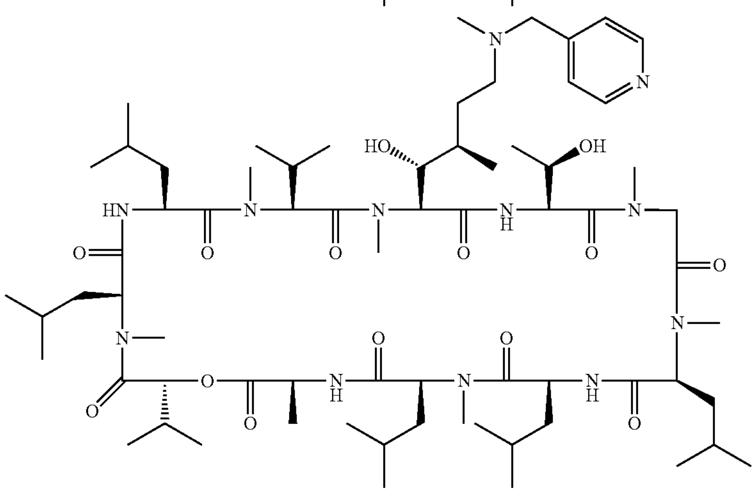 | 3 | cyclo-[(3R,4R,5S)-4-(hydroxy)-3-methyl-5-(methylamino)-1-N-(methyl-pyridin-4-ylmethyl-amino)-hexanoic acid-Thr-Sar-MeLeu-Leu-MeLeu-Ala-D-Hiv-MeLeu-Leu-MeVal] |
| 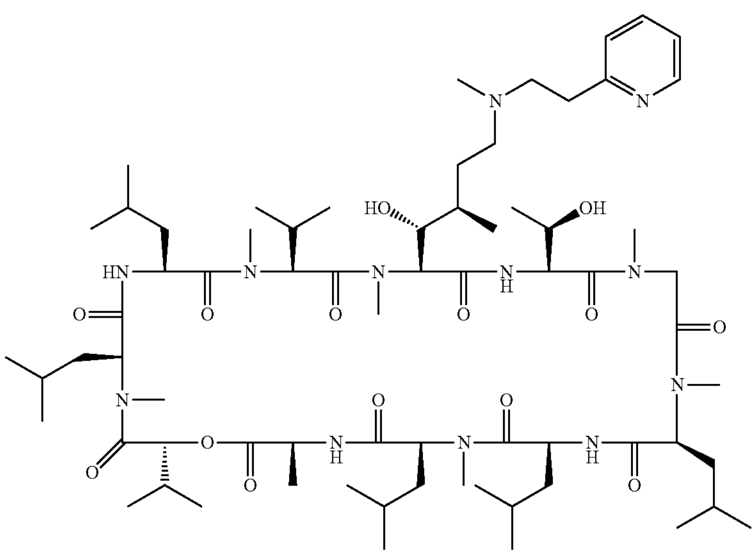 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)CCc2ccccn2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 4 | cyclo-{(3R,4R,5S)-4-(hydroxy)-3-methyl-5-(methylamino)-1-N-[methyl-2-(pyridin-2-yl)-ethyl-amino]-hexanoic acid-Thr-Sar-MeLeu-Leu-MeLeu-Ala-D-Hiv-MeLeu-Leu-MeVal} |

| Structure | Patent Example No. | Name |
|---|---|---|
| 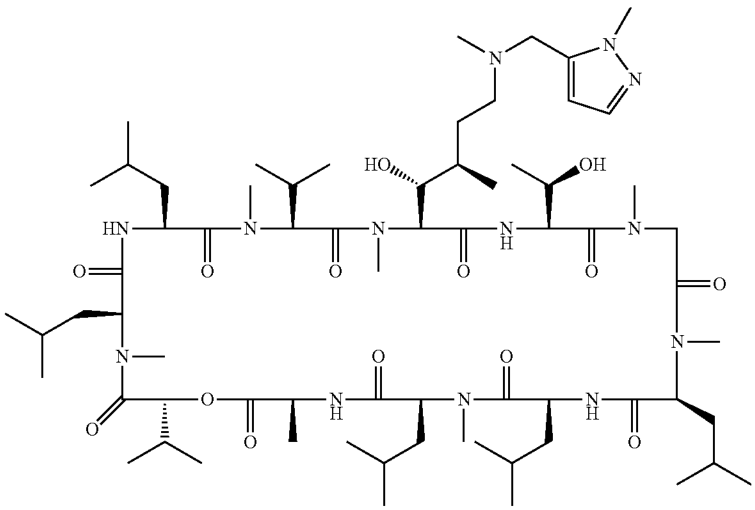 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)Cc2ccnn2C)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 5 | cyclo-{(3R,4R,5S)-4-(hydroxy)-3-methyl-5-(methylamino)-1-N-[methyl-(2-methyl-2H-pyrazol-3-ylmethyl)-amino]-hexanoic acid-Thr-Sar-MeLeu-Leu-MeLeu-Ala-D-Hiv-MeLeu-Leu-MeVal} |
| 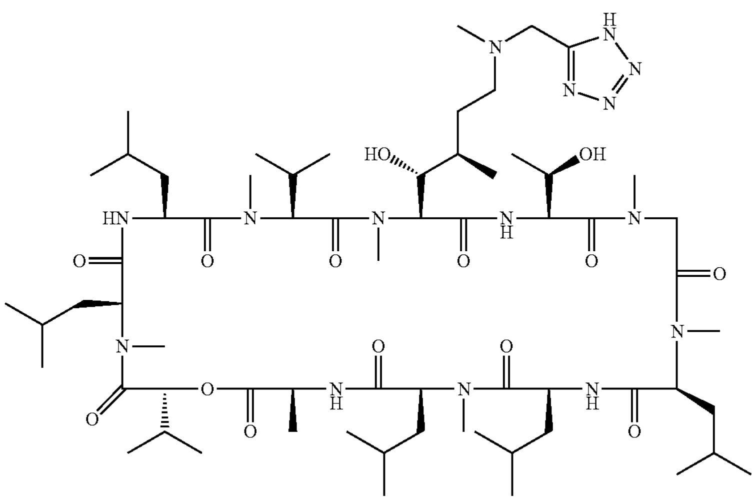 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)Cc2nnn[nH]2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 6 | cyclo-{(3R,4R,5S)-4-(hydroxy)-3-methyl-5-(methylamino)-1-N-[methyl-(1H-tetrazol-5-ylmethyl)-amino]-hexanoic acid-Thr-Sar-MeLeu-Leu-MeLeu-Ala-D-Hiv-MeLeu-Leu-MeVal} |
| 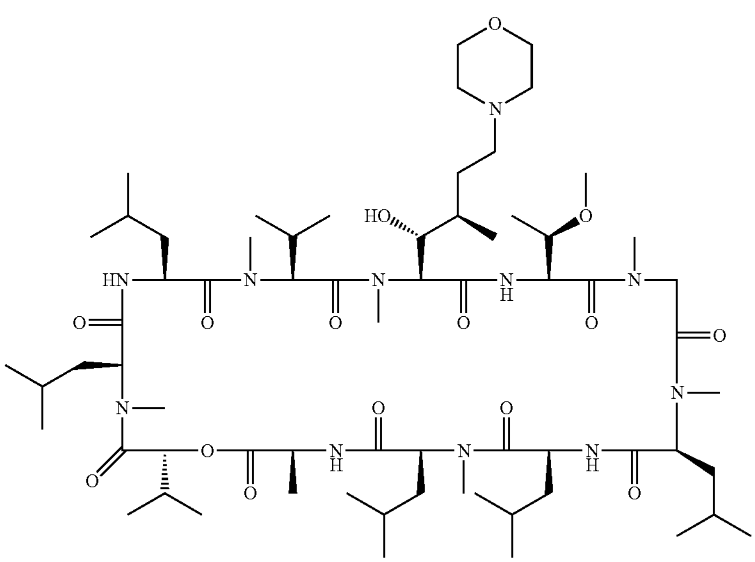 [SMILES: CO[C@H](C)[C@H]1NC(=O)[C@@H]([C@H](O)[C@H](C)CCN2CCOCC2)N(C)C(=O)[C@@H](C(C)C)N(C)C(=O)[C@@H](CC(C)C)NC(=O)[C@@H](CC(C)C)N(C)C(=O)[C@H](C(C)C)OC(=O)[C@@H](C)NC(=O)[C@@H](CC(C)C)N(C)C(=O)[C@@H](CC(C)C)NC(=O)[C@H](CC(C)C)N(C)C(=O)CN(C)C1=O] | 7 | cyclo-[(3R,4R,5S)-4-(hydroxy)-3-methyl-5-(methylamino)-1-N-morpholino-hexanoic acid-(O-methyl-Thr)-Sar-MeLeu-Leu-MeLeu-Ala-D-Hiv-MeLeu-Leu-MeVal] |

| Structure | Patent Example No. | Name |
|---|---|---|
| 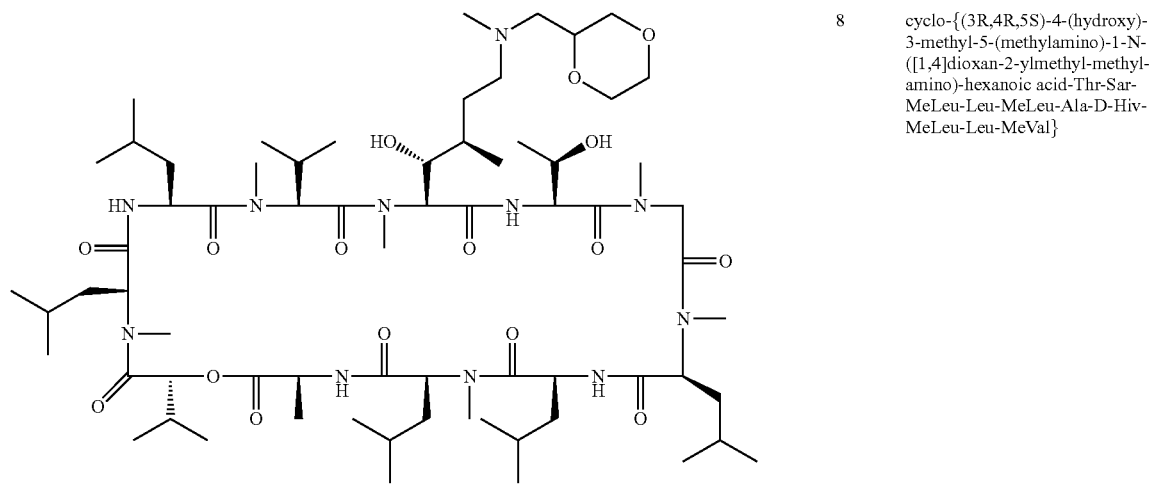 | 8 | cyclo-{(3R,4R,5S)-4-(hydroxy)-3-methyl-5-(methylamino)-1-N-([1,4]dioxan-2-ylmethyl-methyl-amino)-hexanoic acid-Thr-Sar-MeLeu-Leu-MeLeu-Ala-D-Hiv-MeLeu-Leu-MeVal} |
| 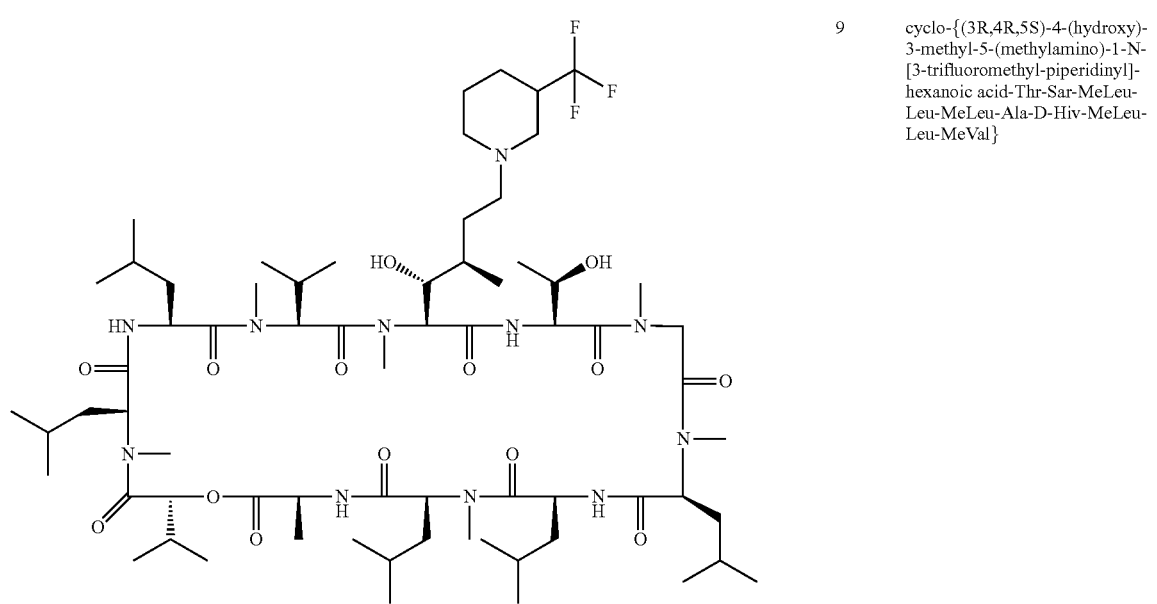 | 9 | cyclo-{(3R,4R,5S)-4-(hydroxy)-3-methyl-5-(methylamino)-1-N-[3-trifluoromethyl-piperidinyl]-hexanoic acid-Thr-Sar-MeLeu-Leu-MeLeu-Ala-D-Hiv-MeLeu-Leu-MeVal} |

-continued
| Structure | Patent Example No. | Name |
|---|---|---|
| 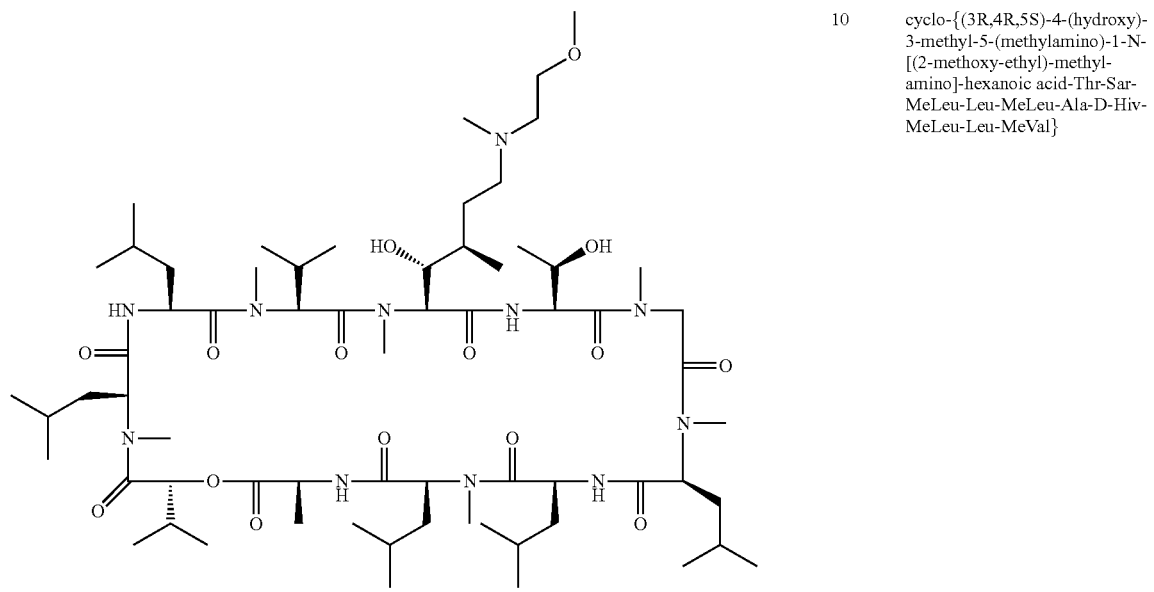 | 10 | cyclo-{(3R,4R,5S)-4-(hydroxy)-3-methyl-5-(methylamino)-1-N-[(2-methoxy-ethyl)-methyl-amino]-hexanoic acid-Thr-Sar-MeLeu-Leu-MeLeu-Ala-D-Hiv-MeLeu-Leu-MeVal} |
| 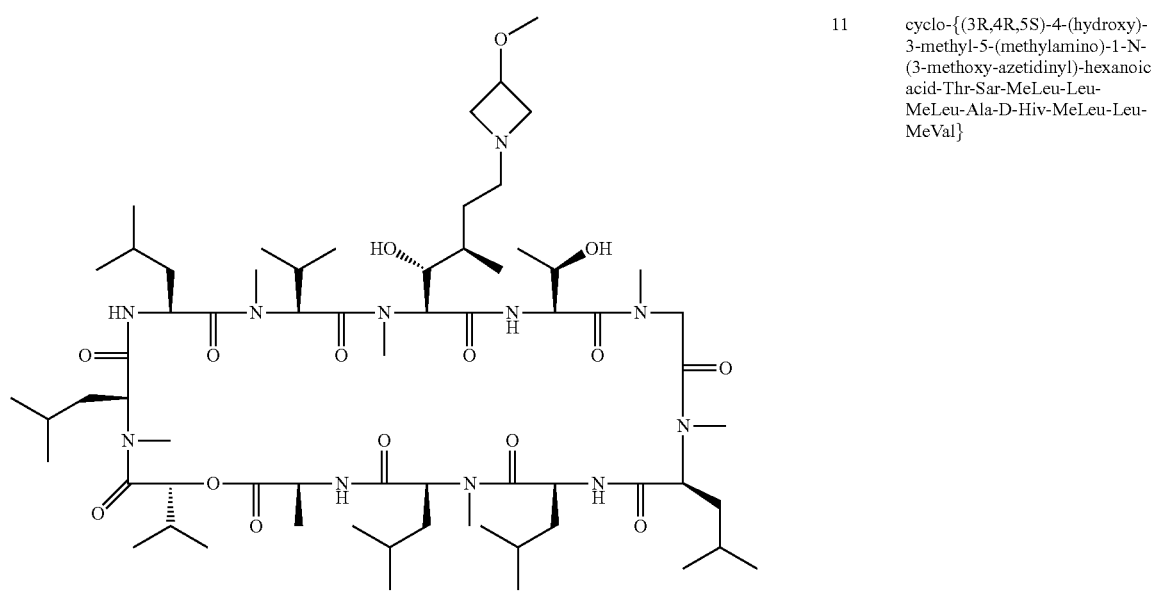 | 11 | cyclo-{(3R,4R,5S)-4-(hydroxy)-3-methyl-5-(methylamino)-1-N-(3-methoxy-azetidinyl)-hexanoic acid-Thr-Sar-MeLeu-Leu-MeLeu-Ala-D-Hiv-MeLeu-Leu-MeVal} |

| Structure | Patent Example No. | Name |
|---|---|---|
| 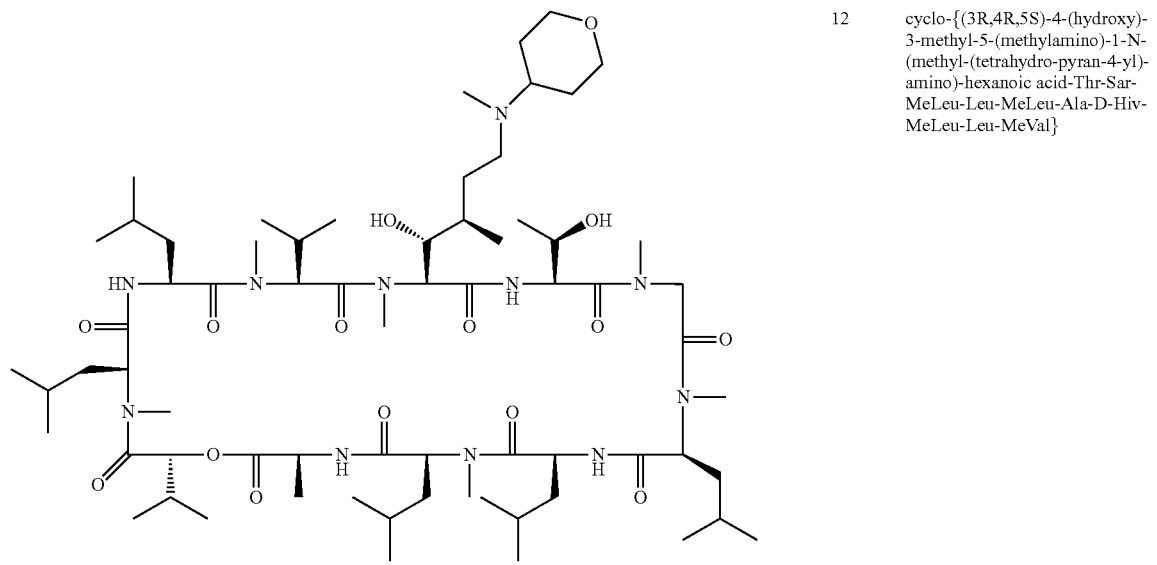 | 12 | cyclo-{(3R,4R,5S)-4-(hydroxy)-3-methyl-5-(methylamino)-1-N-(methyl-(tetrahydro-pyran-4-yl)-amino)-hexanoic acid-Thr-Sar-MeLeu-Leu-MeLeu-Ala-D-Hiv-MeLeu-Leu-MeVal} |
| 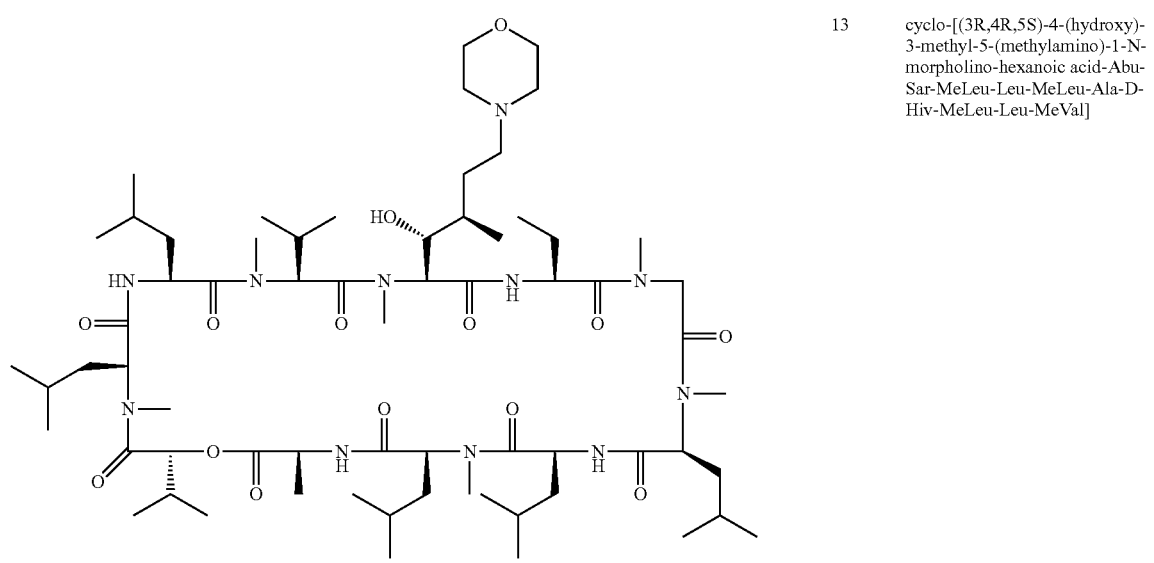 | 13 | cyclo-[(3R,4R,5S)-4-(hydroxy)-3-methyl-5-(methylamino)-1-N-morpholino-hexanoic acid-Abu-Sar-MeLeu-Leu-MeLeu-Ala-D-Hiv-MeLeu-Leu-MeVal] |

| Structure | Patent Example No. | Name |
|---|---|---|
| 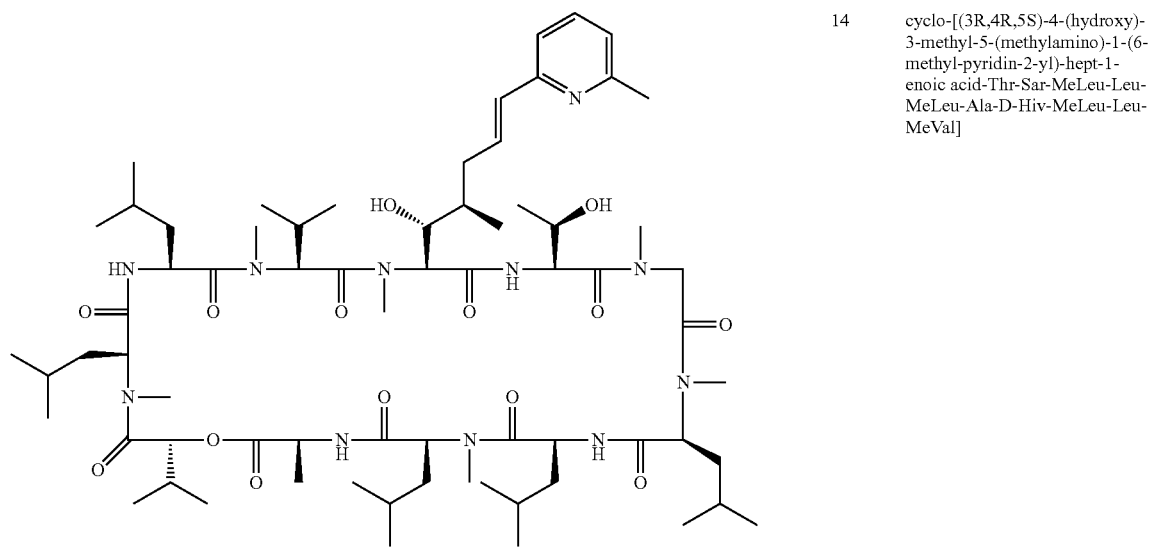 | 14 | cyclo-[(3R,4R,5S)-4-(hydroxy)-3-methyl-5-(methylamino)-1-(6-methyl-pyridin-2-yl)-hept-1-enoic acid-Thr-Sar-MeLeu-Leu-MeLeu-Ala-D-Hiv-MeLeu-Leu-MeVal] |
| 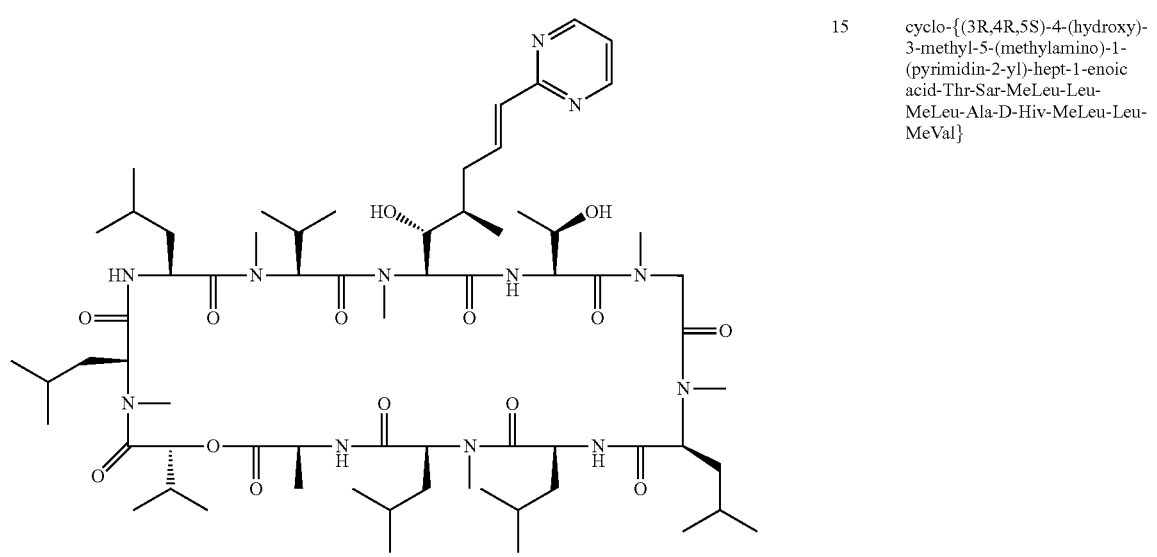 | 15 | cyclo-{(3R,4R,5S)-4-(hydroxy)-3-methyl-5-(methylamino)-1-(pyrimidin-2-yl)-hept-1-enoic acid-Thr-Sar-MeLeu-Leu-MeLeu-Ala-D-Hiv-MeLeu-Leu-MeVal} |

-continued
| Structure | Patent Example No. | Name |
|---|---|---|
| 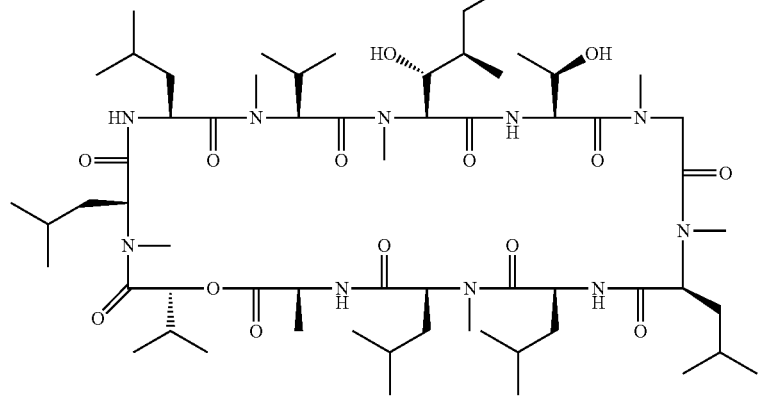 | 16 | cyclo-[(3R,4R,5S)-4-(hydroxy)-3-methyl-5-(methylamino)-1-(pyrimidin-2-yl)-heptanoic acid-Thr-Sar-MeLeu-Leu-MeLeu-Ala-D-Hiv-MeLeu-Leu-MeVal] |
| 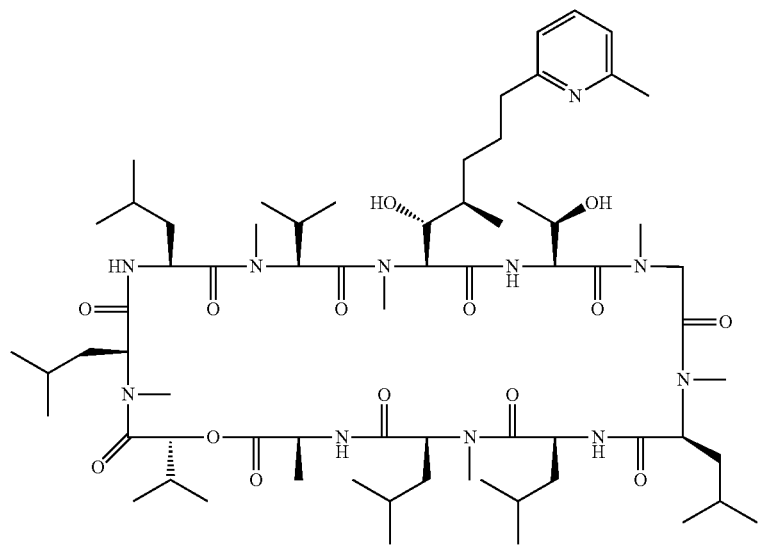 [SMILES: Cc1cccc(CCC[C@@H](C)[C@@H](O)[C@@H]2C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N2C)n1] | 17 | cyclo-[(3R,4R,5S)-4-(hydroxy)-3-methyl-5-(methylamino)-1-(6-methyl-pyridin-2-yl)-heptanoic acid-Thr-Sar-MeLeu-Leu-MeLeu-Ala-D-Hiv-MeLeu-Leu-MeVal] |

| Structure | Patent Example No. | Name |
|---|---|---|
| 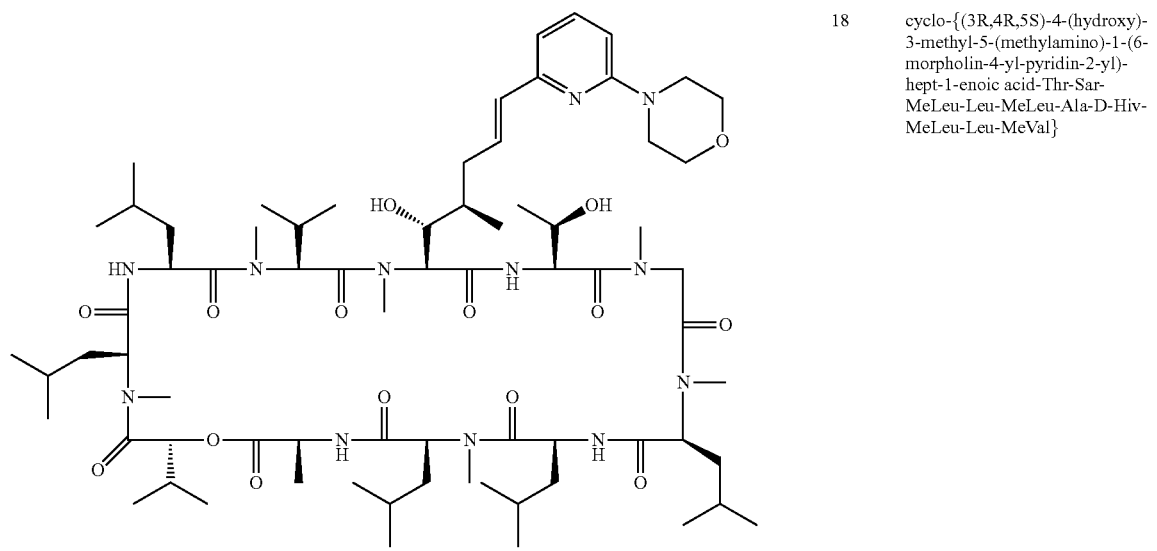 | 18 | cyclo-{(3R,4R,5S)-4-(hydroxy)-3-methyl-5-(methylamino)-1-(6-morpholin-4-yl-pyridin-2-yl)-hept-1-enoic acid-Thr-Sar-MeLeu-Leu-MeLeu-Ala-D-Hiv-MeLeu-Leu-MeVal} |
| 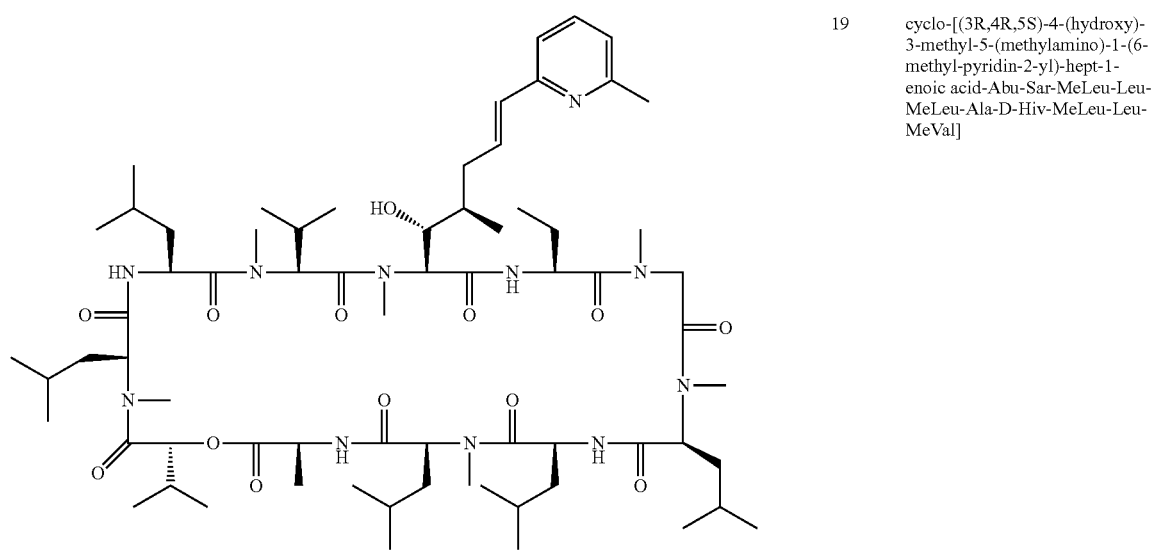 | 19 | cyclo-[(3R,4R,5S)-4-(hydroxy)-3-methyl-5-(methylamino)-1-(6-methyl-pyridin-2-yl)-hept-1-enoic acid-Abu-Sar-MeLeu-Leu-MeLeu-Ala-D-Hiv-MeLeu-Leu-MeVal] |

-continued
| Structure | Patent Example No. | Name |
|---|---|---|
| 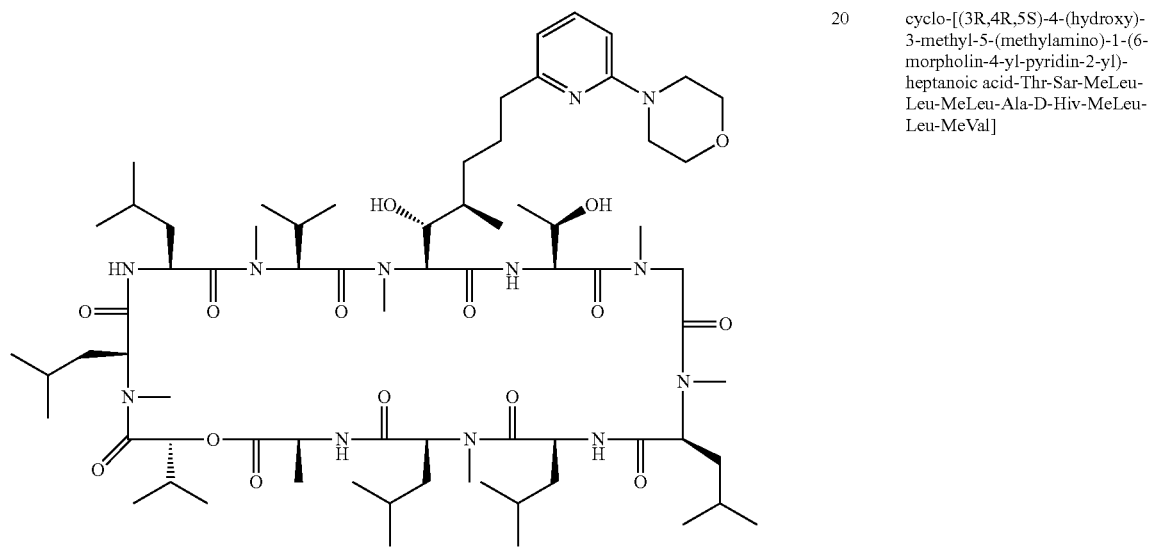 | 20 | cyclo-[(3R,4R,5S)-4-(hydroxy)-3-methyl-5-(methylamino)-1-(6-morpholin-4-yl-pyridin-2-yl)-heptanoic acid-Thr-Sar-MeLeu-Leu-MeLeu-Ala-D-Hiv-MeLeu-Leu-MeVal] |
| 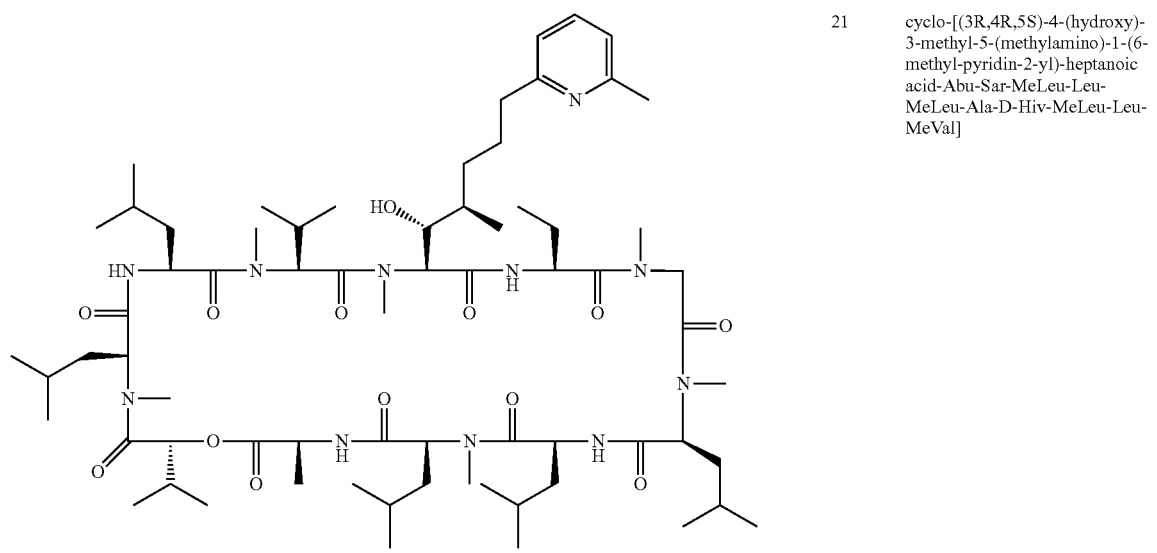 | 21 | cyclo-[(3R,4R,5S)-4-(hydroxy)-3-methyl-5-(methylamino)-1-(6-methyl-pyridin-2-yl)-heptanoic acid-Abu-Sar-MeLeu-Leu-MeLeu-Ala-D-Hiv-MeLeu-Leu-MeVal] |

| Structure | Patent Example No. | Name |
|---|---|---|
| 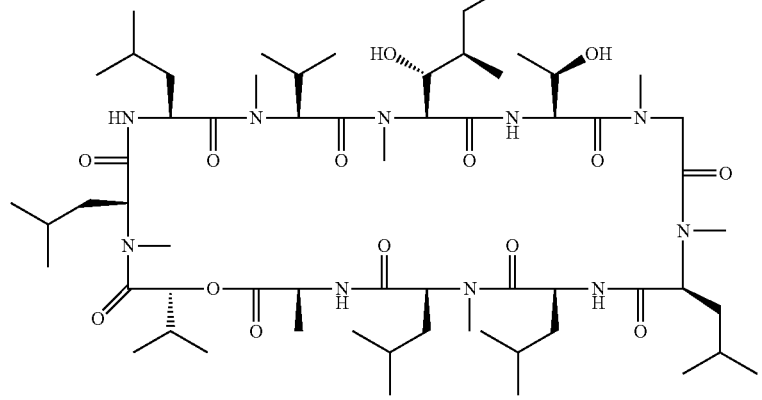 | 22 | cyclo-[(3R,4R,5S)-4-(hydroxy)-3-methyl-5-(methylamino)-1-N-(8-oxa-3-aza-bicyclo[3.2.1]octane)-hexanoic acid-Thr-Sar-MeLeu-Leu-MeLeu-Ala-D-Hiv-MeLeu-Leu-MeVal] |
| 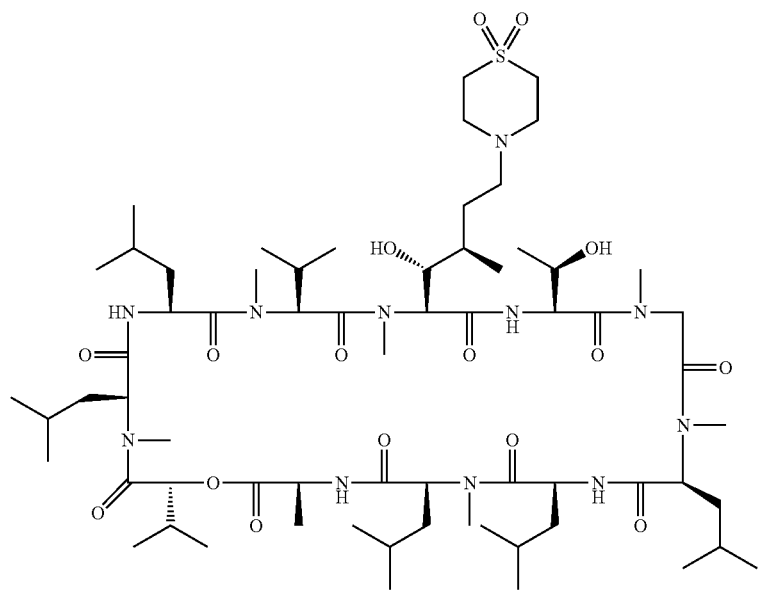 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCS(=O)(=O)CC2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 23 | cyclo-[(3R,4R,5S)-4-(hydroxy)-3-methyl-5-(methylamino)-1-N-(thiomorpholine 1,1-dioxide)-hexanoic acid-Thr-Sar-MeLeu-Leu-MeLeu-Ala-D-Hiv-MeLeu-Leu-MeVal] |

| Structure | Patent Example No. | Name |
|---|---|---|
| 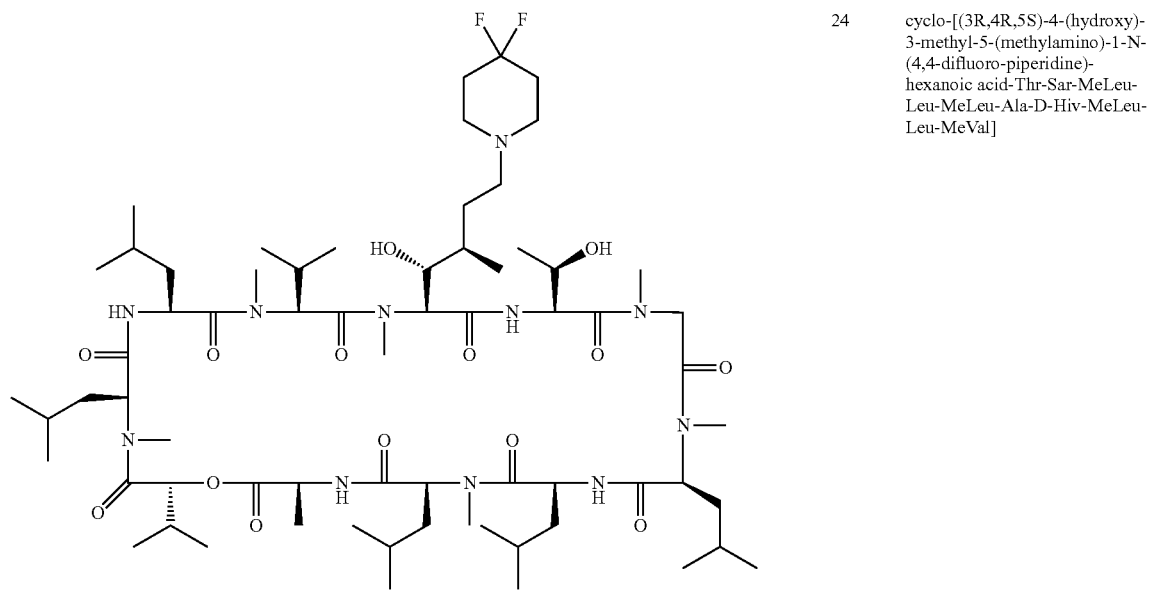 | 24 | cyclo-[(3R,4R,5S)-4-(hydroxy)-3-methyl-5-(methylamino)-1-N-(4,4-difluoro-piperidine)-hexanoic acid-Thr-Sar-MeLeu-Leu-MeLeu-Ala-D-Hiv-MeLeu-Leu-MeVal] |
| 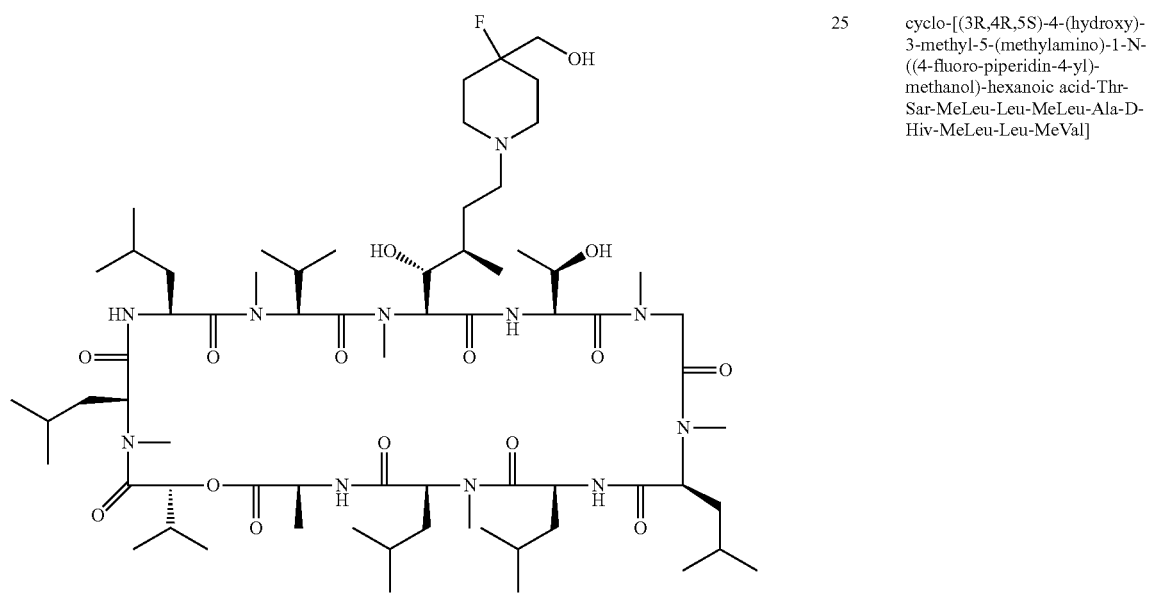 | 25 | cyclo-[(3R,4R,5S)-4-(hydroxy)-3-methyl-5-(methylamino)-1-N-((4-fluoro-piperidin-4-yl)-methanol)-hexanoic acid-Thr-Sar-MeLeu-Leu-MeLeu-Ala-D-Hiv-MeLeu-Leu-MeVal] |

| Structure | Patent Example No. | Name |
|---|---|---|
| 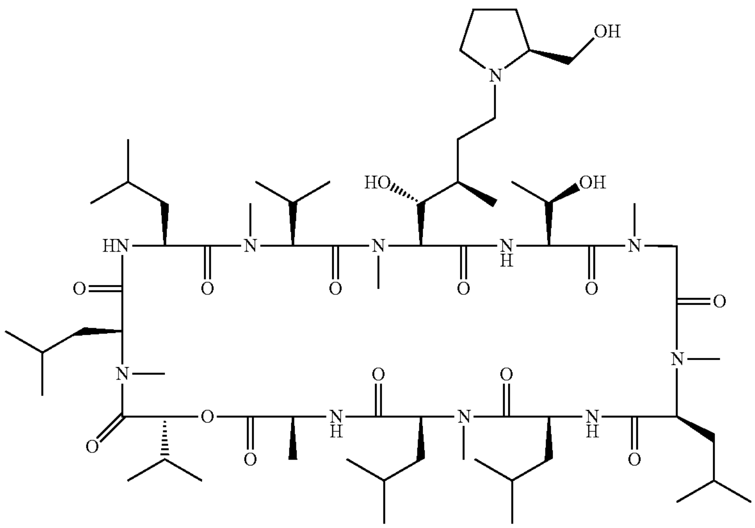 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCC[C@H]2CO)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 26 | cyclo-[(3R,4R,5S)-4-(hydroxy)-3-methyl-5-(methylamino)-1-N-((S)-1-Pyrrolidin-2-yl-methanol)-hexanoic acid-Thr-Sar-MeLeu-Leu-MeLeu-Ala-D-Hiv-MeLeu-Leu-MeVal] |
| 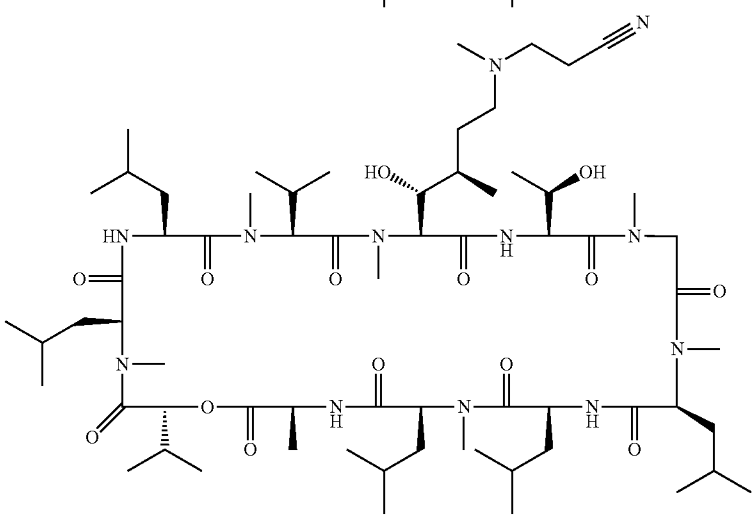 | 27 | cyclo-[(3R,4R,5S)-4-(hydroxy)-3-methyl-5-(methylamino)-1-N-(3-methylamino-propionitrile)-hexanoic acid-Thr-Sar-MeLeu-Leu-MeLeu-Ala-D-Hiv-MeLeu-Leu-MeVal] |
| 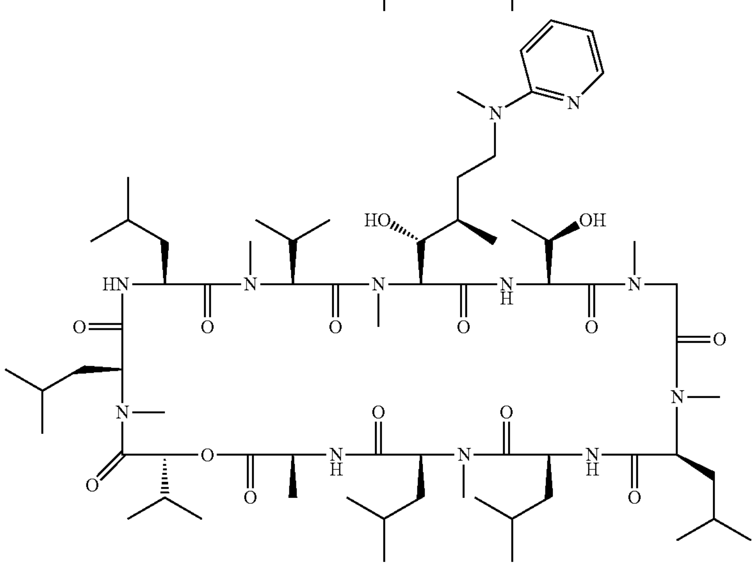 | 28 | cyclo-[(3R,4R,5S)-4-(hydroxy)-3-methyl-5-(methylamino)-1-N-(methyl-pyridin-2-yl-amine)-hexanoic acid-Thr-Sar-MeLeu-Leu-MeLeu-Ala-D-Hiv-MeLeu-Leu-MeVal] |

| Structure | Patent Example No. | Name |
|---|---|---|
| 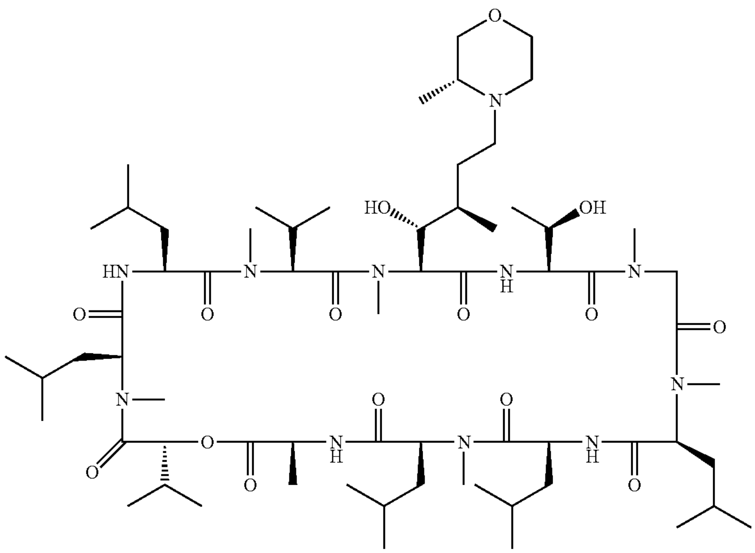 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCOC[C@H]2C)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 29 | cyclo-[(3R,4R,5S)-4-(hydroxy)-3-methyl-5-(methylamino)-1-N-((R)-3-Methyl-morpholine)-hexanoic acid-Thr-Sar-MeLeu-Leu-MeLeu-Ala-D-Hiv-MeLeu-Leu-MeVal] |
| 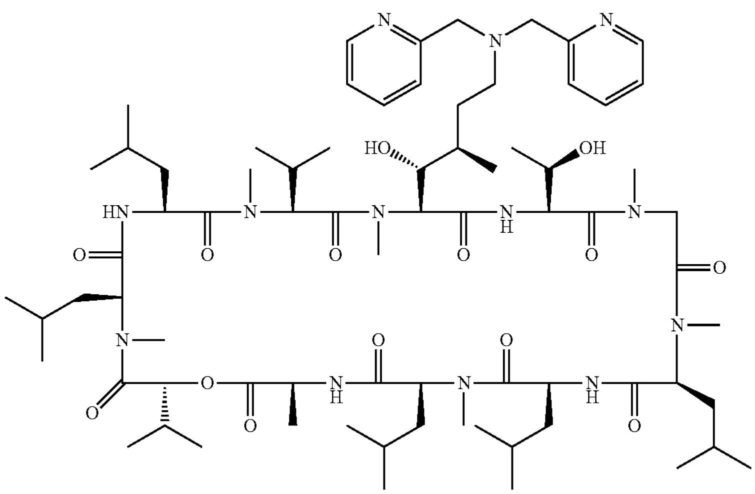 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(Cc2ccccn2)Cc2ccccn2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 30 | cyclo-[(3R,4R,5S)-4-(hydroxy)-3-methyl-5-(methylamino)-1-N-(bis-pyridin-2-ylmethyl-amine)-hexanoic acid-Thr-Sar-MeLeu-Leu-MeLeu-Ala-D-Hiv-MeLeu-Leu-MeVal] |
| 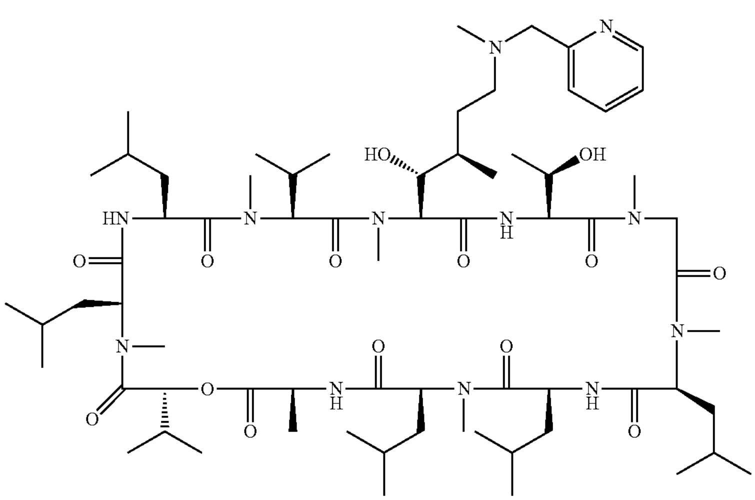 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)Cc2ccccn2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 31 | cyclo-[(3R,4R,5S)-4-(hydroxy)-3-methyl-5-(methylamino)-1-N-(methyl-pyridin-2-ylmethyl-amino)-hexanoic acid-Thr-Sar-MeLeu-Leu-MeLeu-Ala-D-Hiv-MeLeu-Leu-MeVal] |

-continued
| Structure | Patent Example No. | Name |
|---|---|---|
| 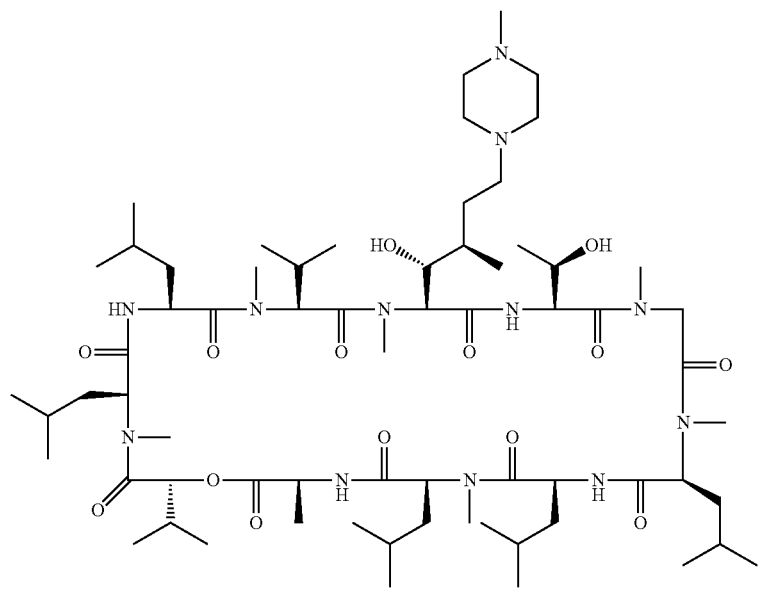 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCN(C)CC2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 32 | cyclo-[(3R,4R,5S)-4-(hydroxy)-3-methyl-5-(methylamino)-1-N-(N'-methylpiperazine)-hexanoic acid-Thr-Sar-MeLeu-Leu-MeLeu-Ala-D-Hiv-MeLeu-Leu-MeVal] |
| 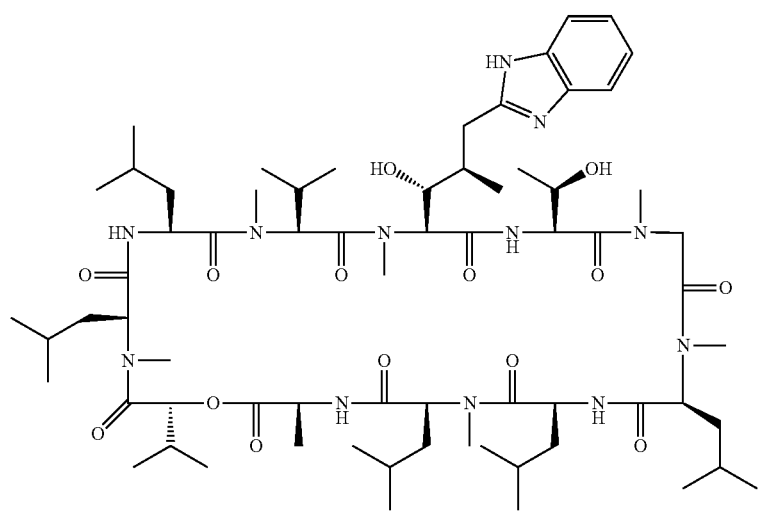 [SMILES: CC(C)C[C@@H]1C(=O)N[C@H](CC(C)C)C(=O)N(C)[C@H](C(C)C)C(=O)N(C)[C@H]([C@H](O)[C@H](C)Cc2nc3ccccc3[nH]2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 33 | cyclo-[(2R,3R,4S)-1-(1H-benzoimidazol-2-yl)-2-methyl-4-methylamino-3-hydroxy-pentanoic acid-Thr-Sar-MeLeu-Leu-MeLeu-Ala-D-Hiv-MeLeu-Leu-MeVal] |

-continued
| Structure | Patent Example No. | Name |
|---|---|---|
| 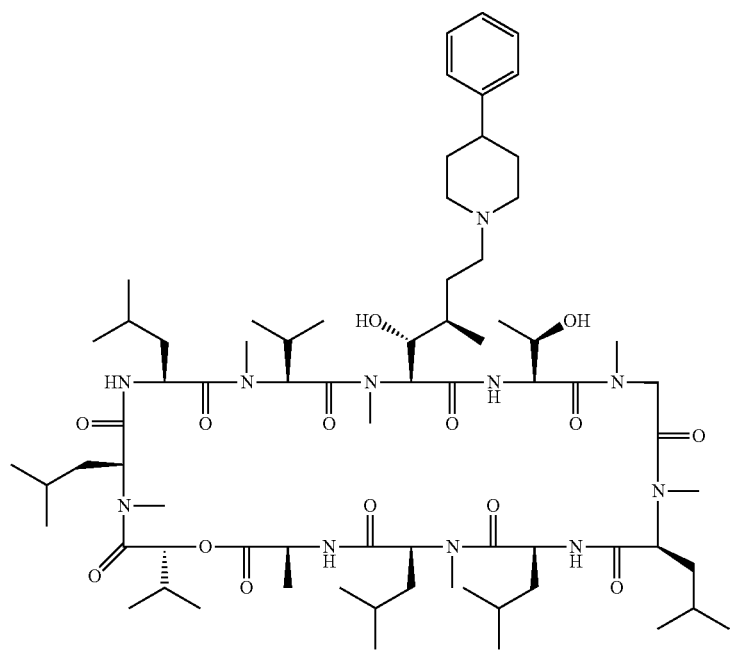 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCC(c3ccccc3)CC2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 34 | cyclo-[(3R,4R,5S)-4-(hydroxy)-3-methyl-5-(methylamino)-1-(4-phenyl-1-piperidyl)-hexanoic acid-Thr-Sar-MeLeu-Leu-MeLeu-Ala-D-Hiv-MeLeu-Leu-MeVal] |
| 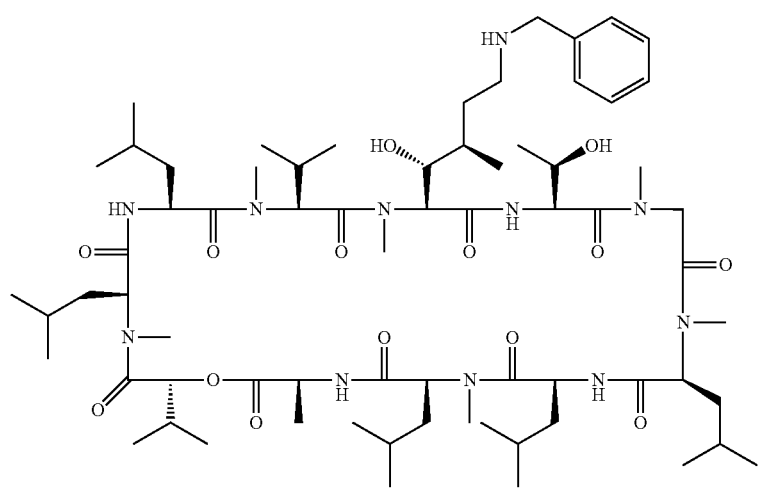 [SMILES: CC(C)C[C@@H]1C(=O)N[C@H](CC(C)C)C(=O)N(C)[C@H](C(C)C)C(=O)N(C)[C@H]([C@H](O)[C@H](C)CCNCc2ccccc2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 35 | cyclo-[(3R,4R,5S)-1-benzylamino-3-methyl-5-methylamino-4-hydroxy-hexanoic acid-Thr-Sar-MeLeu-Leu-MeLeu-Ala-D-Hiv-MeLeu-Leu-MeVal] |

-continued
| Structure | Patent Example No. | Name |
|---|---|---|
| 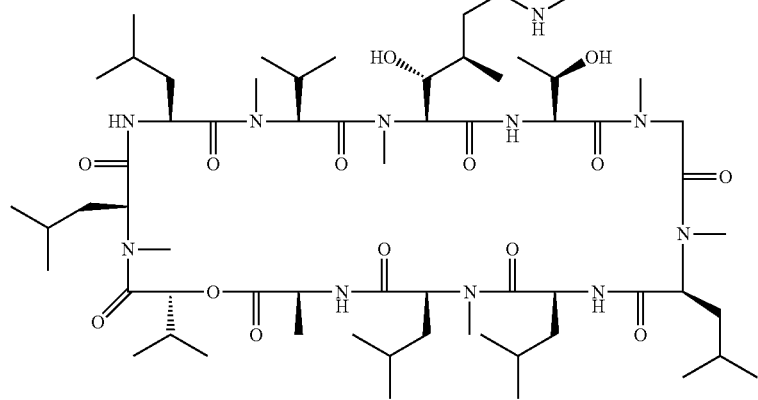 | 36 | cyclo-[(3R,4R,5S)-1-benzylcarbamoyl-3-methyl-5-methylamino-4-hydroxy-pentanoic acid-Thr-Sar-MeLeu-Leu-MeLeu-Ala-D-Hiv-MeLeu-Leu-MeVal] |
| 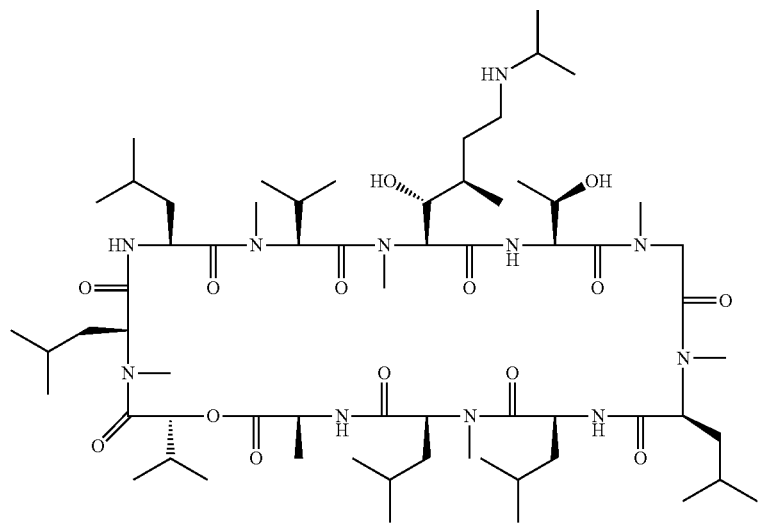 [SMILES: CC(C)C[C@@H]1C(=O)N[C@H](CC(C)C)C(=O)N(C)[C@H](C(C)C)C(=O)N(C)[C@H]([C@H](O)[C@H](C)CCNC(C)C)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 37 | cyclo-[(3R,4R,5S)-4-hydroxy-1-isopropylamino-3-methyl-5-methylamino-hexanoic acid-Thr-Sar-MeLeu-Leu-MeLeu-Ala-D-Hiv-MeLeu-Leu-MeVal] |

| Structure | Patent Example No. | Name |
|---|---|---|
| 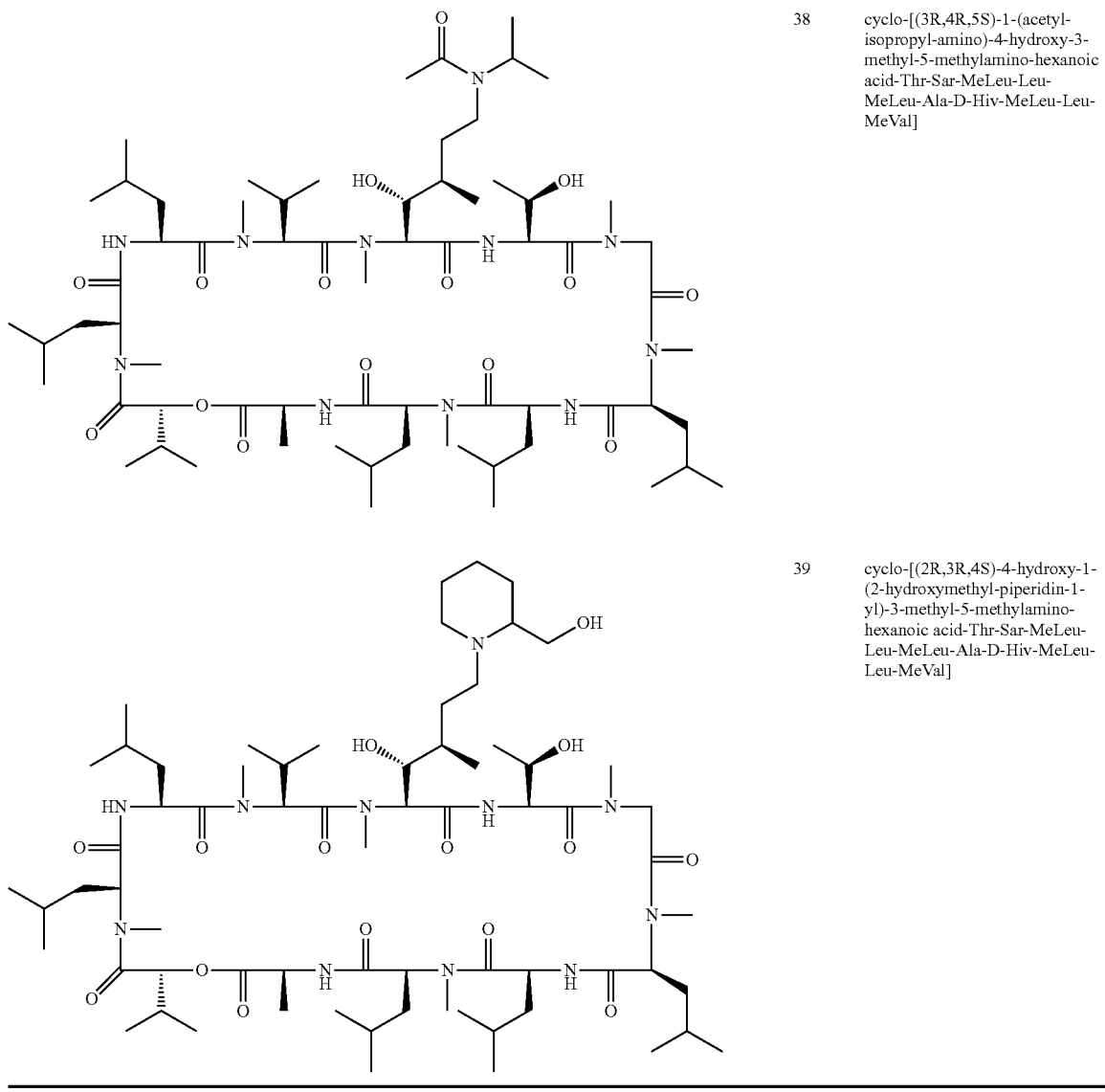 | 38 | cyclo-[(3R,4R,5S)-1-(acetyl-isopropyl-amino)-4-hydroxy-3-methyl-5-methylamino-hexanoic acid-Thr-Sar-MeLeu-Leu-MeLeu-Ala-D-Hiv-MeLeu-Leu-MeVal] |
| 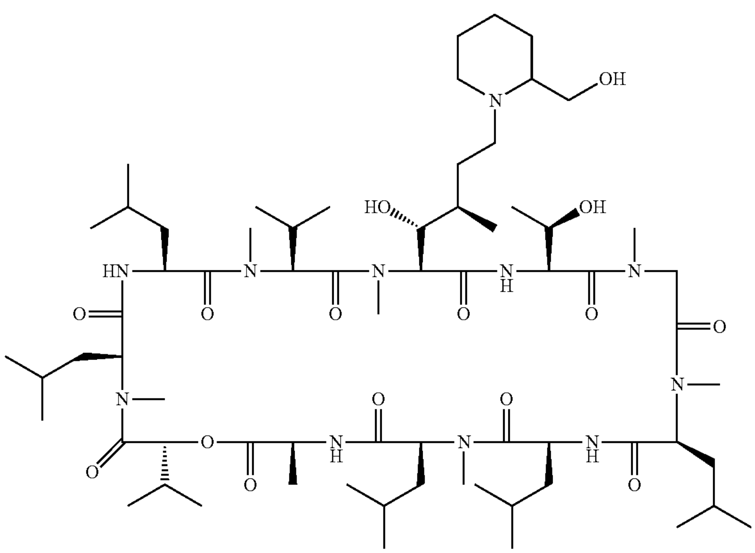 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCCCC2CO)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C] | 39 | cyclo-[(2R,3R,4S)-4-hydroxy-1-(2-hydroxymethyl-piperidin-1-yl)-3-methyl-5-methylamino-hexanoic acid-Thr-Sar-MeLeu-Leu-MeLeu-Ala-D-Hiv-MeLeu-Leu-MeVal] |

Methods for Preparing Compounds of the Invention

The skilled person will recognise that compounds of the invention may be prepared, in known manner, in a variety of ways. The routes below are merely illustrative of some methods that can be employed for the synthesis of compounds of formula (1).

The present invention further provides a process for the preparation of a compound of formula (1) in which L is —CH$_2$—, Q is a primary covalent bond and NR$_1$R$_2$ are as defined in formula (1), by conversion of the alkenyl group (AXX$_1$) of Example 1, or a protected derivative thereof, to an aldehyde by treatment with ozone in a suitable solvent such as dichloromethane, in the temperature range of −80° C. to 0° C., followed by treatment of the resulting species with an agent such as dimethylsulfide or triphenylphosphine at a suitable temperature such as between −80° C. to 40° C. The aldehyde or protected aldehyde may also be prepared by known methods such as by treatment of sodium periodate/osmium tetraoxide in combination with an oxidant such as N-methylmorpholine N-oxide or hydrogen peroxide in a solvent combinations such as 1,4-dioxane, tert-butanol and water. The resulting aldehyde (or lactol mixture) can be converted to the compound of formula (1) by treatment with an amine of formula HNR$_1$R$_2$, wherein R$_1$ and R$_2$ are as defined in formula (1), with a reducing agent such as sodium triacetoxyborohydride or sodium cyanoborohydride, with or without the presence of an acid such as acetic acid, in a solvent such as dichloromethane. If necessary protecting groups such as triethylsilyl groups can be removed with a reagent such as triethylamine trihydrofluoride.

Compounds of formula (1) wherein L-Q-NR₁R₂ make up a group of formula (2)

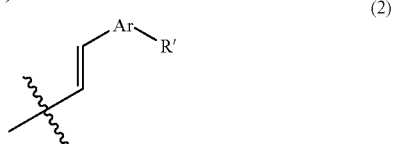
(2)

may be conveniently prepared by treatment of the aldehyde derived from Example 1 above, or a protected derivative thereof, with an alkyl-phosphonium salt or alkyl organophosphinate ester in combination with a base such as lithium diisopropylamide, sodium hexamethyldisilazide, potassium hexamethyldisilazide, butyl lithium, potassium tert-butoxide, sodium hydride in a solvent such as THF or toluene at a temperature in the range of $-80°$ C. to $50°$ C., preferably $-80°$ C. to room temperature. If necessary protecting groups such as triethylsilyl groups can be removed with a reagent such as triethylamine trihydrofluoride.

Compounds of formula (1) wherein L-Q-NR₁R₂ make up a group of formula (3)

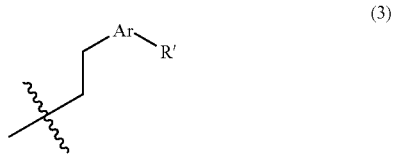
(3)

may be conveniently prepared by treatment of compounds of formula (2) as defined above with hydrogen in a solvent such as ethyl acetate or isopropanol with a catalyst such as 5-10% palladium on carbon.

Compounds of formula (1) wherein L-Q-NR₁R₂ make up a group of formula (4)

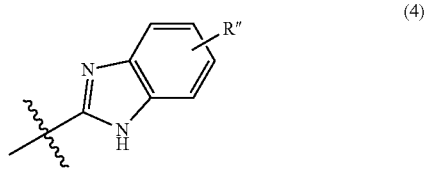
(4)

may be conveniently prepared by treatment of the aldehyde derived from Example 1 above, or a protected derivative thereof, with the corresponding unsubstituted or substituted diamine in a solvent such as acetonitrile, with an oxidant such as air or oxygen at a temperature in the range of $0°$ C. to $50°$ C., preferably room temperature. If necessary protecting groups such as triethylsilyl groups can be removed with a reagent such as triethylamine trihydrofluoride.

Compounds of formula (1) in which L is a bond, Q is a carbonyl and NR₁R₂ are as defined in formula (1), by conversion of the aldehyde derived from Example 1 above, or a protected derivative thereof, to a carboxylic acid with an oxidant such as sodium chlorite, in the presence of an alkene such as 2,3-dimethylbut-2-ene, in a solvent such as tetrahydrofuran, tert-butanol and buffered aqueous at a temperature in the range of $-20°$ C. to $50°$ C., preferably room temperature. Subsequent amide formation using standard conditions such as (dimethylamino)-N,N-dimethyl(3H-[1,2,3]triazolo[4,5-b]pyridin-3-yloxy)methaniminium hexafluorophosphate and triethylamine with an amine of formula HNR₁R₂ in a solvent such as dichloromethane followed by removal of protecting groups, if required, such as triethylsilyl groups with a reagent such as triethylamine trihydrofluoride.

Compounds of formula (1) wherein L-Q-NR₁R₂ make up a group of formula (5)

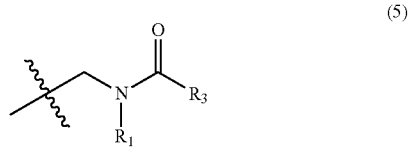
(5)

may be conveniently prepared by reaction of a group of formula (1) wherein L is —CH₂—, Q is a primary covalent bond and NR₁ are as defined in formula (1) with a group of formula R₃CO₂H under standard coupling conditions (as above) or with a group of formula R₃COCl, (R₃CO)₂O in a solvent such as dichloromethane and a base such as triethylamine, pyridine or diisopropyl amine.

Compounds of the invention include those where X is H, i.e. the amino acid at position 2 is Abu. Such compounds can be prepared via deoxygenation of the amino acid threonine at said position to turn the CH(OH)CH₃ into CH₂CH₃. Thus included within the scope of the invention is the use of a thionochloroformate to produce a compound of type C—OC(=S)OR, which can then be turned into a C—H analogue. The compounds of the invention can be produced by reacting phenyl thionochloroformate with the 2-threonine hydroxyl group. The invention as disclosed herein therefore includes the use of a thionoformate, for example as shown in example intermediate 13(i):

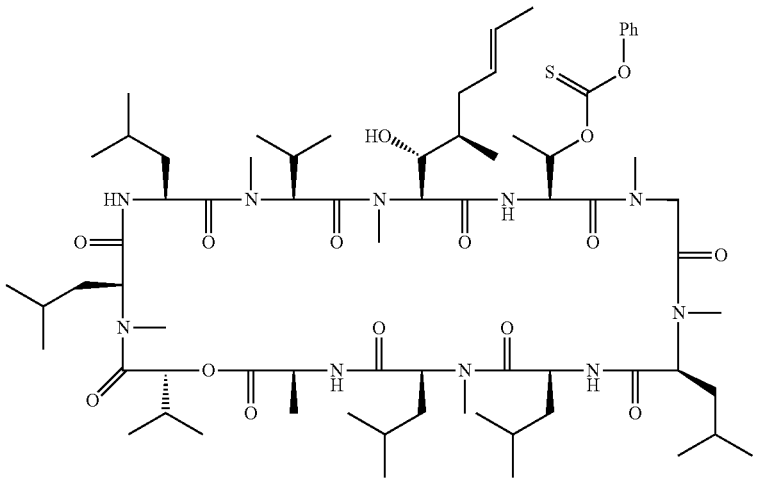 [SMILES: C/C=C/C[C@@H](C)[C@@H](O)[C@@H]1C(=O)N[C@H](C(C)OC(=S)Oc2ccccc2)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N1C]

in the preparation of compounds as disclosed herein.

Methods for the Preparation of Compounds of the Invention

Example 1

Production of Cyclo-(MeBmt-Thr-Sar-MeLeu-Leu-MeLeu-Ala-D-Hiv-MeLeu-Leu-MeVal) by fermentation of strain NRRL-18230

Cylindrotrichum sp. NRRL-18230 was sourced from the culture collection at the Agricultural Research Service, US Dept of Agriculture, US, and cultured on malt yeast agar (MYA: 2% malt extract, 0.4% yeast extract, 2% agar in deionised water) at 22° C. Starting material was generated by suspending ten 0.5 cm² plugs taken from the growing edges of a mature agar plate culture in sterile distilled water (10 ml) containing glass beads (2.5-3.5 mm diameter, 5 ml) and shaking vigorously to cause homogenisation. A seed culture was generated by aseptically inoculating each of three 250 ml conical flasks containing 100 ml malt yeast broth (MYB: 2% malt extract and 0.4% yeast extract in deionised water at native pH) with 2 ml of the starting material and culturing at 22° C. and 150 rpm on a rotating shaker. After 11 days the mycelial pellets from the first seed stage were macerated with glass beads in distilled water and a second seed stage was generated by inoculating each of fifteen 250 ml conical flasks containing 100 ml MYB medium with 10% v/v of the macerated material and culturing at 22° C. and 150 rpm. After a further 14 days, a production stage was initiated by inoculating each of six 5 L Erlenmeyer flasks containing 2.5 L MYB medium with 250 ml of macerated material from mycelia pellets produced from the second seed stage. The cultures were grown at 100 rpm and 22° C. and harvested after 14 days when titres of cyclo-(MeBmt-Thr-Sar-MeLeu-Leu-MeLeu-Ala-D-Hiv-MeLeu-Leu-MeVal) had reached a plateaux, as determined by sampling and analysing by reverse phase HPLC. The harvest biomass was collected by centrifugation at 3000 rpm for 15 minutes using a Beckman J6B Centrifuge. The resulting pellet was extracted by homogenising the biomass with portions of ethyl acetate (3×2.5 L) followed by intermittent stirring over several hours to allow extraction to occur. This process was similarly repeated with methanol (2×1.5 L). The ethyl acetate and methanol extracts were separately concentrated by rotary evaporation. The ethyl acetate extract was defatted by dissolving in acetonitrile (300 ml) and extracting with n-hexane (2×300 ml). The combined hexane layers were back-extracted with acetonitrile (300 ml) and then the acetonitrile layers were combined and dried to yield 1.2 g of acetonitrile-soluble material. The methanol extract was similarly defatted to yield 2.7 g of acetonitrile-soluble material. The acetonitrile-soluble samples from the ethyl acetate and methanol extracts were dissolved and combined in 1:1 n-hexane:ethyl acetate (10 ml) and purified by column chromatography on silica gel (35-70 µm, column: ø 8 cm×16 cm) eluting initially with n-hexane:ethyl acetate (1:1) followed by ethyl acetate and then ethyl acetate-methanol (98:2 followed by 96:4), with all mobile phases containing 0.1% formic acid. Fractions found to contain only the compound of interest, as determined by analysis using reversed phase HPLC with evaporative light scattering detection, were combined and concentrated in vacuo to yield pure Cyclo-(MeBmt-Thr-Sar-MeLeu-Leu-MeLeu-Ala-D-Hiv-MeLeu-Leu-MeVal) (1.248 g).

Example 2

Preparation of cyclo-[(3R,4R,5S)-4-(hydroxy)-3-methyl-5-(methylamino)-1-N-morpholino-hexanoic acid-Thr-Sar-MeLeu-Leu-MeLeu-Ala-D-Hiv-MeLeu-Leu-MeVal]

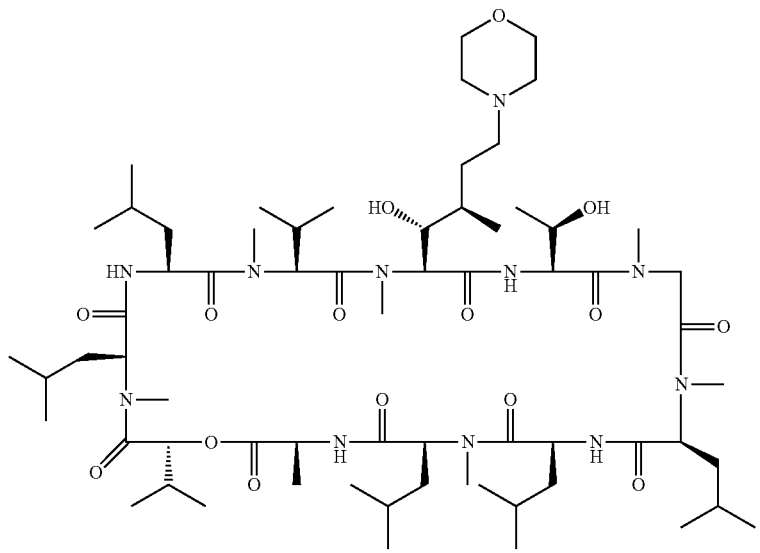 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCOCC2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

i) Preparation of cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]}

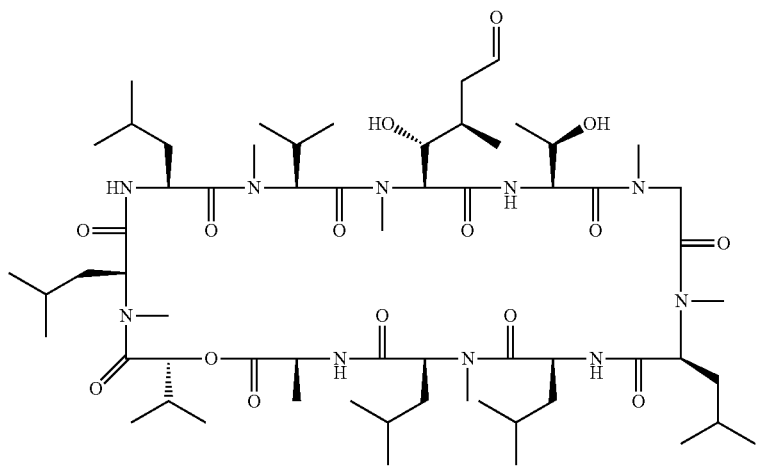 [SMILES: CC(C)C[C@@H]1C(=O)N[C@H](CC(C)C)C(=O)N(C)[C@H](C(C)C)C(=O)N(C)[C@H]([C@H](O)[C@H](C)CC=O)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

Cyclo-(MeBmt-Thr-Sar-MeLeu-Leu-MeLeu-Ala-D-Hiv-MeLeu-Leu-MeVal) (Example 1) (0.124 g, 0.1 mmol) was dissolved in dry dichloromethane (16 ml) and added to a 3-neck flask equipped with a glass inlet tube (for nitrogen/ozone addition) with an outlet connected to a Dreschler bottle containing 2 M potassium iodide solution. The reaction mixture was cooled to −78° C. using a solid $CO_2$/acetone bath under a nitrogen atmosphere. When the temperature of the reaction vessel had stabilised, ozone was bubbled through the reaction mixture until it became a pale blue colour (approx. 3-5 minutes). The ozone supply was removed and dry nitrogen gas was then bubbled through the reaction mixture until the blue colour disappeared. Dimethylsulphide (0.038 mL) was then added, and the reaction mixture was allowed to warm to room temperature over 3 hours. After this time, the reaction mixture was washed with brine then dried ($Na_2SO_4$), filtered and evaporated under reduced pressure to yield the crude title compound as a mixture of aldehyde-lactol which was used in the next step without isolation. ESMS MNa+ 1257.1, MK+1273.3

Example 2

Preparation of cyclo-[(3R,4R,5S)-4-(hydroxy)-3-methyl-5-(methylamino)-1-N-morpholino-hexanoic acid-Thr-Sar-MeLeu-Leu-MeLeu-Ala-D-Hiv-MeLeu-Leu-MeVal]

To a stirred solution of cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.123 g, 0.1 mmol) in dry dichloromethane (10 ml) was added morpholine (0.044 ml, 0.5 mmol), sodium triacetoxyborohydride (0.089 g, 0.5 mmol) and the reaction mixture was stirred at room temperature for 18 h. After this time, additional amounts of morpholine (0.044 ml, 0.5 mmol) and sodium triacetoxyborohydride (0.089 g, 0.5 mmol) were added and the reaction mixture was stirred at 40° C. for 4.5 h. After this time, additional amounts of morpholine (0.025 ml, 0.28 mmol) and sodium triacetoxyborohydride (0.089 g, 0.5 mmol) were added and the reaction mixture was stirred at room temperature for a further 23 h. The reaction mixture was diluted with dichloromethane, washed with a saturated aqueous solution of sodium bicarbonate, brine, then the organic phase was dried ($Na_2SO_4$), filtered and evaporated. The residue was purified by SCX chromatography using a solvent gradient of 100% ethanol to 0.21 M trimethylamine in ethanol followed by MPLC chromatography using a solvent gradient of 100% dichloromethane to 92% dichloromethane/8% ethanol to give title compound as a white solid. ESMS MH+1306.6

Example 3

Preparation of cyclo-[(3R,4R,5S)-4-(hydroxy)-3-methyl-5-(methylamino)-1-N-(methyl-pyridin-4-ylmethyl-amino)-hexanoic acid-Thr-Sar-MeLeu-Leu-MeLeu-Ala-D-Hiv-MeLeu-Leu-MeVal]

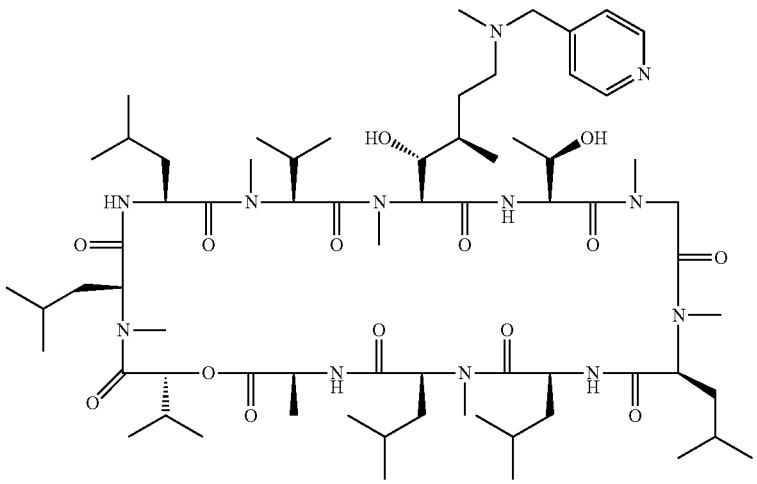 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)Cc2ccncc2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and methyl-pyridin-4-ylmethyl-amine to afford the product (12 mg). ESMS MI-1+1341.6

Example 4

Preparation of cyclo-{(3R,4R,5S)-4-(hydroxy)-3-methyl-5-(methylamino)-1-N-[methyl-2-(pyridin-2-yl)-ethyl-amino]-hexanoic acid-Thr-Sar-MeLeu-Leu-MeLeu-Ala-D-Hiv-MeLeu-Leu-MeVal}

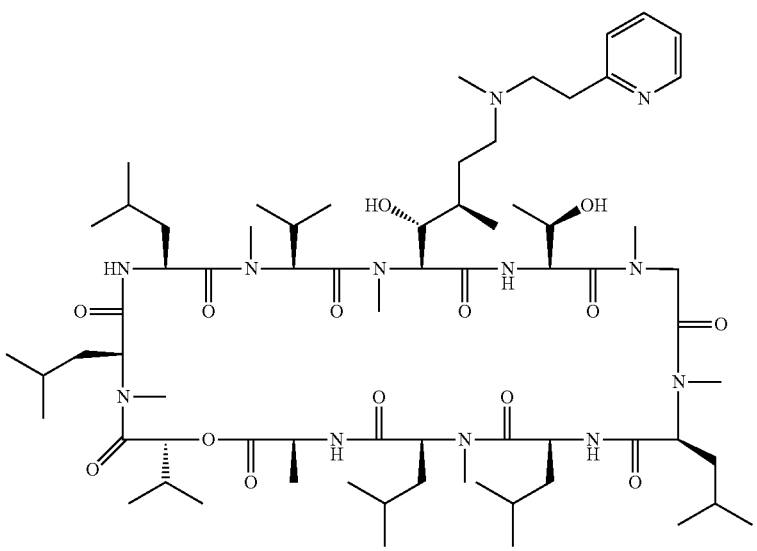 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)CCc2ccccn2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and methyl-2-(pyridin-2-yl)-ethyl-amine to afford the product (22 mg). ESMS MI-1+1355.5

Example 5

Preparation of cyclo-{(3R,4R,5S)-4-(hydroxy)-3-methyl-5-(methylamino)-1-N-[methyl-(2-methyl-2H-pyrazol-3-ylmethyl)-amino]-hexanoic acid-Thr-Sar-MeLeu-Leu-MeLeu-Ala-D-Hiv-MeLeu-Leu-MeVal}

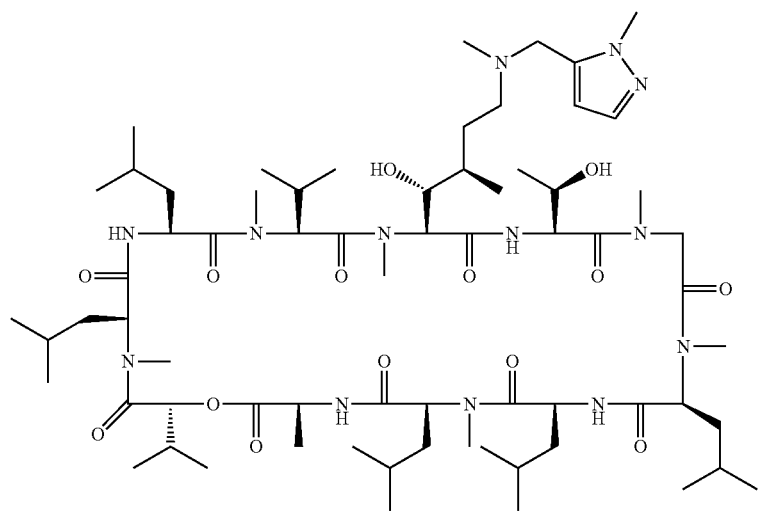 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)Cc2ccnn2C)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and methyl-(2-methyl-2H-pyrazol-3-ylmethyl)-amine to afford the product (37 mg). ESMS MH+1344.6

Example 6

Preparation of cyclo-{(3R,4R,5S)-4-(hydroxy)-3-methyl-5-(methylamino)-1-N-[methyl-(1H-tetrazol-5-ylmethyl)-amino]-hexanoic acid-Thr-Sar-MeLeu-Leu-MeLeu-Ala-D-Hiv-MeLeu-Leu-MeVal}

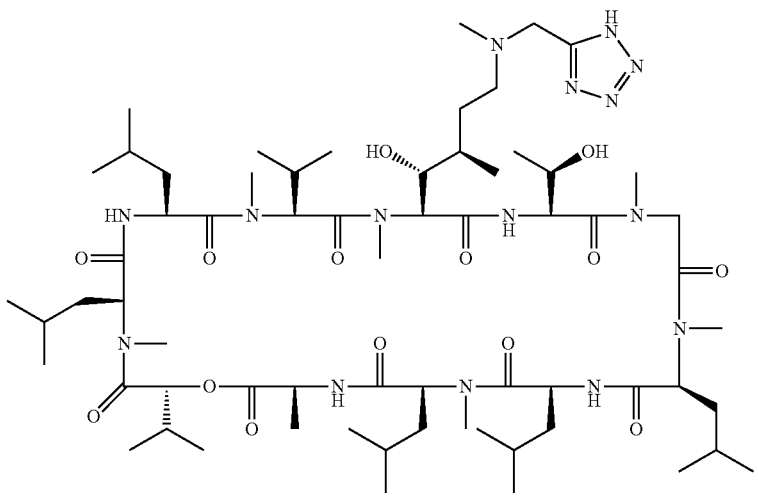 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)Cc2nnn[nH]2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and methyl-(1H-tetrazol-5-ylmethyl)-amine to afford the product (10 mg). ESMS MNa+ 1353.2

Example 7

Preparation of cyclo-[(3R,4R,5S)-4-(hydroxy)-3-methyl-5-(methylamino)-1-N-morpholino-hexanoic acid-(O-methyl-Thr)-Sar-MeLeu-Leu-MeLeu-Ala-D-Hiv-MeLeu-Leu-MeVal]

Cyclo-(MeBmt-Thr-Sar-MeLeu-Leu-MeLeu-Ala-D-Hiv-MeLeu-Leu-MeVal) (Example 1) (120 mg, 0.1 mmol) was dissolved in dry dichloromethane (2 mL) at room temperature and under nitrogen. To the reaction mixture was added powdered 3 Å molecular sieves (120 mg), trimethyloxonium tetrafluoroborate (142 mg, 0.96 mmol) and Proton sponge (247 mg, 1.15 mmol). The mixture was stirred for 1.5 hours, diluted with dichloromethane and washed with 1 M HCl (1×). The organic layer was dried over a hydrophobic fit and concentrated in vacuo. The product was purified by silica gel chromatography using iso-hexanes/acetone (1/1) as eluent to afford the target compound as viscous clear oil (110 mg, 87%). ESMS MH+1261.69

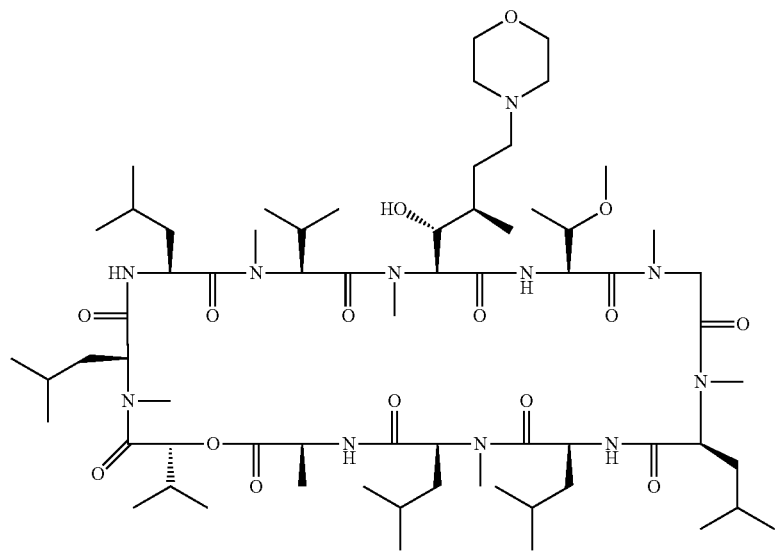 [SMILES: COC(C)[C@H]1NC(=O)[C@@H]([C@H](O)[C@H](C)CCN2CCOCC2)N(C)C(=O)[C@@H](C(C)C)N(C)C(=O)[C@@H](CC(C)C)NC(=O)[C@@H](CC(C)C)N(C)C(=O)[C@H](C(C)C)OC(=O)[C@@H](C)NC(=O)[C@@H](CC(C)C)N(C)C(=O)[C@@H](CC(C)C)NC(=O)[C@H](CC(C)C)N(C)C(=O)CN(C)C1=O]

i) Preparation of Cyclo-(MeBmt-(O-methyl-Thr)-Sar-MeLeu-Leu-MeLeu-Ala-D-Hiv-MeLeu-Leu-MeVal)

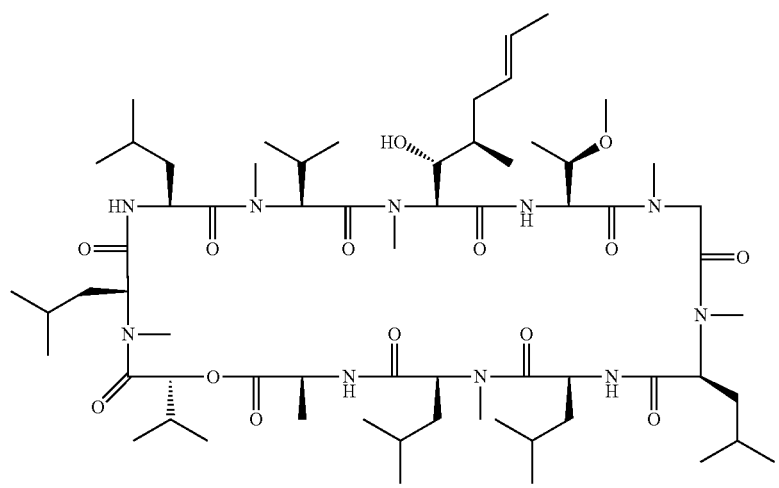 [SMILES: C/C=C/C[C@@H](C)[C@@H](O)[C@@H]1C(=O)N[C@H]([C@@H](C)OC)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N1C]

Example 7

Preparation of cyclo-[(3R,4R,5S)-4-(hydroxy)-3-methyl-5-(methylamino)-1-N-morpholino-hexanoic acid-(O-methyl-Thr)-Sar-MeLeu-Leu-MeLeu-Ala-D-Hiv-MeLeu-Leu-MeVal]

Cyclo-(MeBmt-(O-methyl-Thr)-Sar-MeLeu-Leu-MeLeu-Ala-D-Hiv-McLeu-Leu-MeVal) (Example 7, step i) (100 mg, 0.08 mmol) was dissolved in dry dichloromethane (40 mL) and added to a 3-neck flask equipped with a glass inlet tube (for nitrogen/ozone addition) with an outlet connected to a Dreschler bottle containing 2 M potassium iodide solution. The reaction mixture was cooled to −78° C. using a solid $CO_2$/acetone bath under a nitrogen atmosphere. When the temperature of the reaction vessel had stabilised, ozone was bubbled through the reaction mixture until it became a pale blue colour (approx. 3-5 minutes). The ozone supply was removed and dry nitrogen gas was then bubbled through the reaction mixture until the blue colour disappeared. Dimethylsulfide (0.058 mL, 0.8 mmol) was then added, and the reaction mixture was allowed to warm to room temperature over 3 hours. After this time the solvent was removed in vacuo to yield a foam. This was dissolved in dry dichloromethane (0.5 mL) and was added morpholine (0.069 mL, 0.8 mmol) followed by sodium triacetoxyborohydride (0.168 g, 0.8 mmol) at room temperature and under nitrogen. The reaction mixture was stirred at 40° C. for 18 h. After this time, additional amounts of morpholine (0.035 mL, 0.04 mmol) and sodium triacetoxyborohydride (0.085 g, 0.4 mmol) were added and the reaction mixture was stirred at 40° C. for 2 h. After this time the reaction mixture was diluted with dichloromethane and quenched with 2 M HCl). The organic layer was separated and washed with a saturated aqueous solution of sodium bicarbonate. The organic phase was dried through a hydrophobic frit and evaporated. The product was purified by silica gel chromatography using dichloromethane/ethanol (15/1 then 9/1) as eluent to afford the target compound as a white solid (45 mg, 43%). ESMS MH+1320.49

Example 8

Preparation of cyclo-{(3R,4R,5S)-4-(hydroxy)-3-methyl-5-(methylamino)-1-N-([1,4]dioxan-2-ylmethyl-methyl-amino)-hexanoic acid-Thr-Sar-MeLeu-Leu-MeLeu-Ala-D-Hiv-MeLeu-Leu-MeVal}

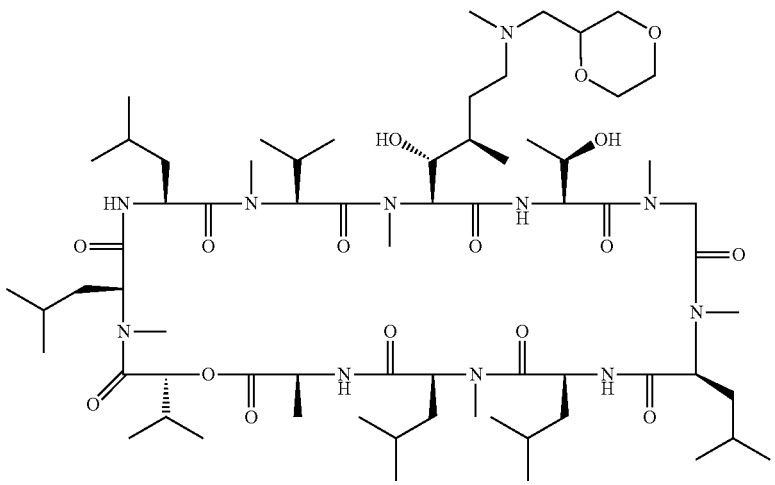 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)CC2COCCO2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and [1,4]dioxan-2-ylmethyl-methyl-amine to afford the product (21 mg). ESMS MH+1351

Example 9

Preparation of cyclo-{(3R,4R,5S)-4-(hydroxy)-3-methyl-5-(methylamino)-1-N-[3-trifluoromethyl-piperidinyl]-hexanoic acid-Thr-Sar-MeLeu-Leu-MeLeu-Ala-D-Hiv-MeLeu-Leu-MeVal}

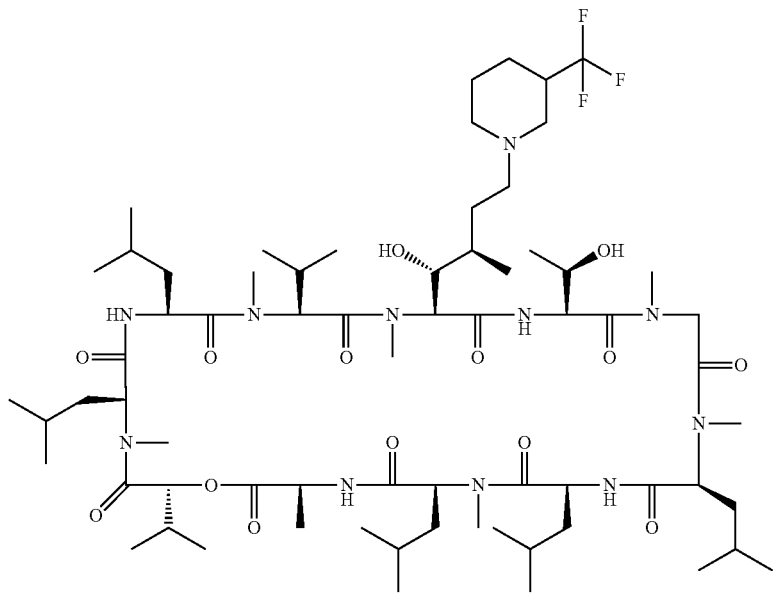 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCCC(C(F)(F)F)C2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and 3-trifluoromethyl-piperidine to afford the product (27 mg). ESMS MH+1373.1

Example 10

Preparation of cyclo-{(3R,4R,5S)-4-(hydroxy)-3-methyl-5-(methylamino)-1-N-[(2-methoxy-ethyl)-methyl-amino]-hexanoic acid-Thr-Sar-MeLeu-Leu-MeLeu-Ala-D-Hiv-MeLeu-Leu-MeVal}

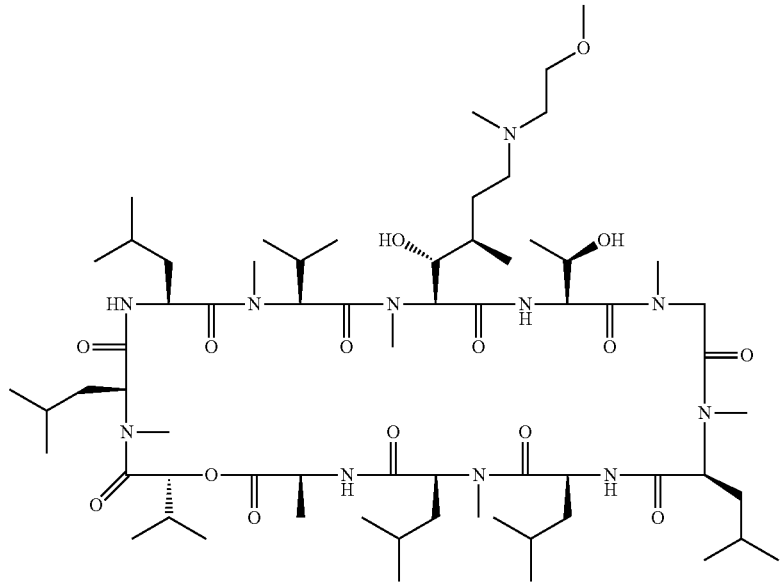 [SMILES: COCCN(C)CC[C@@H](C)[C@@H](O)[C@@H]1C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N1C]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and (2-methoxy-ethyl)-methyl-amine to afford the product (19 mg). ESMS MI-1+1308

Example 11

Preparation of cyclo-{(3R,4R,5S)-4-(hydroxy)-3-methyl-5-(methylamino)-1-N-(3-methoxy-azetidinyl)-hexanoic acid-Thr-Sar-MeLeu-Leu-MeLeu-Ala-D-Hiv-MeLeu-Leu-MeVal}

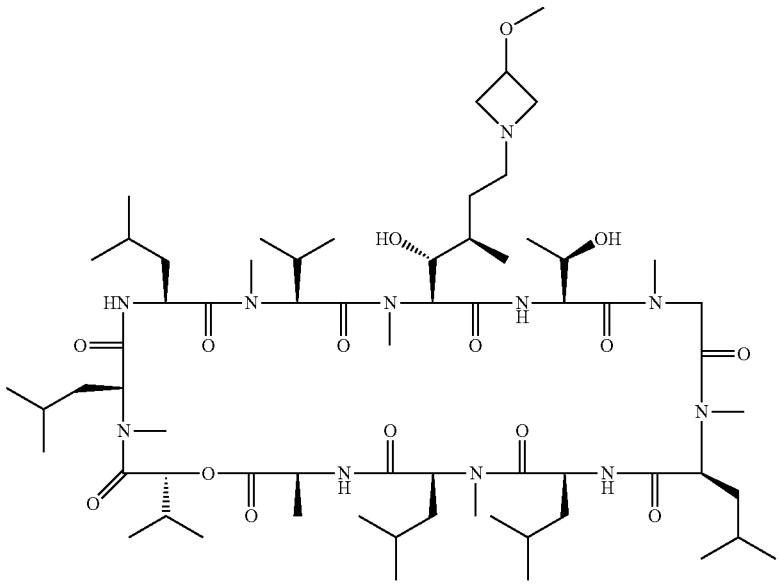 [SMILES: COC1CN(CC[C@@H](C)[C@@H](O)[C@@H]2C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N2C)C1]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and 3-methoxy-azetidine to afford the product (23 mg). ESMS MH+1307.1

Example 12

Preparation of cyclo-{(3R,4R,5S)-4-(hydroxy)-3-methyl-5-(methylamino)-1-N-(methyl-(tetrahydro-pyran-4-yl)-amino)-hexanoic acid-Thr-Sar-MeLeu-Leu-MeLeu-Ala-D-Hiv-MeLeu-Leu-MeVal}

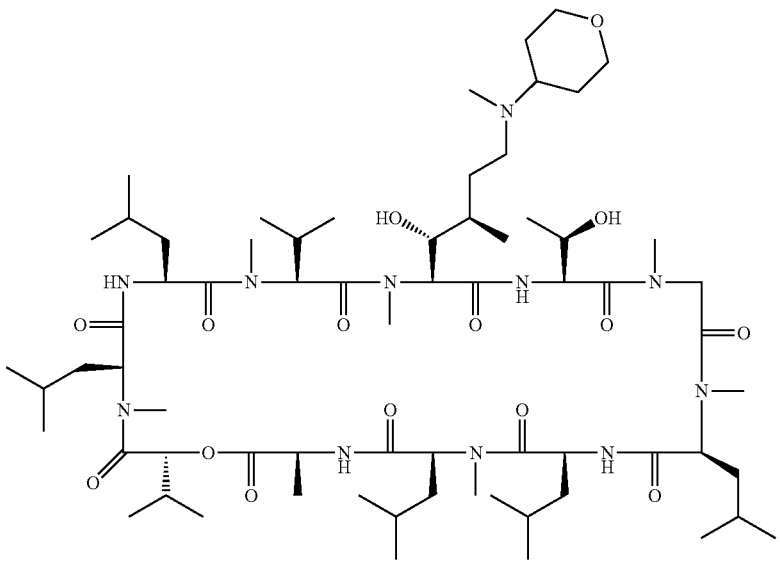 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(C)C2CCOCC2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 2 (Step ii) using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and methyl-(tetrahydro-pyran-4-yl)-amine to afford the product (26 mg). ESMS MH+1334.7

Example 13

Preparation of cyclo-[(3R,4R,5S)-4-(hydroxy)-3-methyl-5-(methylamino)-1-N-morpholino-hexanoic acid-Abu-Sar-MeLeu-Leu-MeLeu-Ala-D-Hiv-Me-Leu-Leu-MeVal]

To a stirred solution of cyclo-(MeBmt-Thr-Sar-MeLeu-Leu-MeLeu-Ala-D-Hiv-MeLeu-Leu-MeVal) (Example 1) (187 mg, 0.15 mmol) in dichloromethane (1 mL) was added pyridine (1 mL) and DMAP (0.2 g, 1.6 mmol). Phenyl thionochloroformate (0.44 mL, 3.2 mmol) was added dropwise. The mixture was left to stir at room temperature for 18 h. The reaction mixture was treated with cold 0.1 M hydrochloric acid and extracted with dichloromethane. Combined organic layers were dried over sodium sulphate, filtered and the filtrate was evaporated to give an oily residue. It was purified by silica gel chromatography eluting with isopropyl alcohol in dichloromethane (0-10%) to afford product (130 mg). ESMS MH+1383

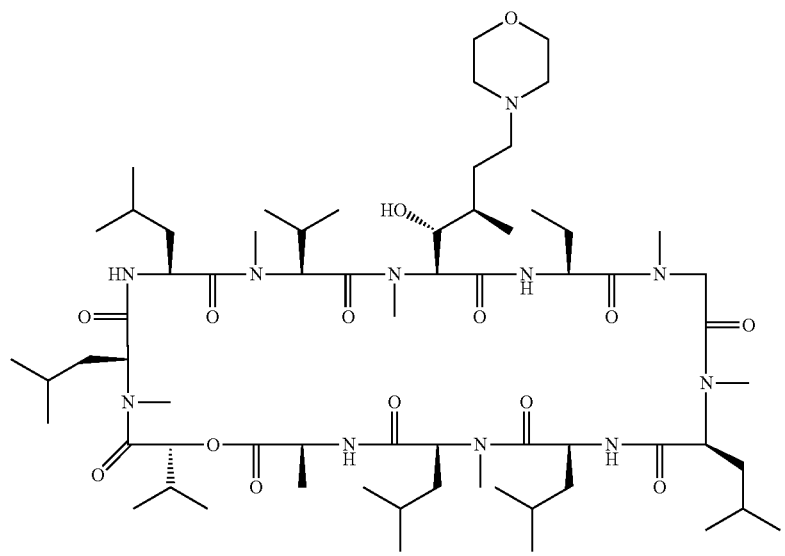 [SMILES: CC[C@H]1NC(=O)[C@@H]([C@H](O)[C@H](C)CCN2CCOCC2)N(C)C(=O)[C@@H](C(C)C)N(C)C(=O)[C@@H](CC(C)C)NC(=O)[C@@H](CC(C)C)N(C)C(=O)[C@H](C(C)C)OC(=O)[C@@H](C)NC(=O)[C@@H](CC(C)C)N(C)C(=O)[C@@H](CC(C)C)NC(=O)[C@H](CC(C)C)N(C)C(=O)CN(C)C1=O]

i) Preparation of cyclo-[MeBmt-(O-phenoxythiocarbonyl-Thr)-Sar-MeLeu-Leu-MeLeu-Ala-D-Hiv-Me-Leu-Leu-MeVal]

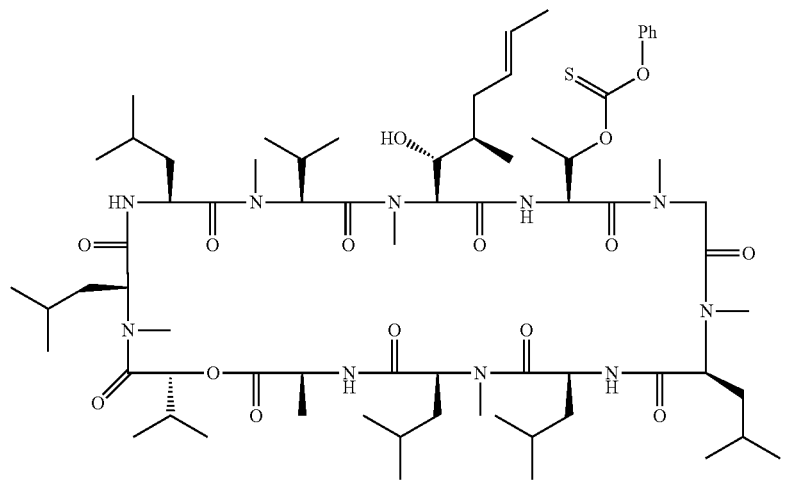 [SMILES: C/C=C/C[C@@H](C)[C@@H](O)[C@@H]1C(=O)N[C@H](C(C)OC(=S)Oc2ccccc2)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N1C]

ii) Preparation of cyclo-(MeBmt-Abu-Sar-MeLeu-Leu-MeLeu-Ala-D-Hiv-MeLeu-Leu-MeVal)

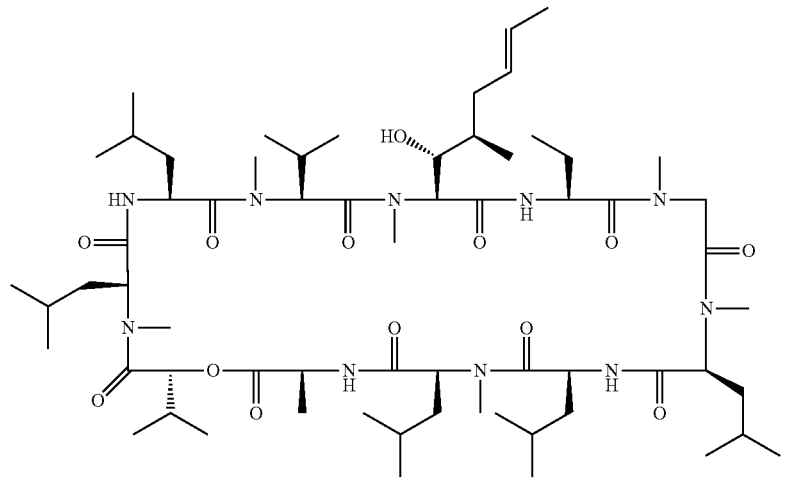 [SMILES: C/C=C/C[C@@H](C)[C@@H](O)[C@@H]1C(=O)N[C@H](CC)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N1C]

To a solution of cyclo-[MeBmt-(O-phenoxythiocarbonyl-Thr)-Sar-MeLeu-Leu-MeLeu-Ala-D-Hiv-MeLeu-Leu-MeVal] (Example 13, step i) (130 mg, 0.09 mmol) in anhydrous toluene (1 mL) was added tributyltin hydride (82 mg, 0.28 mmol) and AIBN (5 mg). The reaction vial was capped and the contents were purged with nitrogen. It was heated at 100° C. for 6 h. The reaction mixture was purified on a silica gel column by eluting it with isopropyl alcohol in dichloromethane (0-10%) to afford the product (81 mg). ESMS MH+1231 iii) Preparation of cyclo-[(3R,4R,5S)-4-(hydroxy)-3-methyl-5-(methylamino)-1-oxo-hexanoic acid-Abu-Sar-MeLeu-Leu-MeLeu-Ala-D-Hiv-MeLeu-Leu-MeVal]

The titled compound was prepared by the method of Example 2 (Step i) using cyclo-(MeBmt-Abu-Sar-MeLeu-Leu-MeLeu-Ala-D-Hiv-MeLeu-Leu-MeVal) (Example 13, step ii) to afford the product (93 mg) as an aldehyde-lactol mixture. ESMS MH+1201 (M$^+$-H$_2$O)

Example 13

Preparation of cyclo-[(3R,4R,5S)-4-(hydroxy)-3-methyl-5-(methylamino)-1-N-morpholino-hexanoic acid-Abu-Sar-MeLeu-Leu-MeLeu-Ala-D-Hiv-MeLeu-Leu-MeVal]

The titled compound was prepared by the method of Example 2 (Step ii) using cyclo-{[(3R,4R,5S)-4-(hydroxy)-3-methyl-5-(methylamino)-1-oxo-hexanoic acid-Abu-Sar-MeLeu-Leu-MeLeu-Ala-D-Hiv-MeLeu-Leu-MeVal]} (Example 13, step iii) and morpholine to afford the product (28 mg). ESMS MH+1290.5

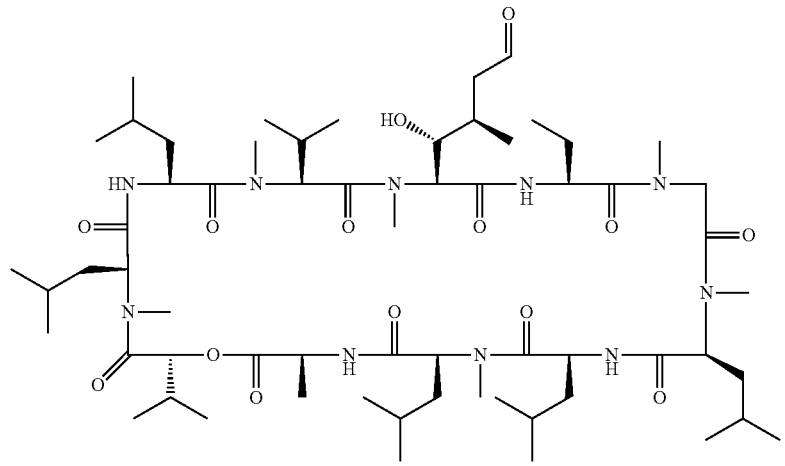 [SMILES: CC[C@H]1NC(=O)[C@@H]([C@H](O)[C@H](C)CC=O)N(C)C(=O)[C@@H](C(C)C)N(C)C(=O)[C@@H](CC(C)C)NC(=O)[C@@H](CC(C)C)N(C)C(=O)[C@H](C(C)C)OC(=O)[C@@H](C)NC(=O)[C@@H](CC(C)C)N(C)C(=O)[C@@H](CC(C)C)NC(=O)[C@H](CC(C)C)N(C)C(=O)CN(C)C1=O]

Example 14

Preparation of cyclo-[(3R,4R,5S)-4-(hydroxy)-3-methyl-5-(methylamino)-1-(6-methyl-pyridin-2-yl)-hept-1-enoic acid-Thr-Sar-MeLeu-Leu-MeLeu-Ala-D-Hiv-MeLeu-Leu-MeVal]

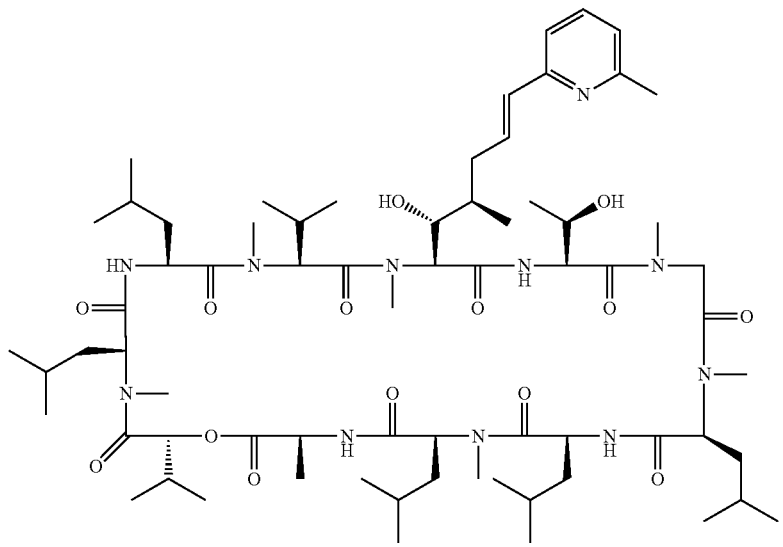 [SMILES: Cc1cccc(/C=C/C[C@@H](C)[C@@H](O)[C@@H]2C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N2C)n1]

To a solution of (6-methyl-pyridin-2-ylmethyl)-triphenyl-phosphonium bromide (131 mg, 0.29 mmol) in anhydrous THF (1 mL) at −78° C. under nitrogen, was added a 0.6 M solution of NaHMDS in toluene (0.4 mL). The mixture was left to stir from −78° C. to −30° C. over 40 min. It was re-cooled to −78° C. A solution of cyclo-[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal] (Example 2, step i) (60 mg, 49 μmol) in anhydrous THF (1 mL) was added dropwise. The resulting mixture was left to stir at room temperature for 72 h. It was treated with saturated ammonium chloride and extracted with dichloromethane. The organic layer was collected and evaporated. The crude oily residue was eluted on a silica gel column (10 g SiO$_2$) with isopropyl alcohol in dichloromethane (0-15%) to give the titled compound (19 mg). ESMS MH+1324

Example 15

Preparation of cyclo-{(3R,4R,5S)-4-(hydroxy)-3-methyl-5-(methylamino)-1-(pyrimidin-2-yl)-hept-1-enoic acid-Thr-Sar-MeLeu-Leu-MeLeu-Ala-D-Hiv-MeLeu-Leu-MeVal}

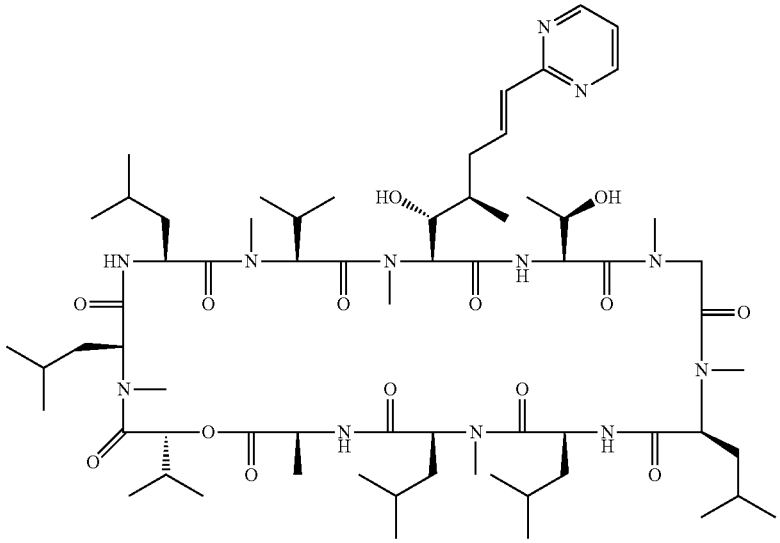 [SMILES: CC(C)C[C@@H]1C(=O)N[C@H](CC(C)C)C(=O)N(C)[C@H](C(C)C)C(=O)N(C)[C@H]([C@H](O)[C@H](C)C/C=C/c2ncccn2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 14 using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) and triphenyl-pyrimidin-2-ylmethyl-phosphonium bromide to afford the product (56 mg). ESMS MH+1311

Example 16

Preparation of cyclo-[(3R,4R,5S)-4-(hydroxy)-3-methyl-5-(methylamino)-1-(pyrimidin-2-yl)-heptanoic acid-Thr-Sar-MeLeu-Leu-MeLeu-Ala-D-Hiv-MeLeu-Leu-MeVal]

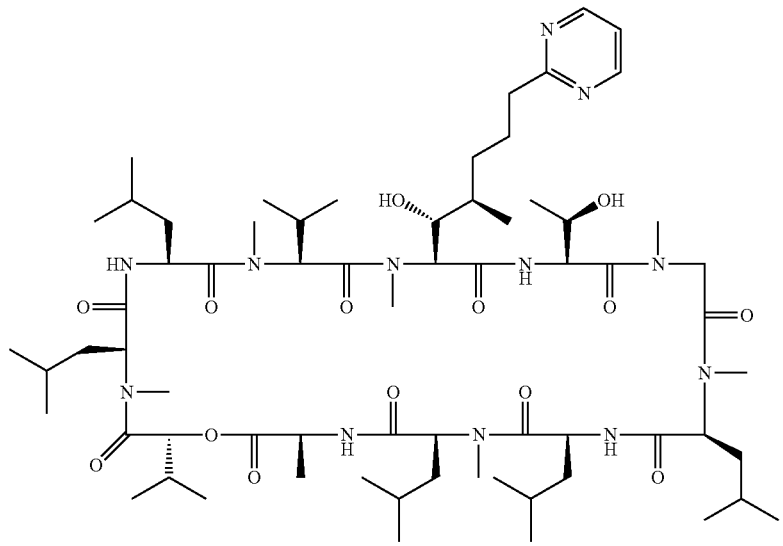 [SMILES: CC(C)C[C@@H]1C(=O)N[C@H](CC(C)C)C(=O)N(C)[C@H](C(C)C)C(=O)N(C)[C@H]([C@H](O)[C@H](C)CCCc2ncccn2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

A solution of cyclo-[(3R,4R,5S)-4-(hydroxy)-3-methyl-5-(methylamino)-1-(pyrimidin-2-yl)-hept-1-enoic acid-Thr-Sar-MeLeu-Leu-MeLeu-Ala-D-Hiv-MeLeu-Leu-MeVal] (Example 15) (49 mg, 37 μmol) in ethyl acetate (20 mL) was passed through a 10% palladium on activated carbon cartridge on an H-Cube® at 1 mL/min at room temperature. The solution was evaporated and dried under reduced pressure to afford the product as colourless solid (27 mg). ESMS MH+1313.6

Example 17

Preparation of cyclo-[(3R,4R,5S)-4-(hydroxy)-3-methyl-5-(methylamino)-1-(6-methyl-pyridin-2-yl)-heptanoic acid-Thr-Sar-MeLeu-Leu-MeLeu-Ala-D-Hiv-MeLeu-Leu-MeVal]

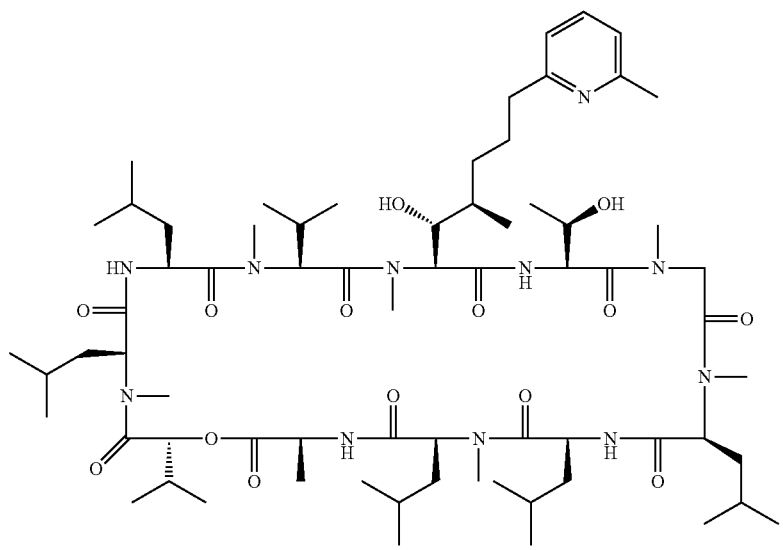 [SMILES: Cc1cccc(CCC[C@@H](C)[C@@H](O)[C@@H]2C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N2C)n1]

The titled compound was prepared by the method of Example 16 using cyclo-[(3R,4R,5S)-4-(hydroxy)-3-methyl-5-(methylamino)-1-(6-methyl-pyridin-2-yl)-hept-1-enoic acid-Thr-Sar-MeLeu-Leu-MeLeu-Ala-D-Hiv-MeLeu-Leu-MeVal] (Example 14) to afford the product (30 mg). ESMS MH+1326.7

Example 18

Preparation of cyclo-{(3R,4R,5S)-4-(hydroxy)-3-methyl-5-(methylamino)-1-(6-morpholin-4-yl-pyridin-2-yl)-hept-1-enoic acid-Thr-Sar-MeLeu-Leu-MeLeu-Ala-D-Hiv-MeLeu-Leu-MeVal}

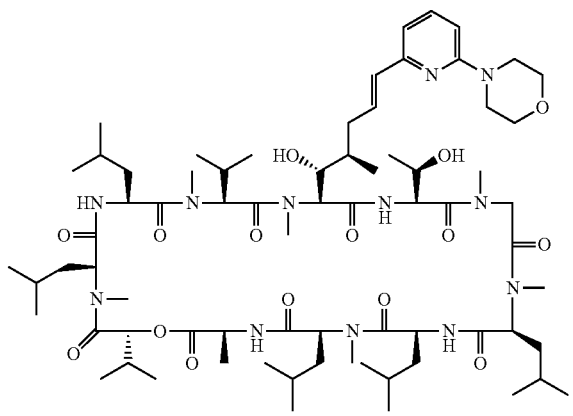 [SMILES: CC(C)C[C@@H]1C(=O)N[C@H](CC(C)C)C(=O)N(C)[C@H](C(C)C)C(=O)N(C)[C@H]([C@H](O)[C@H](C)C/C=C/c2cccc(N3CCOCC3)n2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 14 using cyclo-[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal] (Example 2, step i) and (6-morpholin-4-yl-pyridin-2-ylmethyl)-triphenyl-phosphonium bromide to afford the product (47 mg). ESMS MH+1395

Example 19

Preparation of cyclo-[(3R,4R,5S)-4-(hydroxy)-3-methyl-5-(methylamino)-1-(6-methyl-pyridin-2-yl)-hept-1-enoic acid-Abu-Sar-MeLeu-Leu-MeLeu-Ala-D-Hiv-MeLeu-Leu-MeVal]

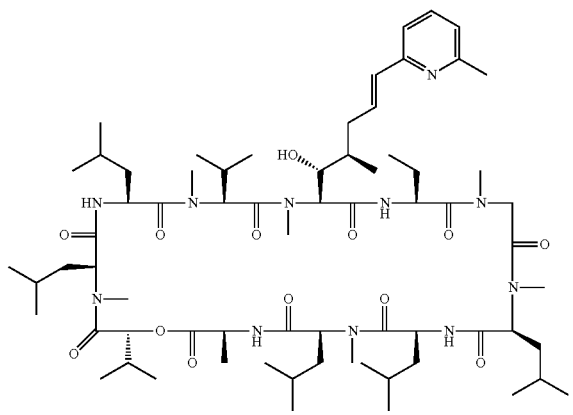

The titled compound was prepared by the method of Example 14 using cyclo-[(3R,4R,5S)-4-(hydroxy)-3-methyl-5-(methylamino)-1-oxo-hexanoic acid-Abu-Sar-MeLeu-Leu-MeLeu-Ala-D-Hiv-MeLeu-Leu-MeVal] (Example 13, Step iii) and (6-methyl-pyridin-2-ylmethyl)-triphenyl-phosphonium bromide to afford the product (7 mg). ESMS MH+1308.8

Example 20

Preparation of cyclo-[(3R,4R,5S)-4-(hydroxy)-3-methyl-5-(methylamino)-1-(6-morpholin-4-yl-pyridin-2-yl)-heptanoic acid-Thr-Sar-MeLeu-Leu-MeLeu-Ala-D-Hiv-MeLeu-Leu-MeVal]

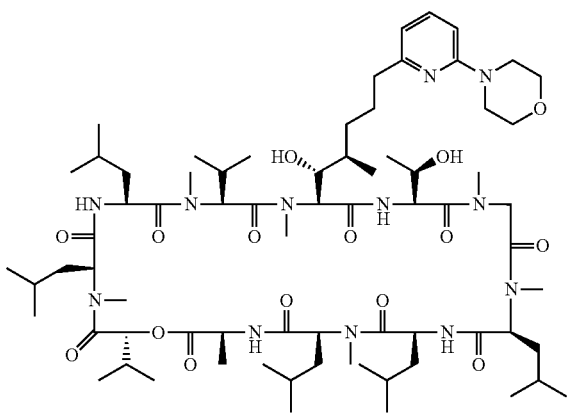 [SMILES: CC(C)C[C@@H]1C(=O)N[C@H](CC(C)C)C(=O)N(C)[C@H](C(C)C)C(=O)N(C)[C@H]([C@H](O)[C@H](C)CCCc2cccc(N3CCOCC3)n2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 16 using cyclo-[(3R,4R,5S)-4-(hydroxy)-3-methyl-5-(methylamino)-1-(6-morpholin-4-yl-pyridin-2-yl)-hept-1-enoic acid-Thr-Sar-MeLeu-Leu-MeLeu-Ala-D-Hiv-MeLeu-Leu-MeVal] (Example 18). to afford the product (33 mg). ESMS MH+1397

Example 21

Preparation of cyclo-[(3R,4R,5S)-4-(hydroxy)-3-methyl-5-(methylamino)-1-(6-methyl-pyridin-2-yl)-heptanoic acid-Abu-Sar-MeLeu-Leu-MeLeu-Ala-D-Hiv-MeLeu-Leu-MeVal]

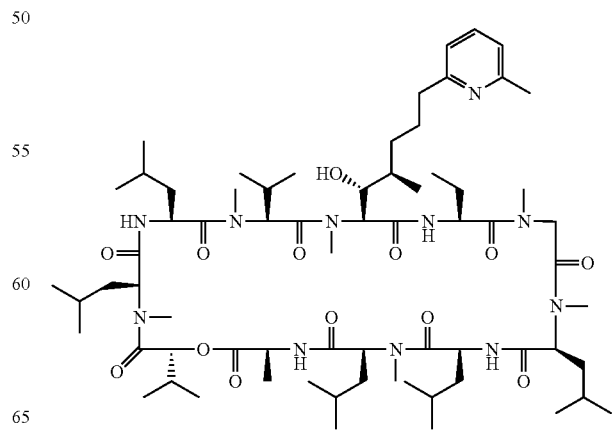

The titled compound was prepared by the method of Example 16 using cyclo-[(3R,4R,5S)-4-(hydroxy)-3-methyl-5-(methylamino)-1-(6-methyl-pyridin-2-yl)-hept-1-enoic acid-Abu-Sar-MeLeu-Leu-MeLeu-Ala-D-Hiv-MeLeu-Leu-MeVal] (Example 19) to afford the product (5.3 mg). ESMS MH+1310.7

Example 22

Preparation of cyclo-[(3R,4R,5S)-4-(hydroxy)-3-methyl-5-(methylamino)-1-N-(8-oxa-3-aza-bicyclo[3.2.1]octane)-hexanoic acid-Thr-Sar-MeLeu-Leu-MeLeu-Ala-D-Hiv-MeLeu-Leu-MeVal]

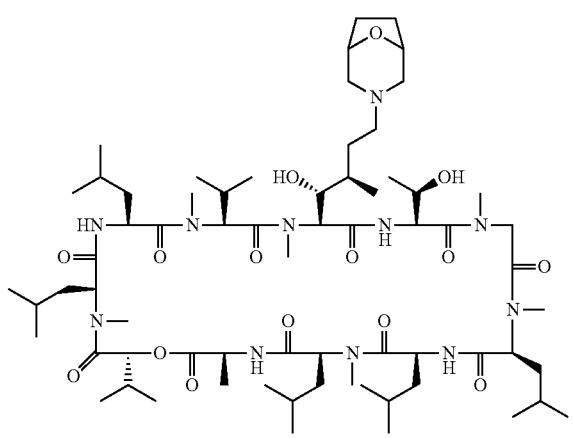 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CC3CCC(C2)O3)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

Dry dichloromethane (10 mL) was added to a mixture of cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.080 g, 0.065 mmol) and 8-oxa-3-aza-bicyclo[3.2.1]octane (0.097 g, 0.65 mmol). The mixture was stirred at room temperature for 10 min, and then the solvent was evaporated (repeated twice). Dry dichloromethane (10 mL) was added and followed by triethylamine (0.090 mL, 0.65 mmol), and sodium triacetoxyborohydride (0.137 g, 0.65 mmol). The reaction mixture was stirred at 40° C. for 18 h. The reaction mixture was diluted with dichloromethane, washed with a saturated aqueous solution of sodium bicarbonate, and then the organic phase was separated and evaporated. The residue was purified by SCX chromatography using a solvent gradient of 100% ethanol to 2 M trimethylamine in ethanol followed by MPLC chromatography using a solvent gradient of 100% dichloromethane to 85% dichloromethane/15% ethanol to give 37 mg of title compound as a white solid. ESMS MH+1332.5

Example 23

Preparation of cyclo-[(3R,4R,5S)-4-(hydroxy)-3-methyl-5-(methylamino)-1-N-(thiomorpholine 1,1-dioxide)-hexanoic acid-Thr-Sar-MeLeu-Leu-MeLeu-Ala-D-Hiv-MeLeu-Leu-MeVal]

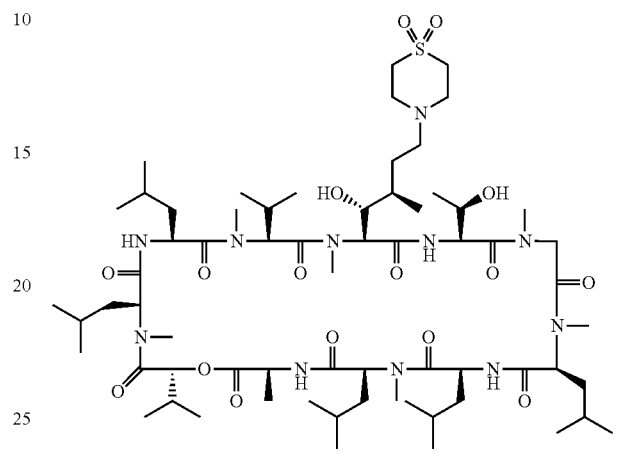

The titled compound was prepared by the method of Example 22 using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.070 g, 0.057 mmol) and thiomorpholine 1,1-dioxide (0.077 g, 0.57 mmol) to afford the product (11 mg). ESMS MH$^+$ 1355.4

Example 24

Preparation of cyclo-[(3R,4R,5S)-4-(hydroxy)-3-methyl-5-(methylamino)-1-N-(4,4-difluoro-piperidine)-hexanoic acid-Thr-Sar-MeLeu-Leu-MeLeu-Ala-D-Hiv-MeLeu-Leu-MeVal]

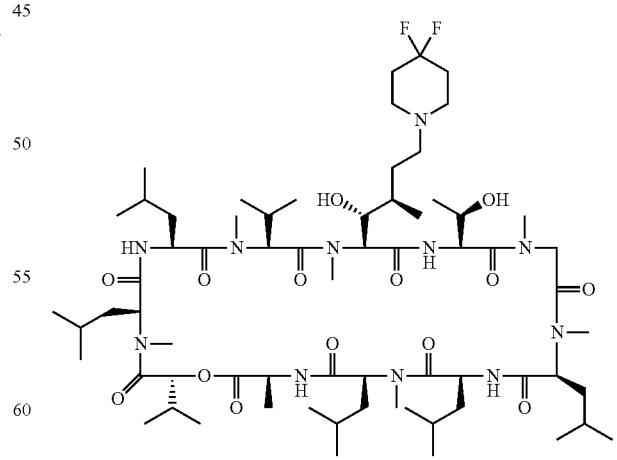

The titled compound was prepared by the method of Example 22 using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.070 g, 0.057 mmol) and 4,4-difluoropiperidine (0.089 g, 0.57 mmol) to afford the product (40 mg). ESMS MH+1340.6

Example 25

Preparation of cyclo-[(3R,4R,5S)-4-(hydroxy)-3-methyl-5-(methylamino)-1-N-((4-fluoro-piperidin-4-yl)-methanol)-hexanoic acid-Thr-Sar-MeLeu-Leu-MeLeu-Ala-D-Hiv-MeLeu-Leu-MeVal]

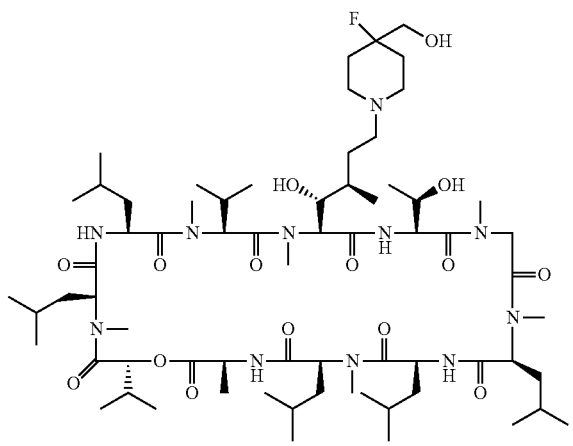 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCC(F)(CO)CC2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 22 using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.070 g, 0.057 mmol) and (4-fluoro-piperidin-4-yl)-methanol (0.096 g, 0.57 mmol) to afford the product (37 mg). ESMS MH+1353.8

Example 26

Preparation of cyclo-[(3R,4R,5S)-4-(hydroxy)-3-methyl-5-(methylamino)-1-N—((S)-1-Pyrrolidin-2-yl-methanol)-hexanoic acid-Thr-Sar-MeLeu-Leu-MeLeu-Ala-D-Hiv-MeLeu-Leu-MeVal]

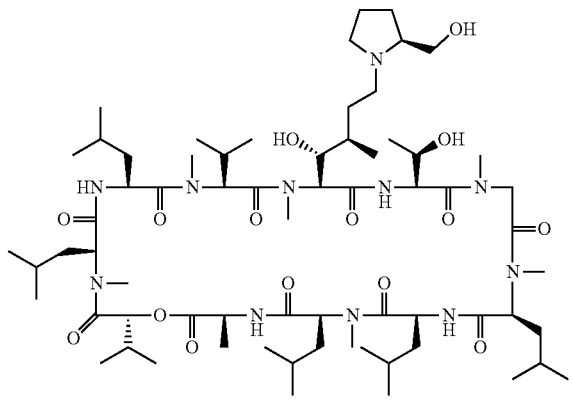 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCC[C@H]2CO)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 22 using cyclo-{[(3R,4R,5S)-4-(hydroxy)-3-methyl-5-(methylamino)-1-oxo-hexanoic acid-Thr-Sar-Me-Leu-Leu-MeLeu-Ala-D-Hiv-MeLeu-Leu-MeVal]} (Example 2, step i) (0.060 g, 0.049 mmol) and (S)-1-Pyrrolidin-2-yl-methanol (0.049 g, 0.49 mmol) to afford the product (44 mg). ESMS MH+1320.5

Example 27

Preparation of cyclo-[(3R,4R,5S)-4-(hydroxy)-3-methyl-5-(methylamino)-1-N-(3-methylamino-propionitrile)-hexanoic acid-Thr-Sar-MeLeu-Leu-MeLeu-Ala-D-Hiv-MeLeu-Leu-MeVal]

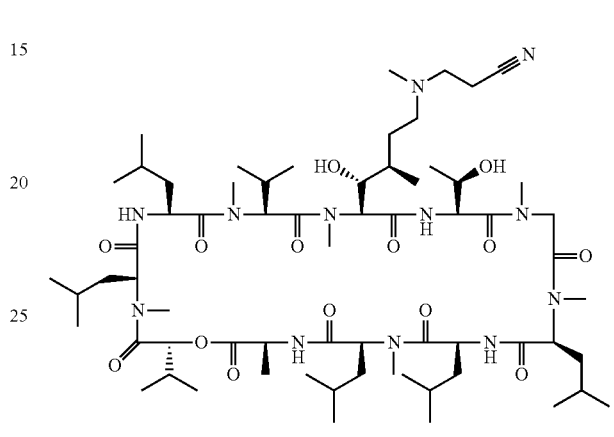

The titled compound was prepared by the method of Example 22 using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.060 g, 0.049 mmol) and 3-methylaminopropionitrile (0.041 g, 0.49 mmol) to afford the product (41 mg). ESMS MH+1303.6

Example 28

Preparation of cyclo-[(3R,4R,5S)-4-(hydroxy)-3-methyl-5-(methylamino)-1-N-(methyl-pyridin-2-yl-amine)-hexanoic acid-Thr-Sar-MeLeu-Leu-MeLeu-Ala-D-Hiv-MeLeu-Leu-MeVal]

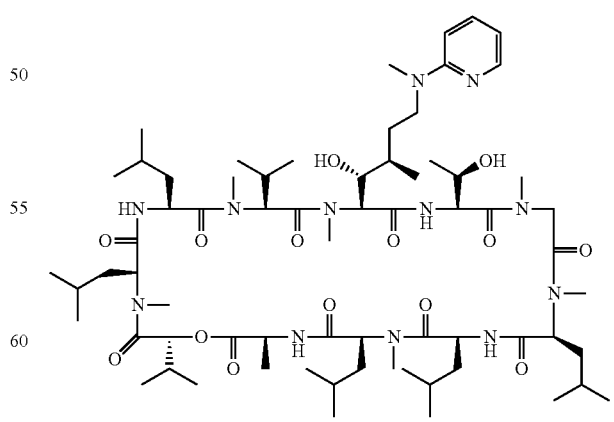

The titled compound was prepared by the method of Example 22 using cyclo-{[(3R,4R,5S)-4-(hydroxy)-3-methyl-5-(methylamino)-1-oxo-hexanoic acid-Thr-Sar-Me- Leu-Leu-MeLeu-Ala-D-Hiv-MeLeu-Leu-MeVal]} (Example 2, step i) (0.050 g, 0.040 mmol) and methyl-pyridin-2-yl-amine (0.044 g, 0.40 mmol) to afford the product (17 mg). ESMS MH+1327.6

Example 29

Preparation of cyclo-[(3R,4R,5S)-4-(hydroxy)-3-methyl-5-(methylamino)-1-N—((R)-3-Methyl-morpholine)-hexanoic acid-Thr-Sar-MeLeu-Leu-MeLeu-Ala-D-Hiv-MeLeu-Leu-MeVal]

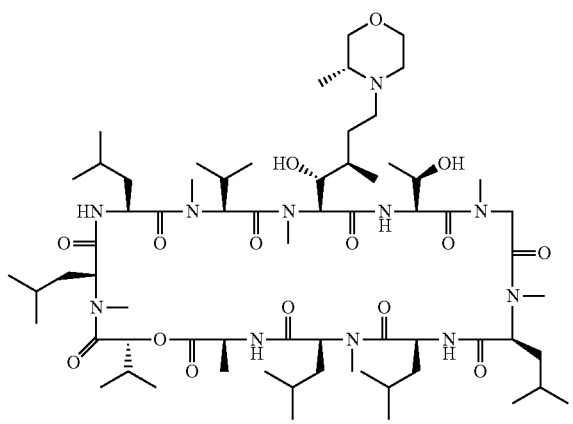 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCOC[C@H]2C)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 22 using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.050 g, 0.040 mmol) and (R)-3-methyl-morpholine (0.041 g, 0.40 mmol) to afford the product (31 mg). ESMS MH+1320.7

Example 30

Preparation of cyclo-[(3R,4R,5S)-4-(hydroxy)-3-methyl-5-(methylamino)-1-N-(bis-pyridin-2-ylmethyl-amine)-hexanoic acid-Thr-Sar-MeLeu-Leu-MeLeu-Ala-D-Hiv-MeLeu-Leu-MeVal]

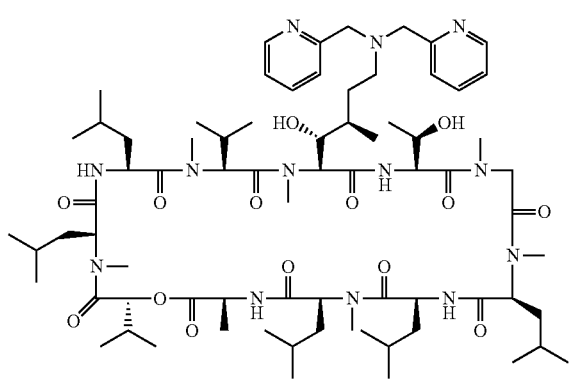 [SMILES: CC(C)C[C@@H]1C(=O)N[C@H](CC(C)C)C(=O)N(C)[C@H](C(C)C)C(=O)N(C)[C@H]([C@H](O)[C@H](C)CCN(Cc2ccccn2)Cc2ccccn2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 22 using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.058 g, 0.047 mmol) and bis-pyridin-2-ylmethyl-amine (0.094 g, 0.47 mmol) to afford the product (16 mg). ESMS MH+1418.5

Example 31

Preparation of cyclo-[(3R,4R,5S)-4-(hydroxy)-3-methyl-5-(methylamino)-1-N-(methyl-pyridin-2-ylmethyl-amino)-hexanoic acid-Thr-Sar-MeLeu-Leu-MeLeu-Ala-D-Hiv-MeLeu-Leu-MeVal]

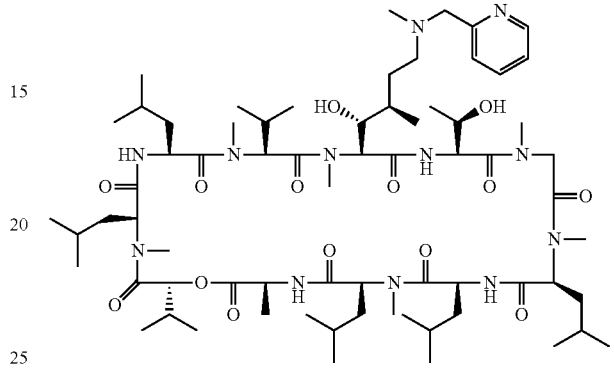

The titled compound was prepared by the method of Example 2, step ii using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.132 g, 0.108 mmol) and methyl-pyridin-2-ylmethyl-amine (0.092 g, 0.753 mmol) to afford the product (20 mg). ESMS MH+1341.6

Example 32

Preparation of cyclo-[(3R,4R,5S)-4-(hydroxy)-3-methyl-5-(methylamino)-1-N—(N'-methylpiperazine)-hexanoic acid-Thr-Sar-MeLeu-Leu-MeLeu-Ala-D-Hiv-MeLeu-Leu-MeVal]

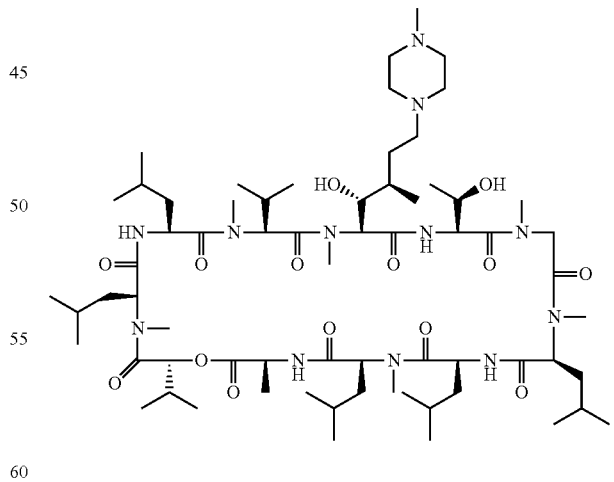

The titled compound was prepared by the method of Example 2, step ii using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.070 g, 0.057 mmol) and N-methyl piperazine (0.040 g, 0.397 mmol) to afford the product (27 mg). ESMS MH+1317.3

Example 33

Preparation of cyclo-[(2R,3R,4S)-1-(1H-benzoimidazol-2-yl)-2-methyl-4-methylamino-3-hydroxypentanoic acid-Thr-Sar-MeLeu-Leu-MeLeu-Ala-D-Hiv-MeLeu-Leu-MeVal]

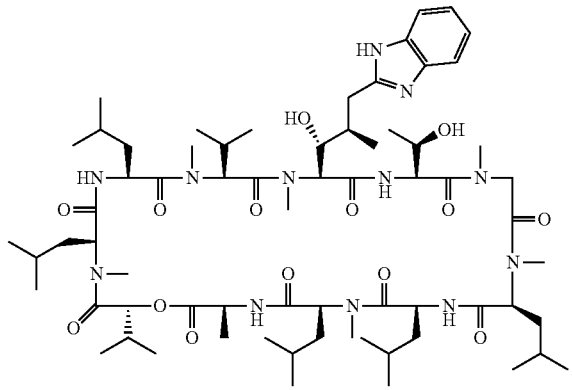 [SMILES: CC(C)C[C@@H]1C(=O)N[C@H](CC(C)C)C(=O)N(C)[C@H](C(C)C)C(=O)N(C)[C@H]([C@H](O)[C@H](C)Cc2nc3ccccc3[nH]2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

i) Preparation of cyclo-[(5R,6R,7S)-5-methyl-7-methylamino-6-triethylsilanyloxy-oct-2-enoic acid-(2S,3S)-2-amino-3-triethylsilanyloxy-butyric acid-Sar-MeLeu-Leu-MeLeu-Ala-D-Hiv-MeLeu-Leu-MeVal]

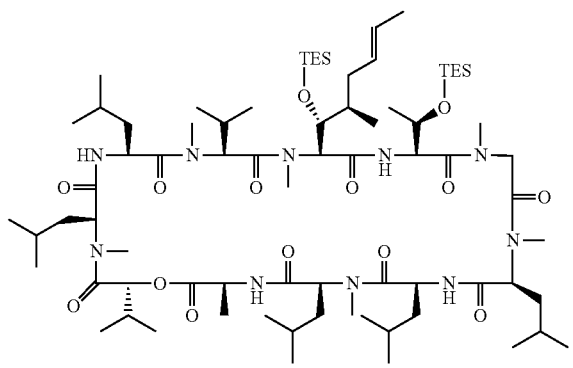

To a stirred solution of cyclo-(MeBmt-Thr-Sar-MeLeu-Leu-MeLeu-Ala-D-Hiv-MeLeu-Leu-MeVal) (Example 1) (1.17 g, 940 μmol) in dry dichloromethane (12 mL), was added triethylamine (261 μL, 1.9 mmol) and triethylsilyl trifluoromethanesulfonate (424 μL, 1.9 mmol), and the reaction was stirred for 16 hours. After this time, additional triethylamine (523 μL, 3.8 mmol) and triethylsilyl trifluoromethanesulfonate (848 μL, 3.8 mmol) and the reaction was stirred for 4 hours. After this time, water (10 mL) was added and the layers were separated using a phase-sep cartridge. The organics were concentrated under reduced pressure, and purified by MPLC using a solvent gradient of 100% isohexane to 40% acetone/60% isohexane, to give the title compound. ESMS MH+1476.3

$^1$H NMR (300 MHz, CDCl$_3$) gave 4 characteristic NH amide peaks at 8.10 (d, 1H), 7.96 (d, 1H), 6.97 (d, 1H), 6.85 (d, 1H)

ii) Preparation of cyclo[(3R,4R,5S)-4-hydroxy-3-methyl-5-methylamino-1-oxo-hexanoic acid-(2S,3S)-2-amino-3-triethylsilanyloxy-butyric acid-Sar-MeLeu-Leu-MeLeu-Ala-D-Hiv-MeLeu-Leu-MeVal]

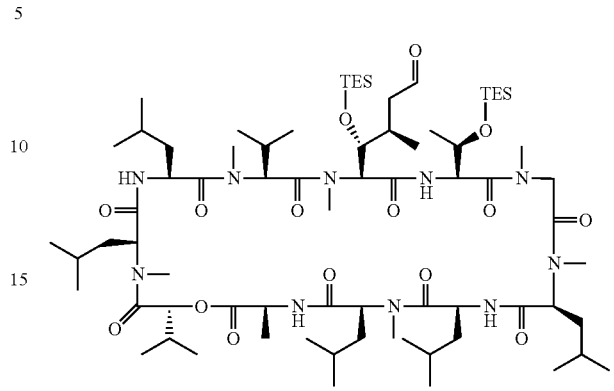

The product obtained in cyclo-[(5R,6R,7S)-5-methyl-7-methylamino-6-triethylsilanyloxy-oct-2-enoic acid-(2S,3S)-2-amino-3-triethylsilanyloxy-butyric acid-Sar-MeLeu-Leu-MeLeu-Ala-D-Hiv-MeLeu-Leu-MeVal] (Example 33, step i) (500 mg, 339 μmol) was dissolved in dry dichloromethane (50 ml) and added to a 3-neck flask equipped with a glass inlet tube (for nitrogen/ozone addition) with an outlet connected to a Dreschler bottle containing 2 M potassium iodide solution. The reaction mixture was cooled to −78° C. using a solid CO$_2$/acetone bath under a nitrogen atmosphere. When the temperature of the reaction vessel had stabilised, ozone was bubbled through the reaction mixture until it became a pale blue colour (approx. 3-5 minutes). The ozone supply was removed and dry nitrogen gas was then bubbled through the reaction mixture until the blue colour disappeared. Dimethylsulphide (99 μL, 1.4 mmol) was then added, and the reaction mixture was allowed to warm to room temperature over 3 hours. After this time, the reaction mixture was washed with brine then dried (Na$_2$SO$_4$), filtered and evaporated under reduced pressure to yield the title compound. ESMS (M+-TES) 1350.0

$^1$H NMR (300 MHz, CDCl$_3$) gave 4 characteristic NH amide peaks at 8.10 (d, 1H), 7.91 (d, 1H), 7.03 (d, 1H), 6.84 (d, 1H) along with a characteristic aldehyde peak at 9.76 (s, 1H)

iii) Preparation of cyclo-[(2R,3R,4S)-1-(1H-benzoimidazol-2-yl)-2-methyl-4-methylamino-3-triethylsilanyloxy-pentanoic acid-(2S,3S)-2-amino-3-triethylsilanyloxy-butyric acid-Sar-MeLeu-Leu-MeLeu-Ala-D-Hiv-MeLeu-Leu-MeVal]

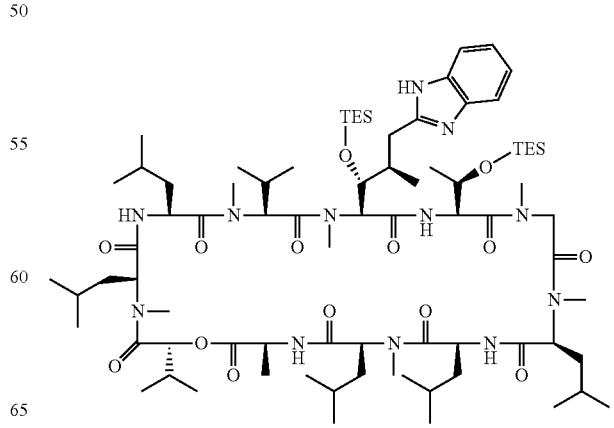

To a stirred solution of the product obtained in cyclo[(3R,4R,5S)-4-hydroxy-3-methyl-5-methylamino-1-oxo-hexanoic acid-(2S,3S)-2-amino-3-triethylsilanyloxy-butyric acid-Sar-MeLeu-Leu-MeLeu-Ala-D-Hiv-MeLeu-Leu-MeVal] (Example 33, step ii) (150 mg, 102 µmol) in acetonitrile (3 mL) was added 1,2-benzenediamine (11 mg, 102 µmol), and the reaction was stirred for 168 hours at room temperature while a stream of compressed air was bubbled through. The reaction was concentrated under reduced pressure, and the residue was purified by MPLC using a solvent gradient of 100% dichloromethane to 10% isopropanol/90% dichloromethane, to give the title compound. ESMS (M+H) 1552.8

Example 33

Preparation of cyclo-[(2R,3R,4S)-1-(1H-benzoimidazol-2-yl)-2-methyl-4-methylamino-3-hydroxy-pentanoic acid-Thr-Sar-MeLeu-Leu-MeLeu-Ala-D-Hiv-MeLeu-Leu-MeVal]

To a stirred solution of the product obtained in cyclo-[(2R,3R,4S)-1-(1H-benzoimidazol-2-yl)-2-methyl-4-methylamino-3-triethylsilanyloxy-pentanoic acid-(2S,3S)-2-amino-3-triethylsilanyloxy-butyric acid-Sar-MeLeu-Leu-MeLeu-Ala-D-Hiv-MeLeu-Leu-MeVal] (Example 33, step iii) (49 mg, 32 µmol) in acetonitrile (1 mL) was added triethylamine trihydrofluoride (51 µL, 320 µmol), and the reaction was stirred at room temperature for 16 hours. The reaction was concentrated under reduced pressure, and the residue was purified by MPLC using a solvent gradient of 100% dichloromethane to 20% isopropanol/80% dichloromethane, to give the title compound. ESMS (M+H) 1323.8

Example 34

Preparation of cyclo-[(3R,4R,5S)-4-(hydroxy)-3-methyl-5-(methylamino)-1-(4-phenyl-1-piperidyl)-hexanoic acid-Thr-Sar-MeLeu-Leu-MeLeu-Ala-D-Hiv-MeLeu-Leu-MeVal]

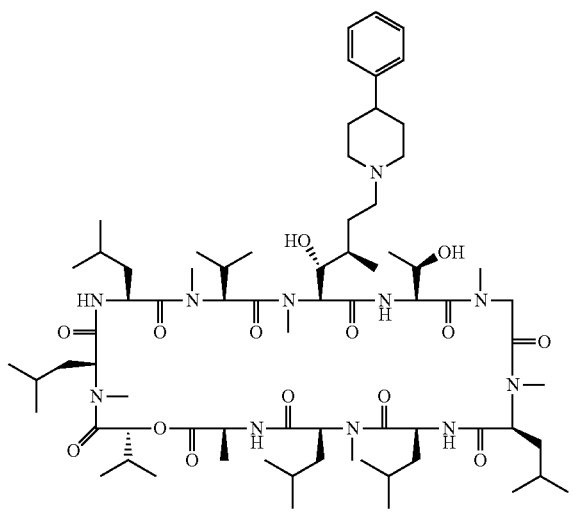 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCC(c3ccccc3)CC2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

To a stirred solution of cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (50 mg, 41 µmol) in dry dichloromethane (1 mL) was added 4-phenylpiperidine (26 mg, 162 µmol), sodium triacetoxyborohydride (51 mg, 243 µmol) and the reaction mixture was stirred at room temperature for 16 h. The reaction mixture was diluted with dichloromethane, washed with a saturated aqueous solution of sodium bicarbonate, brine and the organic phase was evaporated. The residue was purified by MPLC using a solvent gradient of 100% dichloromethane to 90% dichloromethane/10% isopropanol to give the title compound. ESMS MH$^+$ 1380.5

Example 35

Preparation of cyclo-[(3R,4R,5S)-1-benzylamino-3-methyl-5-methylamino-4-hydroxy-hexanoic acid-Thr-Sar-MeLeu-Leu-MeLeu-Ala-D-Hiv-MeLeu-Leu-MeVal]

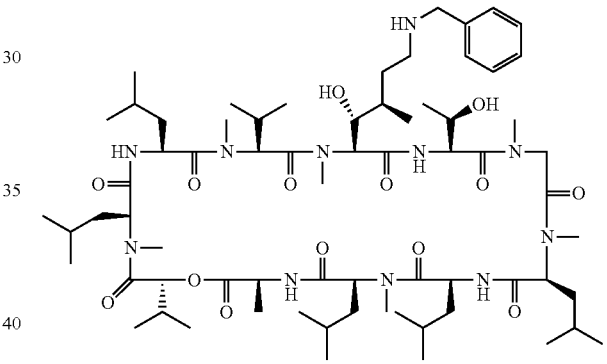

To a stirred solution of cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (120 mg, 82 µmol) in dry dichloromethane (1 ml) was added benzylamine (53 µL, 492 µmol), sodium triacetoxyborohydride (104 mg, 492 µmol) and the reaction mixture was stirred at room temperature for 16 h. The reaction mixture was diluted with dichloromethane, washed with a saturated aqueous solution of sodium bicarbonate, brine, then the organic phase was evaporated. The residue was purified by MPLC using a solvent gradient of 100% dichloromethane to 90% dichloromethane/10% isopropanol to give a crude intermediate that was dissolved in acetonitrile (1 mL) and treated with triethylamine trihydrofluoride (77 µL, 472 µmol), and stirred for 16 hours at room temperature. The reaction was concentrated under reduced pressure and purified by MPLC using a solvent gradient of 100% dichloromethane to 80% dichloromethane/20% isopropanol to give the title compound. ESMS (M+H) 1326.8

Example 36

Preparation of cyclo-[(3R,4R,5S)-1-benzylcarbamoyl-3-methyl-5-methylamino-4-hydroxy-pentanoic acid-Thr-Sar-MeLeu-Leu-MeLeu-Ala-D-Hiv-MeLeu-Leu-MeVal]

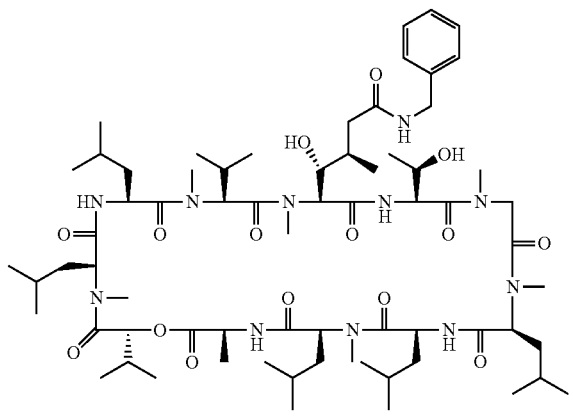 [SMILES: CC(C)C[C@@H]1C(=O)N[C@H](CC(C)C)C(=O)N(C)[C@H](C(C)C)C(=O)N(C)[C@H]([C@H](O)[C@H](C)CC(=O)NCc2ccccc2)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

i) Preparation of cyclo-[(3R,4R,5S)-3-methyl-5-methylamino-4-triethylsilanyloxy-hexanedioic acid-(2S,3S)-2-amino-3-triethylsilanyloxy-butyric acid-Sar-MeLeu-Leu-MeLeu-Ala-D-Hiv-MeLeu-Leu-MeVal]

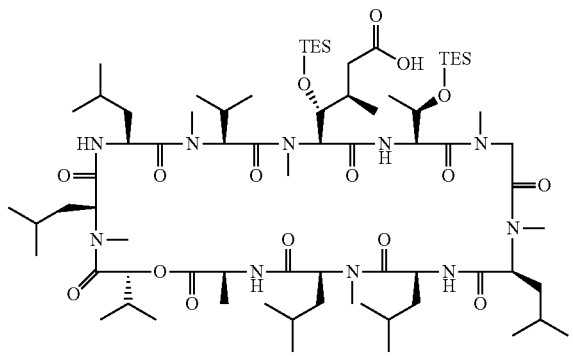

To a stirred solution of cyclo[(3R,4R,5S)-4-hydroxy-3-methyl-5-methylamino-1-oxo-hexanoic acid-(2S,3S)-2-amino-3-triethylsilanyloxy-butyric acid-Sar-MeLeu-Leu-MeLeu-Ala-D-Hiv-MeLeu-Leu-MeVal] (Example 33, step ii) (200 mg, 140 µmol) in tetrahydrofuran (1 mL) and tert-butanol (1 mL), was added 2,3-dimethylbut-2-ene (81 µL, 680 µmol), followed by a solution of dibasic sodium hydrogen phosphate (58 mg, 410 µmol) in water (0.5 mL). A solution of sodium chlorite (37 mg, 410 µmol) in water (0.5 mL) was then added and the reaction was stirred for 4 hours at room temperature. The reaction was diluted with water (10 mL) and the organics were extracted into tert-butylmethyl-ether (3×5 mL). The combined organics were dried using a phase-sep cartridge, and concentrated under reduced pressure to give the title compound. ESMS (M+-TES) 1382.8

$^1$H NMR (300 MHz, CDCl$_3$) gave 4 characteristic NH amide peaks at 8.08 (d, 1H), 7.91 (d, 1H), 7.02 (d, 1H), 6.83 (d, 1H)

ii) Preparation of cyclo-[(3R,4R,5S)-1-benzylcarbamoyl-3-methyl-5-methylamino-4-triethylsilanyloxy-pentanoic acid-(2S,3S)-2-amino-3-triethylsilanyloxy-butyric acid-Sar-MeLeu-Leu-MeLeu-Ala-D-Hiv-MeLeu-Leu-MeVal]

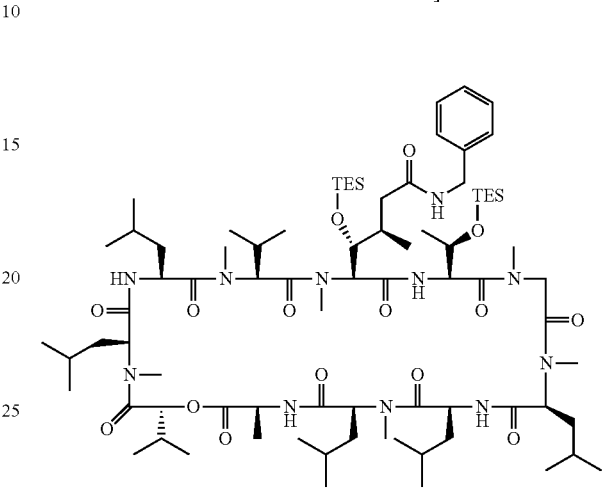

To a stirred solution of cyclo-[(3R,4R,5S)-3-methyl-5-methylamino-4-triethylsilanyloxy-hexanedioic acid-(2S,3S)-2-amino-3-triethylsilanyloxy-butyric acid-Sar-MeLeu-Leu-MeLeu-Ala-D-Hiv-MeLeu-Leu-MeVal] (Example 36, step i) (100 mg, 68 µmol) in dichloromethane (1 mL), was added triethylamine (18 µL, 135 µmol), benzylamine (15 µL, 135 µmol) and (dimethylamino)-N,N-dimethyl(3H-[1,2,3]triazolo[4,5-b]pyridin-3-yloxy)methaniminium hexafluorophosphate (26 mg, 68 µmol), the reaction was then stirred for 16 hours. The reaction was diluted with water (5 mL) and the organics separated using a phase-sep cartridge. The aqueous was re-extracted with dichloromethane (4 mL) and passed through a phase-sep cartridge. The combined organics were concentrated under reduced pressure to give the title compound as a crude intermediate which was carried forward. ESMS (M-TES+NH$_4$) 1473.0

Example 36

Preparation of cyclo-[(3R,4R,5S)-1-benzylcarbamoyl-3-methyl-5-methylamino-4-hydroxy-pentanoic acid-Thr-Sar-MeLeu-Leu-MeLeu-Ala-D-Hiv-MeLeu-Leu-MeVal]

To a stirred solution of the crude cyclo-[(3R,4R,5S)-1-benzylcarbamoyl-3-methyl-5-methylamino-4-triethylsilanyloxy-pentanoic acid-(2S,3S)-2-amino-3-triethylsilanyloxy-butyric acid-Sar-MeLeu-Leu-MeLeu-Ala-D-Hiv-MeLeu-Leu-MeVal] (Example 36, step ii) (100 mg, 64 µmol) in acetonitrile (1 mL) was added triethylamine trihydrofluoride (52 µL, 320 µmol) and the reaction was stirred for 16 hours. Additional triethylamine trihydrofluoride (52 µL, 320 µmol) was added and the reaction stirred for an additional 24 hours. Additional triethylamine trihydrofluoride (105 µL, 640 µmol) was added and the reaction was stirred for an additional 72 hours. The reaction was concentrated under reduced pressure, and purified by MPLC eluting with 100% dichloromethane to 12% isopropanol/88% dichloromethane to give the title compound. ESMS (M+H) 1340.6

Example 37

Preparation of cyclo-[(3R,4R,5S)-4-hydroxy-1-isopropylamino-3-methyl-5-methylamino-hexanoic acid-Thr-Sar-MeLeu-Leu-MeLeu-Ala-D-Hiv-MeLeu-Leu-MeVal]

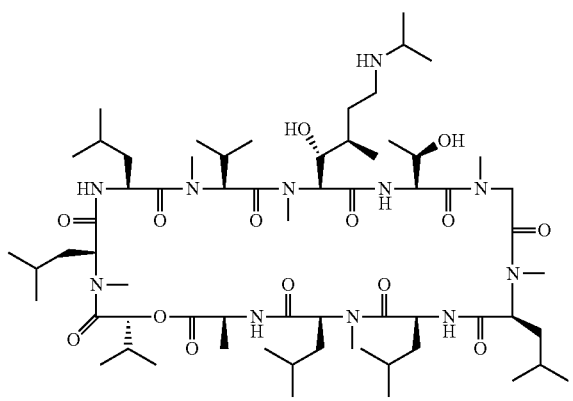 [SMILES: CC(C)C[C@@H]1C(=O)N[C@H](CC(C)C)C(=O)N(C)[C@H](C(C)C)C(=O)N(C)[C@H]([C@H](O)[C@H](C)CCNC(C)C)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

To a stirred solution of cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (240 mg, 194 μmol) in dry dichloromethane (2 ml) was added isopropylamine (69 mg, 1.2 mmol), sodium triacetoxyborohydride (250 mg, 1.2 mmol) and the reaction mixture was stirred at room temperature for 72 h. The reaction mixture was diluted with dichloromethane, washed with a saturated aqueous solution of sodium bicarbonate, brine and then the organic phase was evaporated. The residue was purified by SCX chromatography using a solvent gradient of 100% ethanol to 0.21M trimethylamine in ethanol to give the title compound. ESMS (M+H) 1278.6

Example 38

Preparation of cyclo-[(3R,4R,5S)-1-(acetyl-isopropyl-amino)-4-hydroxy-3-methyl-5-methylamino-hexanoic acid-Thr-Sar-MeLeu-Leu-MeLeu-Ala-D-Hiv-MeLeu-Leu-MeVal]

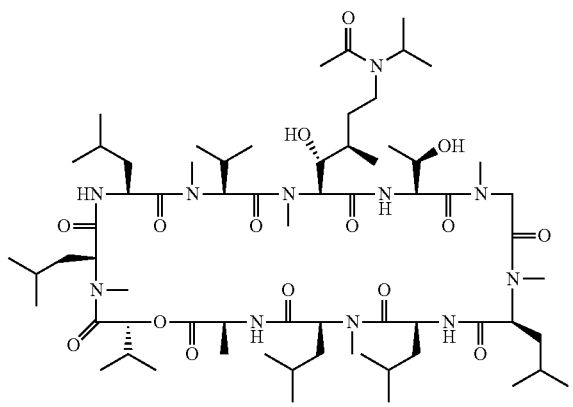 [SMILES: CC(=O)N(CC[C@@H](C)[C@@H](O)[C@@H]1C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N(C)[C@H](CC(C)C)C(=O)N[C@H](CC(C)C)C(=O)N(C)[C@H](C(C)C)C(=O)N1C)C(C)C]

To a stirred solution of cyclo-[(3R,4R,5S)-4-hydroxy-1-isopropylamino-3-methyl-5-methylamino-hexanoic acid-Thr-Sar-MeLeu-Leu-MeLeu-Ala-D-Hiv-MeLeu-Leu-MeVal] (Example 37) (81 mg, 63 μmol) in dichloromethane (2 mL) was added triethylamine (53 μL, 39 mg, 380 μmol) followed by acetyl chloride (27 μL, 30 mg, 380 μmol), and the reaction mixture was stirred at room temperature for 1 h. The reaction mixture was concentrated under reduced pressure and then partitioned between dichloromethane (2 mL) and water (2 mL). The organics were separated using a hydrophobic frit, and purified by SCX chromatography using 100% ethanol to give the title compound. ESMS (M+H) 1320.7

Example 39

Preparation of cyclo-[(2R,3R,4S)-4-hydroxy-1-(2-hydroxymethyl-piperidin-1-yl)-3-methyl-5-methylamino-hexanoic acid-Thr-Sar-MeLeu-Leu-MeLeu-Ala-D-Hiv-MeLeu-Leu-MeVal]

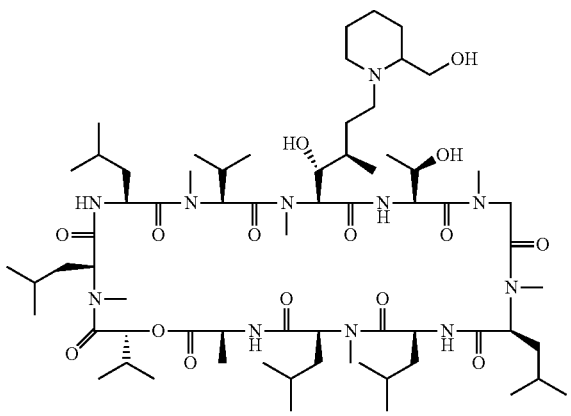 [SMILES: CC(C)C[C@@H]1C(=O)N[C@H](CC(C)C)C(=O)N(C)[C@H](C(C)C)C(=O)N(C)[C@H]([C@H](O)[C@H](C)CCN2CCCCC2CO)C(=O)N[C@H]([C@@H](C)O)C(=O)N(C)CC(=O)N(C)[C@@H](CC(C)C)C(=O)N[C@H](CC(C)C)C(=O)N(C)[C@H](CC(C)C)C(=O)N[C@H](C)C(=O)O[C@@H](C(C)C)C(=O)N1C]

The titled compound was prepared by the method of Example 2, step ii using cyclo-{[(3R,4R,5S)-4-(hydroxy)-3-methyl-5-(methylamino)-1-oxo-hexanoic acid-Thr-Sar-MeLeu-Leu-MeLeu-Ala-D-Hiv-MeLeu-Leu-MeVal]} (Example 2, step i) (0.070 g, 0.057 mmol) and 2-piperidinemethanol (0.039 g, 0.340 mmol) to afford the product (27 mg). ESMS MH+1334.8

Biological and Physical Properties

Example Compounds are listed and described in Table 1, below. Data showing cyclophilin A (Cyp A) inhibitory activity, cyclophilin D (Cyp D) inhibitory activity, immunosuppressive potential, and aqueous solubility for selected compounds are described in Table 1. General procedures and protocols of assays used to obtain the data are given below.

The data shows that cycloundecadepsipeptide compounds as described herein, are potent inhibitors of cyclophilin A and cyclophilin D (Ki<300 nM), as measured by the protease-free PPIase assay; have significantly less immunosuppressive activity than the compound of Example 1, as measured by the CaN assay in the presence of Cyp-A; and have water solubility at least equal to or greater than that of Example 1, as measured by the water solubility assay.

TABLE 1

| Compound | CypA Ki nM | CypD Ki nM | CaN + CypA nM | Solubility (μM) |
|---|---|---|---|---|
| Compound of formula A (Example 1) | 1.7 | 3.2 | 70 | 10-25 |
| Example 2 | 9.2 | 6.5 | >1,000 | >100 |
| Example 3 | +++ | +++ | — | 50-75 |

TABLE 1-continued

| Compound | CypA Ki nM | CypD Ki nM | CaN + CypA nM | Solubility (µM) |
|---|---|---|---|---|
| Example 4 | +++ | +++ | — | 25-50 |
| Example 5 | +++ | +++ | — | 50-75 |
| Example 6 | +++ | +++ | — | 25-50 |
| Example 7 | ++ | +++ | — | 50-75 |
| Example 8 | ++ | +++ | — | >100 |
| Example 9 | +++ | +++ | — | 10-25 |
| Example 10 | ++ | +++ | — | >100 |
| Example 11 | +++ | +++ | — | >100 |
| Example 12 | ++ | +++ | — | >100 |
| Example 13 | +++ | +++ | — | 25-50 |
| Example 14 | +++ | +++ | — | 10-25 |
| Example 15 | +++ | +++ | >1,000 | 10-25 |
| Example 16 | +++ | +++ | — | 25-50 |
| Example 17 | +++ | +++ | >1,000 | 10-25 |
| Example 18 | +++ | +++ | — | 10-25 |
| Example 19 | +++ | +++ | — | 10-25 |
| Example 20 | +++ | +++ | >5,000 | 10-25 |
| Example 21 | +++ | +++ | — | 10-25 |
| Example 22 | +++ | +++ | >10,000 | 25-50 |
| Example 23 | +++ | +++ | >10,000 | 75-100 |
| Example 24 | +++ | +++ | — | 25-50 |
| Example 25 | + | + | — | >100 |
| Example 26 | + | ++ | — | >100 |
| Example 27 | ++ | +++ | — | >100 |
| Example 28 | +++ | +++ | — | 25-50 |
| Example 29 | ++ | ++ | — | >100 |
| Example 30 | ++ | +++ | — | 10-25 |
| Example 31 | ++ | +++ | — | 50-75 |
| Example 32 | + | ++ | — | — |
| Example 33 | +++ | +++ | — | 25-50 |
| Example 34 | +++ | +++ | — | 10-25 |
| Example 35 | ++ | +++ | — | 25-50 |
| Example 36 | +++ | +++ | — | 25-50 |
| Example 37 | ++ | +++ | — | >100 |
| Example 38 | ++ | +++ | — | 50-75 |
| Example 39 | + | ++ | — | >100 |

Results of CypA and CypD screening assay of Example compounds.
+ CypA/D inhibition Ki between 100 nM to 300 nM,
++ CypA/D inhibition Ki between 25 nM to 100 nM
+++ CypA/D inhibition Ki between 1 nM to 25 nM General Procedures and Assays
*Protease-Free PPIase Assay The protease-free PPIase assay measures the rate of cis to trans conversion of a peptide substrate catalyzed by the enzymes cyclophilin A and cyclophilin D. Addition of a cyclophilin inhibitor (e.g., a test compound) slows the catalyzed rate and a $K_i$ value is obtained. A $K_i$ value of less than 30 nM demonstrates that the test compound is a potent inhibitor of cyclophilin A or cyclophilin D.

Materials
Assay Buffer:
35 mM HEPES pH 7.8, filtered through a 0.2 µm filter. 50 µM DTT was added prior to use each day and then the buffer was stored on ice.

Enzyme:
Human recombinant cyclophilin A (Cyp A) (Sigma C3805) enzyme was diluted to 1 µM with enzyme dilution buffer (20 mM HEPES pH 7.8, 40% glycerol, 50 µM DTT and 1 µM BSA) and stored at −20° C.

Substrate:
Succinimide-Ala-Ala-Pro-Phe-p-nitroanailide (SUC-AAPF-pNA) (from Bachem AG, L-1400), 20 mg/ml prepared in 0.5 M LiCl in trifluoroethanol.

Method
All readings were taken with an Agilent 8453 Spectrophotometer which consists of a cuvette holder, stirrer and chiller to maintain a stirred cuvette temperature of 10.0±0.1° C. The temperature is monitored by the use of temperature probe. To prevent UV degradation of test compounds, the light below 290 nm was blocked using a glass slide in the light path. 1.5 ml of assay buffer was put into a 3 ml quartz cuvette and cooled to 10.0±0.1° C. while stirring (vigorous but not so fast as to produce cavitation). The inhibitor was diluted in 100% DMSO, and then added to the assay to a maximum final concentration of 0.5% DMSO in the assay. A blank spectrum was obtained, then 3 µL of enzyme was added (2 nM final concentration) and then 3 µL substrate (60 µM final concentration) added. The absorbance was measured at 330 nm for 300 s or 500 s for blank runs (NOTE: the substrate must be added in one quick injection and the measurements started immediately to minimize mixing errors).

A first order rate equation was fitted to the absorbance data, for each concentration of inhibitor, to obtain the rate constant (the first 10 to 15 seconds were excluded as mixing causes errors in this portion of curve). The catalytic rate was calculated from the enzymatic rate constant minus the background rate constant. An exponential curve was generated using the catalytic rate constants versus the inhibitor concentration to obtain the $K_i$ value for the inhibitor. The $K_i$ value is indicative of the binding affinity between the test compound and cyclophilin A or cyclophilin D.

**Calcineurin Phosphatase (CaN) Assay

The calcineurin phosphatase assay is a means for estimating the immunosuppressive potential of a test compound. Calcineurin is a serine-threonine protein phosphatase that on activation dephosphorylates members of the nuclear factor of activated T cells (NFAT), which are important in T lymphocyte activation. Some cyclophilin A inhibitors, such as cyclosporin A (CsA) or compound 1, when bound to cyclophilin A (Cyp A) markedly inhibit calcineurin activity, resulting in very significant immunosuppressive effects. Alternatively, in the presence of cyclophilin A, some cyclophilin A inhibitors show reduced calcineurin inhibition and thus less immunosuppression or do not inhibit calcineurin activity at all and show no immunosuppressive effects.

To investigate the immunosuppressive potential of exemplary compounds of Formula 1, which are novel cycloundecadepsipeptide compounds, their ability to inhibit calcineurin activity was measured in the presence of Cyp A.

The CaN assay kit used is based on a colorimetric assay for measuring calcineurin phosphatase activity, and it is commercially available (Enzo Life Sciences and Calbiochem). Calmodulin is also required for calcineurin activity and RH phosphopeptide is used as an efficient peptide substrate for calcineurin. We have modified the method to enable measurement of Cyp A-dependent and Cyp A-independent inhibition of calcineurin through the addition of Cyp A in a 1:1 complex with the inhibitor. The detection of free phosphate released is based on the classic Malachite green assay.

Materials:
Enzo Life Sciences CaN Assay Kit: BML-AK804
2× assay buffer: 100 mM Tris, pH7.5, 200 mM NaCl, 12 mM MgCl$_2$, 1 mM DTT, 0.05% NP-40, 1 mM CaCl$_2$
Malachite Green: BIOMOL Green™ reagent
Calmodulin (Human, Recombinant): was thawed on ice, diluted 1:50 with 2× assay buffer, and then stored on ice.
Calcineurin: was thawed quickly, stored on ice immediately, diluted 1:12.5 with 1× assay buffer, and then stored on ice.
R-II Substrate: 915 µL ultrapure water (UPW) was added to the 1.5 mg vial substrate to give a final concentration of 0.75 mM.
Inhibitors: 2.5 mM inhibitor in 100% DMSO.
Cyp A: recombinant human CypA (Sigma C3805), 1 mg/ml; Recombinant 6-his tagged CypA prepared by the Univ. of Edinburgh was also used. Comparison of the results showed that both enzymes gave identical results.

Method

Inhibitor dilutions: inhibitor compounds were diluted in UPW in polypropylene low-binding 96 well plates at 5x the final assay concentration. For samples 'without Cyp A', a 4-point dilution series of the inhibitor was prepared in duplicate to obtain a final assay concentration of 10, 1, 0.1 and 0.01 µM. For samples 'with Cyp A', a 7-point dilution series was prepared to obtain a 1:1 complex of the inhibitor with CypA; the inhibitor and Cyp A final assay concentrations of 10, 3.33, 1.11, 0.37, 0.12, 0.04, 0.014 µM were prepared. Cs A inhibitor controls were also prepared to obtain a final concentration of 10 µM Cs A with and without 10 µM Cyp A.

Assay Setup: using the half area 96 well plates supplied with the kit, 10 µl UPW was added to duplicate wells to provide the non-inhibited control. 10 µl of the inhibitor or the inhibitor/CypA complex was added to the appropriate sample wells. 25 µl of the 2x assay buffer with CaM was added to all wells, then 5 µl of CaN was added to all wells (40 U per well final concentration) except duplicate 'no calcineurin blank' wells to which 5 µL 1x assay buffer was added. The assay plate was placed in an oven at 30° C. for 15 minutes to equilibrate to the reaction temperature. The reaction was started by the addition of 10 µl RII-peptide (0.15 mM final concentration). The reaction was allowed to proceed at 30° C. for a time period in which the reaction is linear for about 60 minutes. The reaction was then terminated by adding 100 µl of the Malachite Green reagent. The color was allowed to develop for 15-30 minutes at room temperature before the absorbance at 620 nm was measured using a plate reader (Molecular Devices—SpectraMax M5). The data were analyzed by subtracting 'no Calcineurin blank' from all the absorbance readings and plotting the background corrected absorbances against $Log_{10}$ inhibitor concentration. A sigmoidal-dose response curve was fitted to the data using GraphPad Prism Software.

The compound 1 is a potent inhibitor of calcineurin activity and therefore a potent immunosuppressive. It exerts its immunosuppressive activity by binding to cyclophilin A to form a complex, which then binds to calcineurin and thereby inhibits calcineurin activity. As shown in table 1, compound 1 has an $IC_{50}$ value of 70 nM in the calcineurin/cyclophilin A assay. Thus, compounds with values higher than 70 nM in this assay will be predictably less immunosuppressive than the compound of example 1. As can be seen from table 1, cycloundecadepsipeptide compound 2 produces significantly higher values than 70 nM in this assay and therefore are significantly less immunosuppressive than compound 1.

***Water Solubility Assay (Measured in pH 7.8 Buffer)

The aqueous solubility of compounds 1 and 2 in buffer (pH 7.8) was measured by recording the onset of precipitation of the compounds as a function of increasing concentration. The onset of precipitation, if it occurred, was detected by an increase in absorbance at 650 nm.

Materials

Assay Buffer: 35 mM HEPES pH 7.8

Stock solutions of Control and Test Compounds: 10 mM in 100% DMSO

Method 10 mM stock solutions of control and test compounds were prepared in 100% DMSO. A series of dilutions were prepared from the stock in DMSO so that the final concentrations in the assay were 0, 3.33, 10, 25, 50, 75 and 100 µM and DMSO was limited to 1%.

Assay buffer (247.5 µl) was placed into flat bottomed transparent 96-well plate. For blank samples DMSO (2.5 µl) was added. For test and control samples 2.5 µl of the appropriate DMSO dilution stocks were added to the appropriate well. All test and control compounds were performed in triplicate.

The plates were sealed with adhesive plate seal and shaken at 250 rpm at 25° C. for 18 h on a plate shaker.

After incubation the plate seals were taken off and any bubbles observed in wells removed. The plates were read on a SpectraMaxM5 with a 5 s pre-shake at 650 nm.

Data files were transferred to the appropriate worksheet and the solubility range of the compounds was calculated from the data.

The values shown in the tables indicate the concentration in µM (micromolar) at which the compound remains in solution.

As shown in table 1, the compound of example 1 has an onset of precipitation between 10-25 µM concentration of water. Compounds measured to precipitate at higher concentrations of water than 10-25 µM thus have better aqueous solubility (e.g. the compound of example 2).

Rat Pharmacokinetic Data

Rat pharmacokinetic data was obtained for example 2, following iv dosing at 1 mg/kg and po dosing at 10 mg/kg and individual analysis of plasma and whole blood samples at various time points was carried out.

Whole Blood

Following intravenous administration of the compound of example 2 at a nominal dose of 1 mg/kg, the mean value of systemic clearance was 1.16 L/hr/kg, which corresponded to 35.0% of hepatic blood flow in rats (3.31 L/hr/kg). The mean half-life ($T_{1/2}$) was 6.14 hr. The mean value of $C_{max}$ (at 5 minutes after dosing) following IV administration at a nominal dose of 1 mg/kg was 643.18 µg/L. The mean values of $AUC_{(0-t)}$ and $AUC_{(0-\infty)}$ were 826.92 and 858.75 hr*µg/L.

The mean volume of distribution at the terminal phase was 10.32 L/kg, which corresponded to 15.40-fold of the total body water (0.67 L/kg) in rats.

Following oral administration of the compound of example 2 at a dose of 10 mg/kg, the mean values of $C_{max}$ and $T_{max}$ were 678.45 ng/mL and 2.00 hr; the mean values of $AUC_{(0-t)}$ and $AUC_{(0-\infty)}$ were 5934.43 and 6021.60 ng/mL*hr; the mean value of half-life ($T_{1/2}$) was 4.03 hr. The mean value of bioavailability was 70.12%.

Plasma

Following intravenous administration of example 2 at a nominal dose of 1 mg/kg, the mean value of systemic clearance was 4.18 L/hr/kg, which corresponded to 1.26-fold of hepatic blood flow in rats (3.31 L/hr/kg). The mean half-life ($T_{1/2}$) was 4.96 hr.

The mean value of $C_{max}$ (at 5 minutes after dosing) following IV administration at a nominal dose of 1 mg/kg was 274.94 µg/L. The mean values of $AUC_{(0-t)}$ and $AUC_{(0-\infty)}$ were 197.06 and 238.98 hr*µg/L.

The mean volume of distribution at the terminal phase was 29.94 L/kg, which corresponded to 44.69-fold of the total body water (0.67 L/kg) in rats.

Following oral administration of example 2 at a dose of 10 mg/kg, the mean values of $C_{max}$ and $T_{max}$ were 328.35 ng/mL and 2.00 hr; the mean values of $AUC_{(0-t)}$ and $AUC_{(0-\infty)}$ were 2245.93 and 2291.04 ng/mL*hr; the mean value of half-life ($T_{1/2}$) was 4.40 hr. The mean value of bioavailability was 95.87%.

In whole blood, the mean volume of distribution at the terminal phase was 10.32 L/kg whereas in plasma the mean volume of distribution at the terminal phase was 29.94 L/kg, indicating only a ~3-fold difference in blood to plasma ratio. This is significantly less than the 10-40 fold blood to plasma ratio typically observed with cyclophilin inhibitors such as BC556 (Gregory M A et al, Poster presented at EASL Meeting, Barcelona, April 2012). This data suggests that compound 2 and other compounds of Formula 1 may have improved whole animal tissue distribution over many other cyclophilin inhibitors.

The invention claimed is:
1. A compound having the formula (1):

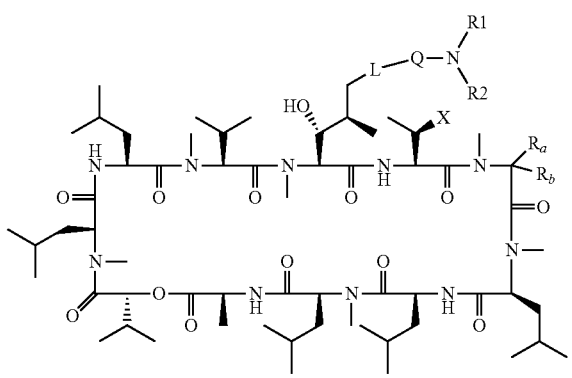

or a pharmaceutically acceptable salt, tautomer or N-oxide thereof, wherein

L represents a bond or an optionally substituted, optionally partially unsaturated chain of 1-6 carbon atoms with optional additional heteroatoms atoms in the chain, and may be optionally branched and optionally linked to $R_1$ to form a ring structure containing one or more nitrogen atoms, Q represents a primary, secondary or tertiary covalent bond, a carbonyl group and optionally a linking group to R1, R1 and R2 may be absent or independently represent H, alkyl, substituted alkyl, optionally substituted cycloalkyl, optionally substituted aryl, optionally substituted heteroaryl, —COR$_3$, —CO$_2$R$_3$, —OR$_4$, —NR$_4$R$_5$, CONR$_4$R$_5$, —C(=NR$_6$)NR$_4$R$_5$, —C(=NR$_6$)OR$_3$ and optionally R1 and R2 may together with the nitrogen atom to which they are attached form a 4-7 membered aryl, cycloalkyl or heterocyclic ring which may be further fused or optionally substituted, R3 represents alkyl, substituted alkyl, cycloalkyl, optionally substituted aryl, or optionally substituted heteroaryl, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, R6 represents H, alkyl, substituted alkyl, cycloalkyl, optionally substituted aryl, or optionally substituted heteroaryl, X represents H, OH, OC(=O)-alkyl, OC(=O)-substituted alkyl, O-alkyl, O-substituted alkyl, carbonyl (=O) or imine (=N—Y) where Y is —OR$_4$ or —NR$_4$R$_5$, $R_a$ represents hydrogen, alkyl, substituted alkyl, alkoxy, substituted alkoxy, alkylthio, substituted alkylthio or optionally substituted alkylene, and $R_b$ represents hydrogen or is absent.

2. The compound according to claim 1 wherein L is an optionally partially unsaturated chain of 1-6 carbon atoms, Q is a primary covalent bond or a carbonyl group and R1 and R2 together with the nitrogen atom to which they are attached form a 4-7 membered aryl, cycloalkyl or heterocyclic ring which may be further fused or optionally substituted.

3. The compound according to claim 2 wherein R1 and R2 together with the nitrogen atom to which they are attached form a 5-7 membered cycloalkyl or heterocyclic ring which may be further fused or optionally substituted.

4. The compound according to claim 2 wherein the group L-Q-NR1-R2 is selected from —(CH$_2$)$_n$—NR1R2 where n is 1-4 and NR1-R2 is an optionally substituted ring selected from:

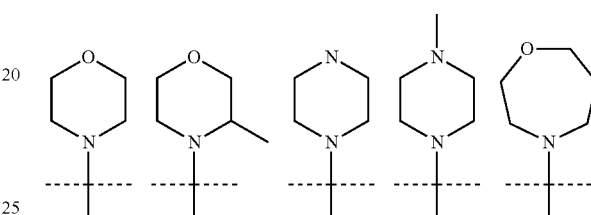

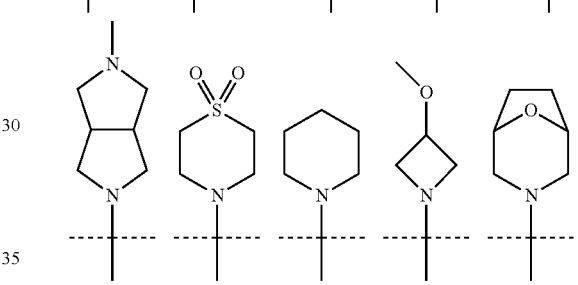

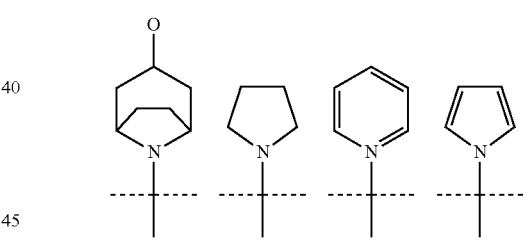

5. The compound according to claim 1 wherein L is a C1-6 alkyl group with 0-1 heteroatom substituents, Q is a primary covalent bond and R1 and R2 are independently H, alkyl or substituted alkyl groups.

6. The compound according to claim 1 wherein R1 is methyl.

7. The compound according to claim 1 where Q is tertiary, and R1 and R2 are absent.

8. The compound according to claim 1 where L or Q is linked to $R_1$ to form a ring structure containing one or more nitrogen atoms.

9. The compound according to claim 8 wherein the ring is aromatic.

10. The compound according to claim 9 wherein the ring is an optionally substituted 6 membered ring.

11. The compound according to claim 10 having the formula

117

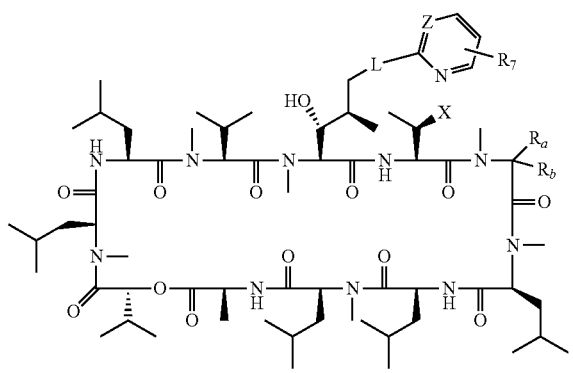

or a pharmaceutically acceptable salt, tautomer or N-oxide thereof, wherein

L represents a bond or an optionally substituted, optionally partially unsaturated chain of 1-6 carbon atoms with optional additional heteroatoms atoms in the chain, and may be optionally branched, Z represents N or CH, R7 represents H, optionally substituted alkyl, NH2, heterocycloalkyl, —NR4R5, R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, X represents H, OH, OC(=O)-alkyl, OC(=O)-substituted alkyl, O-alkyl, O-substituted alkyl, carbonyl (=O) or imine (=N—Y) where Y is —OR4 or —NR4R5, $R_a$ represents hydrogen, alkyl, substituted alkyl, alkoxy, substituted alkoxy, alkylthio, substituted alkylthio or optionally substituted alkylene, and $R_b$ represents hydrogen or is absent.

12. The compound according to claim 1 where L is a C1-6 alkyl group with 0-1 heteroatom substituents, Q is carbonyl and Q-NR1R2 is represented by a structure of type:

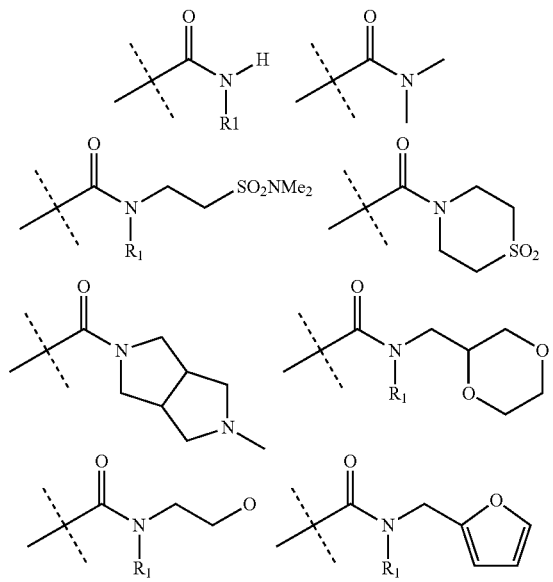

118

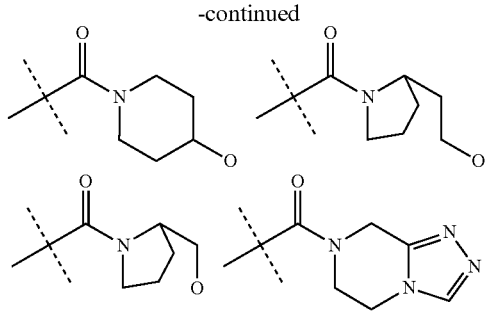

where R1 is H or alkyl.

13. The compound according to claim 1 where Q is a secondary covalent bond, R1 is absent and R2 is —OR4 or —NR4R5, where R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted.

14. The compound according to claim 13 where R2 is selected from the structures represented by:

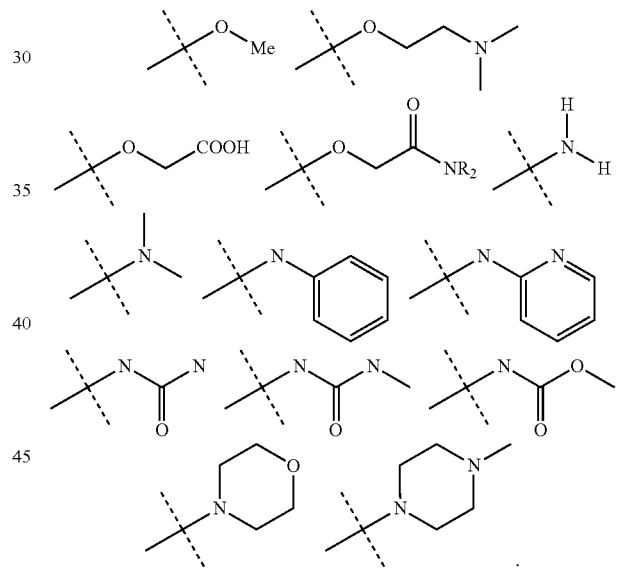

15. The compound according to claim 8 where the ring structure is represented by a structure of type:

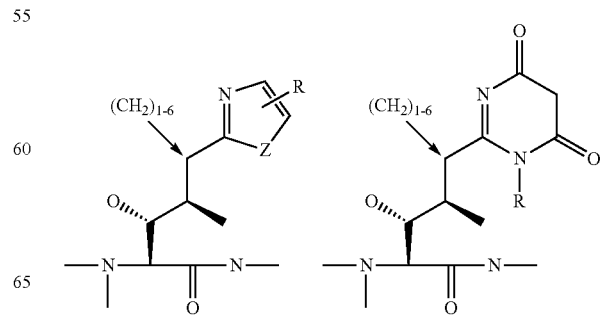

-continued where Z represents O, S or NH or N-alkyl and R represents H or more optional substituents.

16. The compound according to claim 1 where Q represents a primary covalent bond,
R1 represents H, alkyl or substituted alkyl,
R2 represents, —COR$_3$, —CO$_2$R$_3$, —CONR$_4$R$_5$, —C(=NR$_6$)NR$_4$R$_5$, or —C(=NR$_6$)OR$_3$, where
R3 represents alkyl, substituted alkyl, cycloalkyl, optionally substituted aryl, or optionally substituted heteroaryl,
R4 and R5 independently represent H, alkyl, substituted alkyl, cycloalkyl, optionally substituted aryl, or optionally substituted heteroaryl and optionally R4 and R5 may together with the nitrogen atom to which they are attached form a 4-7 membered aryl, cycloalkyl or heterocyclic ring which may be further fused or optionally substituted, and
R6 represents H, alkyl, substituted alkyl, cycloalkyl, optionally substituted aryl, or optionally substituted heteroaryl.

17. The compound according to claim 1 where R1 and R2 are optionally substituted alkyl groups.

18. The compound according to claim 1 which is a compound selected from the group consisting of:
cyclo-[(3R,4R,5S)-4-(hydroxy)-3-methyl-5-(methylamino)-1-N-morpholino-hexanoic acid-Thr-Sar-MeLeu-Leu-MeLeu-Ala-D-Hiv-MeLeu-Leu-MeVal];
cyclo-[(3R,4R,5S)-4-(hydroxy)-3-methyl-5-(methylamino)-1-N-(methyl-pyridin-4-ylmethyl-amino)-hexanoic acid-Thr-Sar-MeLeu-Leu-MeLeu-Ala-D-Hiv-MeLeu-Leu-MeVal];
cyclo-{(3R,4R,5S)-4-(hydroxy)-3-methyl-5-(methylamino)-1-N-[methyl-2-(pyridin-2-yl)-ethyl-amino]-hexanoic acid-Thr-Sar-MeLeu-Leu-MeLeu-Ala-D-Hiv-MeLeu-Leu-MeVal};
cyclo-{(3R,4R,5S)-4-(hydroxy)-3-methyl-5-(methylamino)-1-N-[methyl-(2-methyl-2H-pyrazol-3-ylmethyl)-amino]-hexanoic acid-Thr-Sar-MeLeu-Leu-MeLeu-Ala-D-Hiv-MeLeu-Leu-MeVal};
cyclo-{(3R,4R,5S)-4-(hydroxy)-3-methyl-5-(methylamino)-1-N-[methyl-(1H-tetrazol-5-ylmethyl)-amino]-hexanoic acid-Thr-Sar-MeLeu-Leu-MeLeu-Ala-D-Hiv-MeLeu-Leu-MeVal};
cyclo-[(3R,4R,5S)-4-(hydroxy)-3-methyl-5-(methylamino)-1-N-morpholino-hexanoic acid-(O-methyl-Thr)-Sar-MeLeu-Leu-MeLeu-Ala-D-Hiv-MeLeu-Leu-MeVal];
cyclo-{(3R,4R,5S)-4-(hydroxy)-3-methyl-5-(methylamino)-1-N-([1,4]dioxan-2-ylmethyl-methyl-amino)-hexanoic acid-Thr-Sar-MeLeu-Leu-MeLeu-Ala-D-Hiv-MeLeu-Leu-MeVal};
cyclo-{(3R,4R,5S)-4-(hydroxy)-3-methyl-5-(methylamino)-1-N-[3-trifluoromethyl-piperidinyl]-hexanoic acid-Thr-Sar-MeLeu-Leu-MeLeu-Ala-D-Hiv-MeLeu-Leu-MeVal};
cyclo-{(3R,4R,5S)-4-(hydroxy)-3-methyl-5-(methylamino)-1-N-[(2-methoxy-ethyl)-methyl-amino]-hexanoic acid-Thr-Sar-MeLeu-Leu-MeLeu-Ala-D-Hiv-MeLeu-Leu-MeVal};
cyclo-{(3R,4R,5S)-4-(hydroxy)-3-methyl-5-(methylamino)-1-N-[(3-methoxy-azetidinyl)-hexanoic acid-Thr-Sar-MeLeu-Leu-MeLeu-Ala-D-Hiv-MeLeu-Leu-MeVal};
cyclo-{(3R,4R,5S)-4-(hydroxy)-3-methyl-5-(methylamino)-1-N-(methyl-(tetrahydro-pyran-4-yl)-amino)-hexanoic acid-Thr-Sar-MeLeu-Leu-MeLeu-Ala-D-Hiv-MeLeu-Leu-MeVal};
cyclo-[(3R,4R,5S)-4-(hydroxy)-3-methyl-5-(methylamino)-1-N-morpholino-hexanoic acid-Abu-Sar-MeLeu-Leu-MeLeu-Ala-D-Hiv-MeLeu-Leu-MeVal];
cyclo-[(3R,4R,5S)-4-(hydroxy)-3-methyl-5-(methylamino)-1-(6-methyl-pyridin-2-yl)-hept-1-enoic acid-Thr-Sar-MeLeu-Leu-MeLeu-Ala-D-Hiv-MeLeu-Leu-MeVal];
cyclo-{(3R,4R,5S)-4-(hydroxy)-3-methyl-5-(methylamino)-1-(pyrimidin-2-yl)-hept-1-enoic acid-Thr-Sar-MeLeu-Leu-MeLeu-Ala-D-Hiv-MeLeu-Leu-MeVal};
cyclo-[(3R,4R,5S)-4-(hydroxy)-3-methyl-5-(methylamino)-1-(pyrimidin-2-yl)-heptanoic acid-Thr-Sar-MeLeu-Leu-MeLeu-Ala-D-Hiv-MeLeu-Leu-MeVal];
cyclo-[(3R,4R,5S)-4-(hydroxy)-3-methyl-5-(methylamino)-1-(6-methyl-pyridin-2-yl)-heptanoic acid-Thr-Sar-MeLeu-Leu-MeLeu-Ala-D-Hiv-MeLeu-Leu-MeVal];
cyclo-{(3R,4R,5S)-4-(hydroxy)-3-methyl-5-(methylamino)-1-(6-morpholin-4-yl-pyridin-2-yl)-hept-1-enoic acid-Thr-Sar-MeLeu-Leu-MeLeu-Ala-D-Hiv-MeLeu-Leu-MeVal};
cyclo-[(3R,4R,5S)-4-(hydroxy)-3-methyl-5-(methylamino)-1-(6-methyl-pyridin-2-yl)-hept-1-enoic acid-Abu-Sar-MeLeu-Leu-MeLeu-Ala-D-Hiv-MeLeu-Leu-MeVal];
cyclo-[(3R,4R,5S)-4-(hydroxy)-3-methyl-5-(methylamino)-1-(6-morpholin-4-yl-pyridin-2-yl)-heptanoic acid-Thr-Sar-MeLeu-Leu-MeLeu-Ala-D-Hiv-MeLeu-Leu-MeVal];
cyclo-[(3R,4R,5S)-4-(hydroxy)-3-methyl-5-(methylamino)-1-(6-methyl-pyridin-2-yl)-heptanoic acid-Abu-Sar-MeLeu-Leu-MeLeu-Ala-D-Hiv-MeLeu-Leu-MeVal];
cyclo-[(3R,4R,5S)-4-(hydroxy)-3-methyl-5-(methylamino)-1-N-(8-oxa-3-aza-bicyclo[3.2.1]octane)-hexanoic acid-Thr-Sar-MeLeu-Leu-MeLeu-Ala-D-Hiv-MeLeu-Leu-MeVal];
cyclo-[(3R,4R,5S)-4-(hydroxy)-3-methyl-5-(methylamino)-1-N-(thiomorpholine 1,1-dioxide)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N-(4,4-difluoro-piperidine)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N-((4-fluoro-piperidin-4-yl)-methanol)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N-((S)-1-Pyrrolidin-2-yl-methanol)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N-(3-methylamino-propionitrile)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N-(methyl-pyridin-2-yl-amine)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N—((R)-3-Methyl-morpholine)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N-(bis-pyridin-2-ylmethyl-amine)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N-(methyl-pyridin-2-ylmethyl-amino)-hexanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-N—(N'-methylpiperazine)-hexanoic acid-Thr-Sar-MeLeu-Leu-MeLeu-Ala-D-Hiv-MeLeu-Leu-MeVal];

cyclo-[(2R,3R,4S)-1-(1H-benzoimidazol-2-yl)-2-methyl-4-methylamino-3-hydroxy-pentanoic acid-Thr-Sar-MeLeu-Leu-MeLeu-Ala-D-Hiv-MeLeu-Leu-MeVal];

cyclo-[(3R,4R,5S)-4-(hydroxy)-3-methyl-5-(methylamino)-1-(4-phenyl-1-piperidyl)-hexanoic acid-Thr-Sar-MeLeu-Leu-MeLeu-Ala-D-Hiv-MeLeu-Leu-MeVal];

cyclo-[(3R,4R,5S)-1-benzylamino-3-methyl-5-methylamino-4-hydroxy-hexanoic acid-Thr-Sar-MeLeu-Leu-MeLeu-Ala-D-Hiv-MeLeu-Leu-MeVal];

cyclo-[(3R,4R,5S)-1-benzylcarbamoyl-3-methyl-5-methylamino-4-hydroxy-pentanoic acid-Thr-Sar-MeLeu-Leu-MeLeu-Ala-D-Hiv-MeLeu-Leu-MeVal];

cyclo-[(3R,4R,5S)-4-hydroxy-1-isopropylamino-3-methyl-5-methylamino-hexanoic acid-Thr-Sar-MeLeu-Leu-MeLeu-Ala-D-Hiv-MeLeu-Leu-MeVal];

cyclo-[(3R,4R,5S)-1-(acetyl-isopropyl-amino)-4-hydroxy-3-methyl-5-methylamino-hexanoic acid-Thr-Sar-MeLeu-Leu-MeLeu-Ala-D-Hiv-MeLeu-Leu-MeVal]; and cyclo-[(2R,3R,4S)-4-hydroxy-1-(2-hydroxymethyl-piperidin-1-yl)-3-methyl-5-methylamino-hexanoic acid-Thr-Sar-MeLeu-Leu-MeLeu-Ala-D-Hiv-MeLeu-Leu-MeVal].

19. A pharmaceutical composition containing the compound according to claim 1.

20. A method of treating or preventing a disease or a pathological condition which is ameliorated by the inhibition of cyclophilin activity, comprising administering an effective amount of the compound of claim 1 to a subject in need thereof such that the disease or pathological condition is treated or prevented.

\* \* \* \* \*